United States Patent
Wan

(10) Patent No.: US 9,879,260 B2
(45) Date of Patent: Jan. 30, 2018

(54) MICRO-RNA REGULATION OF BONE LOSS

(71) Applicant: The Board of Regents of the University of Texas System, Austin, TX (US)

(72) Inventor: Yihong Wan, Dallas, TX (US)

(73) Assignee: The Board of Regents of the University of Texas System, Austin, TX (US)

( * ) Notice: Subject to any disclaimer, the term of this patent is extended or adjusted under 35 U.S.C. 154(b) by 0 days.

(21) Appl. No.: 14/913,005

(22) PCT Filed: Aug. 14, 2014

(86) PCT No.: PCT/US2014/050985
§ 371 (c)(1),
(2) Date: Feb. 19, 2016

(87) PCT Pub. No.: WO2015/026611
PCT Pub. Date: Feb. 26, 2015

(65) Prior Publication Data
US 2016/0201056 A1    Jul. 14, 2016

Related U.S. Application Data

(60) Provisional application No. 61/867,768, filed on Aug. 20, 2013.

(51) Int. Cl.
*C12N 15/113* (2010.01)
*A61K 31/713* (2006.01)
*A61K 31/7088* (2006.01)
*A61K 45/06* (2006.01)
*A61K 31/7105* (2006.01)

(52) U.S. Cl.
CPC ........ *C12N 15/113* (2013.01); *A61K 31/7088* (2013.01); *A61K 31/713* (2013.01); *A61K 31/7105* (2013.01); *A61K 45/06* (2013.01); *C12N 2310/141* (2013.01); *C12N 2320/30* (2013.01); *C12N 2320/31* (2013.01)

(58) Field of Classification Search
CPC ............ C12N 15/113; C12N 2310/141; C12N 15/111
See application file for complete search history.

(56) References Cited

U.S. PATENT DOCUMENTS

2009/0227533 A1    9/2009  Bader et al.
2012/0294868 A1    11/2012 Edwards et al.

FOREIGN PATENT DOCUMENTS

| WO | WO 2008-154333 | 12/2008 |
| WO | WO 2011-029903 | 3/2011 |
| WO | WO 2012-020307 | 2/2012 |
| WO | WO 2012-020308 | 2/2012 |

OTHER PUBLICATIONS

Jen et al. (Stem Cells 2000, vol. 18, p. 307-319).*
Opalinska et al. (Nature Reviews Drug Discovery, 2002, vol. 1, p. 503-514).*
Bae et al., "miRNA-34c regulates Notch signaling during bone development ," *Hum Mol Genet*, 21:2991-3000, 2012.
Bommer et al., "p53-mediated activation of miRNA34 candidate tumor-suppressor genes," *Current Biology*, 17:1298-1307, 2007.
Chang et al., "Transactivation of miR-34a by p53 broadly influences gene expression and promotes apoptosis ," *Molecular Cell*, 26:745-752, 2007.
Chang et al., "Widespread microRNA repression by Myc contributes to tumorigenesis," *Nature Genetics*, 40:43-50, 2008.
Choi et al., "miR-34 miRNAs provide a barrier for somatic cell reprogramming ," *Nature Cell Biology*, 13(11):1353-1360, 2011.
Concepcion et al., "Intact p53-dependent responses in miR-34-deficient mice," *PLoS Genet*, 8(7):e1002797, 2012.
Corney et al., "MicroRNA-34b and MicroRNA-34c are targets of p53 and cooperate in control of cell proliferation and adhesion-independent growth ," *Cancer Research*, 67:8433-8438, 2007.
Di Martino et al., "Synthetic miR-34a mimics as a novel therapeutic agent for multiple myeloma: in vitro and in vivo evidence," *Clin Cancer Res.*, 18(22):6260-6270, 2012.
He et al., "microRNAs join the p53 network—another piece in the tumour-suppression puzzle ," *Nature Reviews Cancer*, 7:819-822, 2007.
Hermeking, "p53 enters the microRNA world," *Cancer Cell*, 12:414-418, 2007.
Krzeszinski et al., "miR-34a blocks osteoporosis and bone metastasis by inhibiting osteoclastogenesis and Tgif2," *Nature*, 512(7515):431-435, 2014.
Liu et al., "The microRNA miR-34a inhibits prostate cancer stem cells and metastasis by directly repressing CD44," *Nature Medicine*, 17:211-215, 2011.
Lodygin et al., "Inactivation of miR-34a by aberrant CpG methylation in multiple types of cancer," *Cell Cycle*, 7:2591-2600, 2008.
PCT International Preliminary Report on Patentability issued in International Application No. PCT/US2014/050985, dated Mar. 3, 2016.
PCT International Search Report and Written Opinion issued in International Application No. PCT/US2014/050985, dated Nov. 25, 2014.
Pramanik et al., "Restitution of tumor suppressor microRNAs using a systemic nanovector inhibits pancreatic cancer growth in mice," *Molecular Cancer Therapeutics*, 10:1470-1480, 2011.
Raitoharju et al., "miR-21, miR-210, miR-34a, and miR-146a/b are up-regulated in human atherosclerotic plaques in the Tampere Vascular Study," *Atherosclerosis*, 219:211-217, 2011.
Raver-Shapira et al., "Transcriptional activation of miR-34a contributes to p53-mediated apoptosis," *Molecular Cell*, 26:731-743, 2007.

(Continued)

*Primary Examiner* — J. E. Angell
(74) *Attorney, Agent, or Firm* — Parker Highlander PLLC

(57) ABSTRACT

The use of miR-34a and agonists thereof in the treatment of bone loss diseases is described. Such conditions include osteoporosis, rheumatoid arthritis and other bone wasting diseases.

17 Claims, 14 Drawing Sheets

(56) References Cited

OTHER PUBLICATIONS

Tarasov et al., "Differential regulation of microRNAs by p53 revealed by massively parallel sequencing: miR-34a is a p53 target that induces apoptosis and G1-arrest," *Cell Cycle*, 6:1586-1593, 2007.

Tazawa et al., "Tumor-suppressive miR-34a induces senescencein-like growth arrest through modulation of the E2F pathway human colon cancer cells," *Proceedings of the National Academy of Sciences of the United States of America*, 104:15472-15477, 2007.

Trang et al., "Systemic delivery of tumor suppressor microRNA mimics using a neutral lipid emulsion inhibits lung tumors in mice," *Molecular Therapy*, 19:1116-1122, 2011.

Wei et al., "miR-34s inhibit osteoblast proliferation and differentiation in the mouse by targeting SATB2," *J. Cell Biol.*, 197(4):509-521, 2012.

Welch et al., "MicroRNA-34a functions as a potential tumor suppressor by inducing apoptosis in neuroblastoma cells," *Oncogene*, 26:5017-5022, 2007.

Wiggins et al., "Development of a lung cancer therapeutic based on the tumor suppressor microRNA-34," *Cancer Research*, 70:5923-5930, 2010.

Woolf and Pfleger, "Burden of major musculoskeletal conditions," *Bulletin of the World Health Organization*, 81(9):646-656, 2003.

Yan et al., "MicroRNA-34a inhibits the proliferation and metastasis of osteosarcoma cells both in vitro and in vivo," *PLoS ONE*, 7(3):e33778, 2012.

* cited by examiner

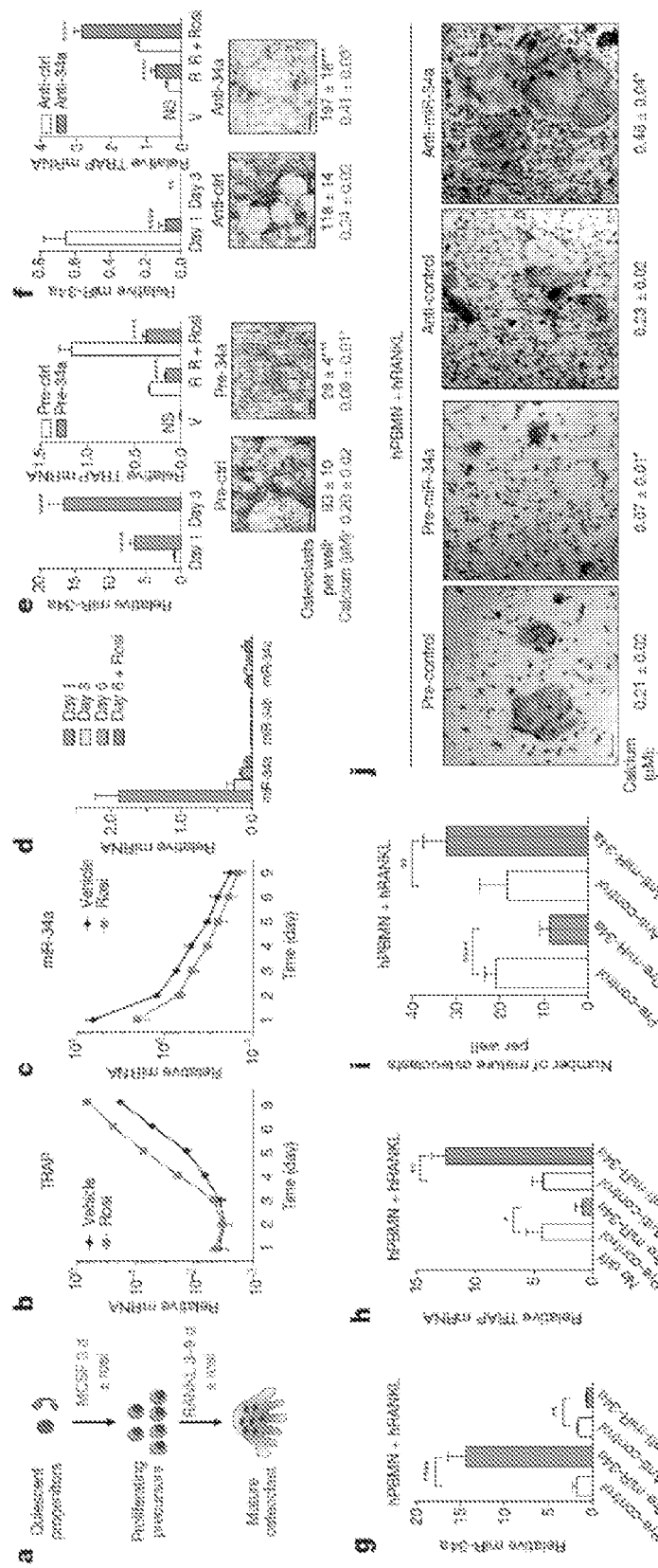
FIGs. 1A-J

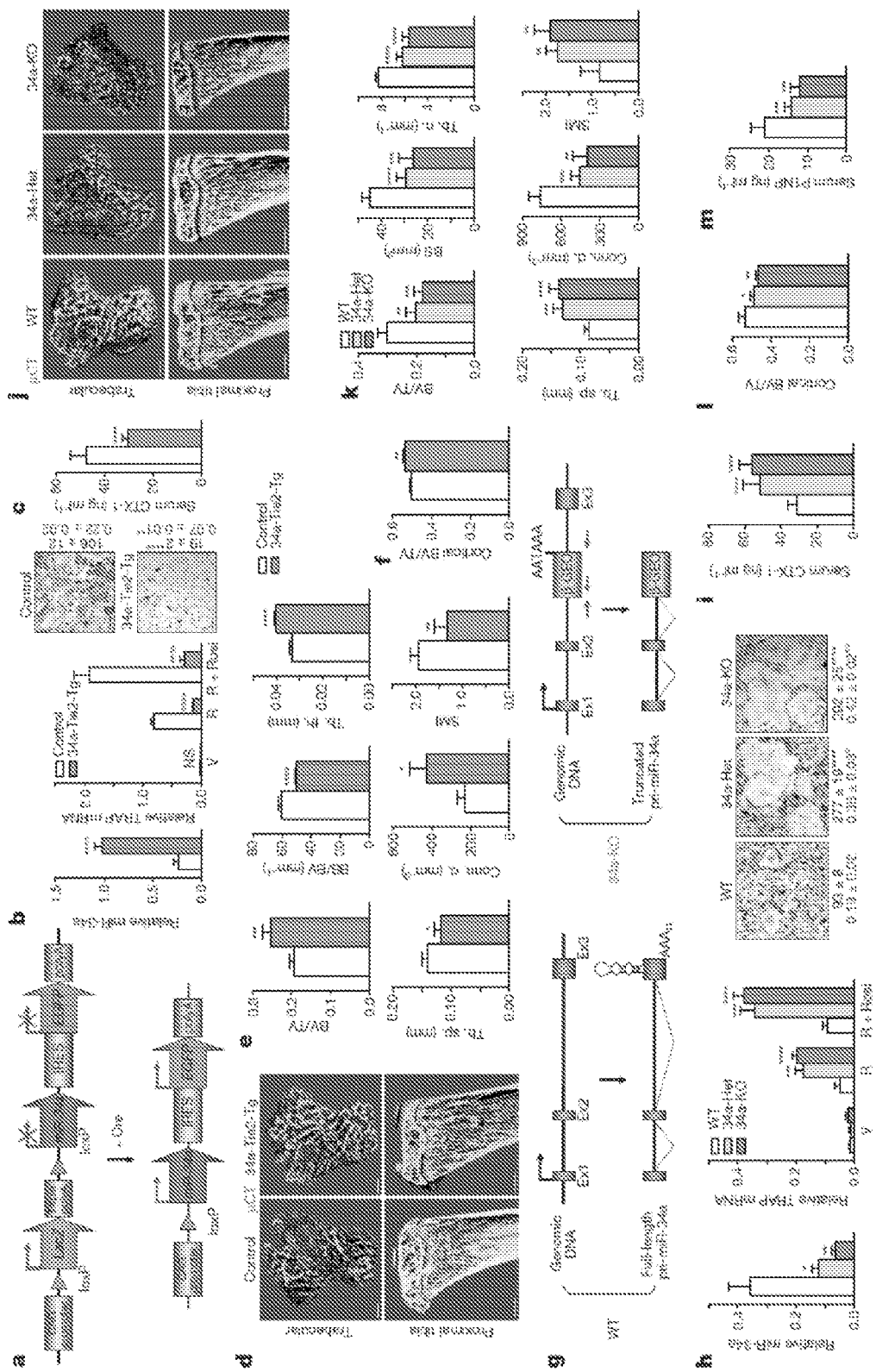
FIGs. 2A-M

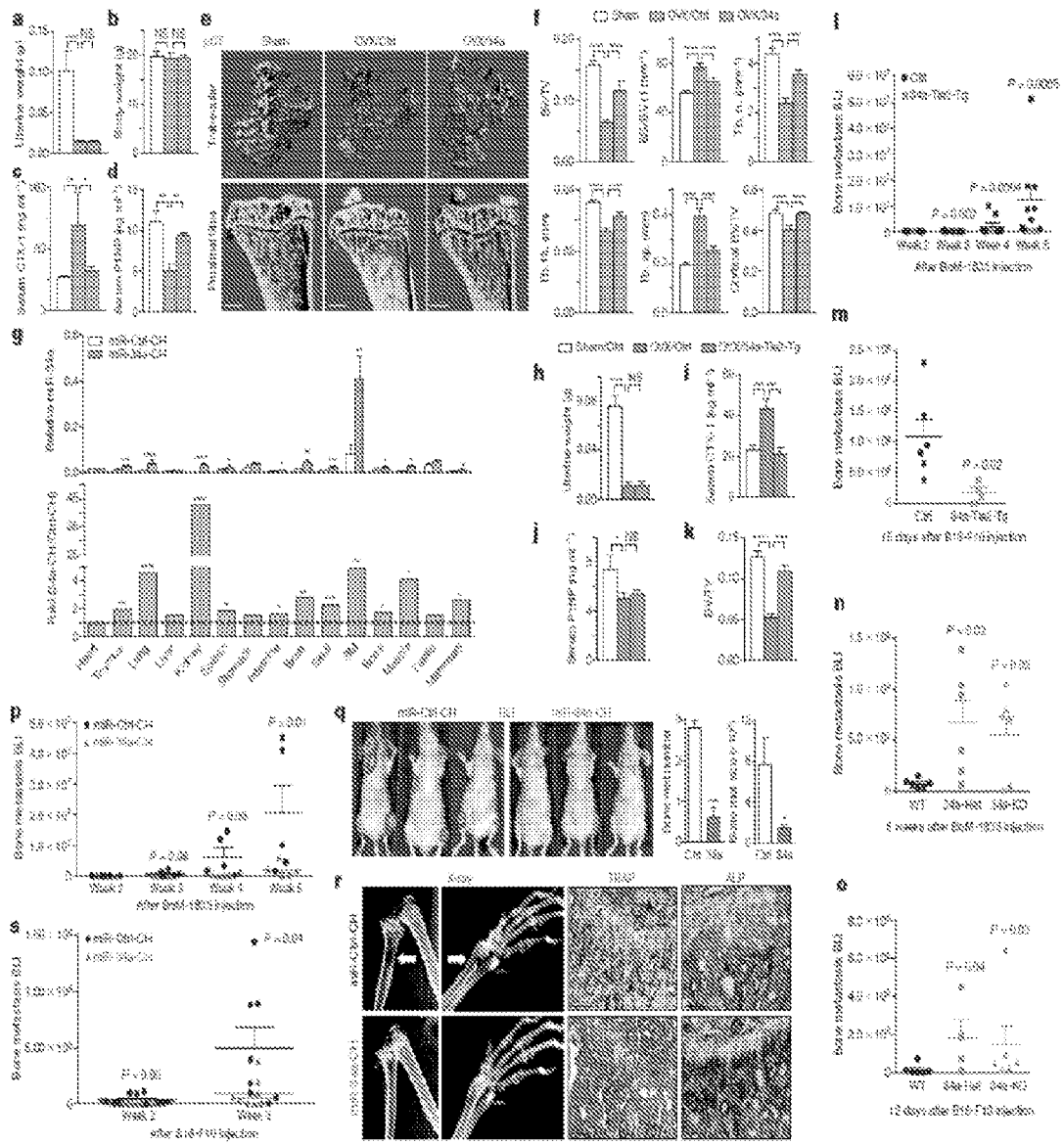
FIGs. 3A-S

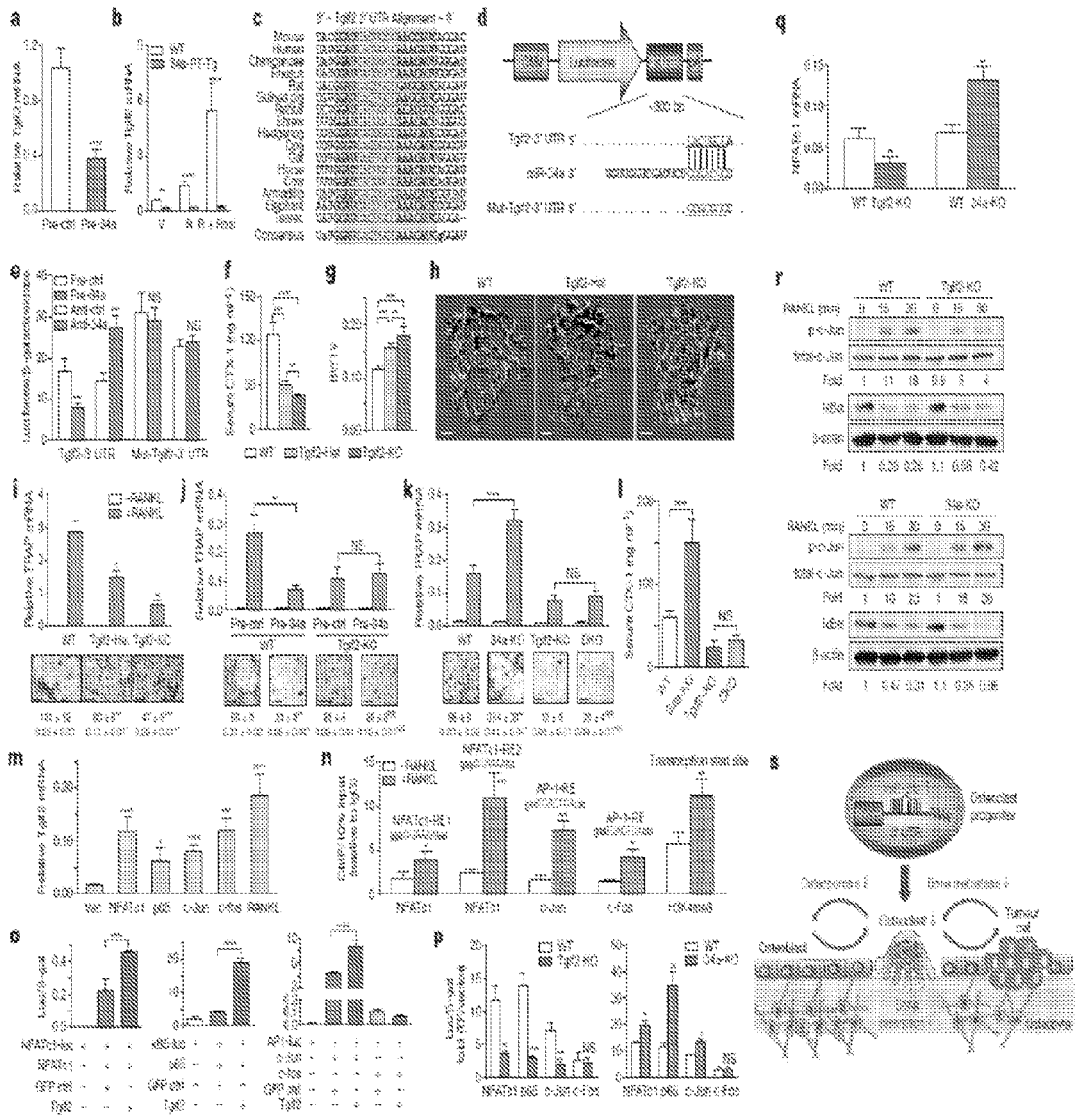
FIGs. 4A-S

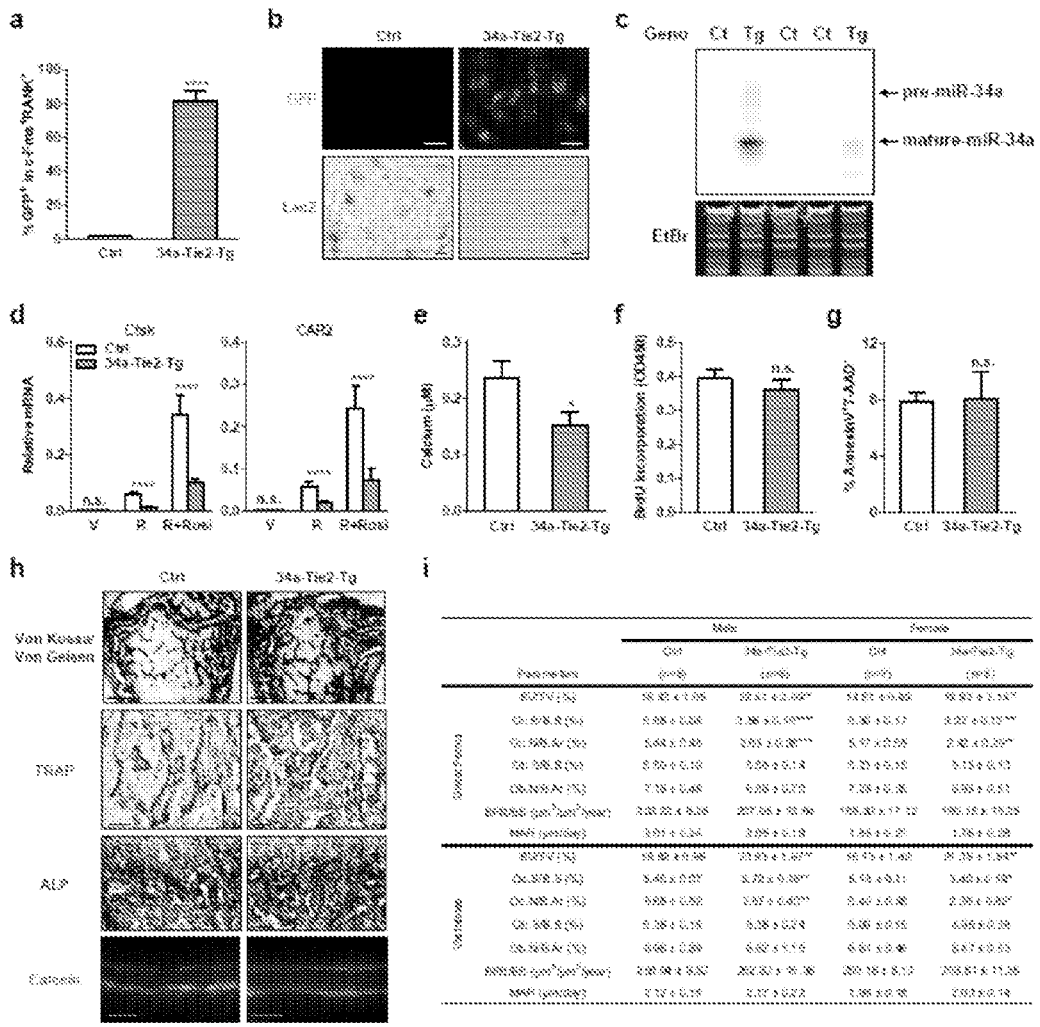
FIGs. 5A-I

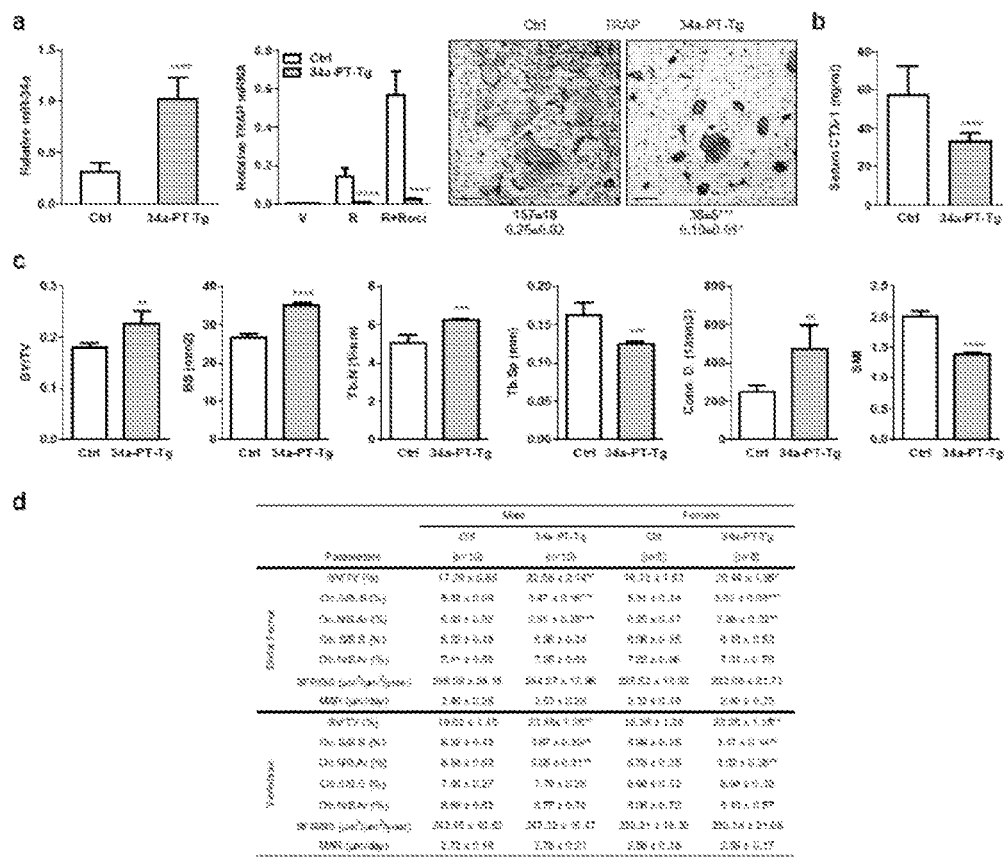
FIGs. 6A-D

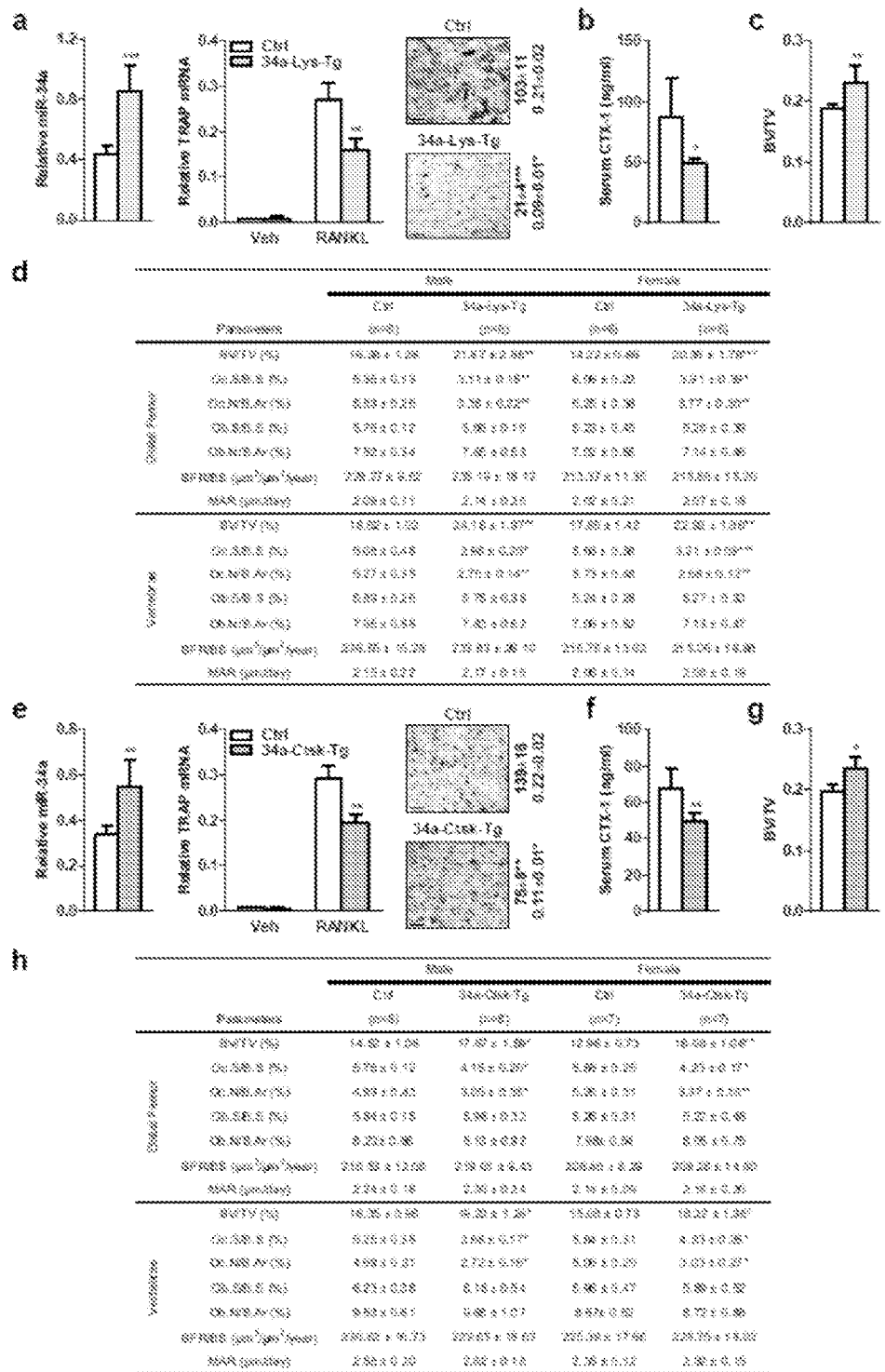
FIGs. 7A-H

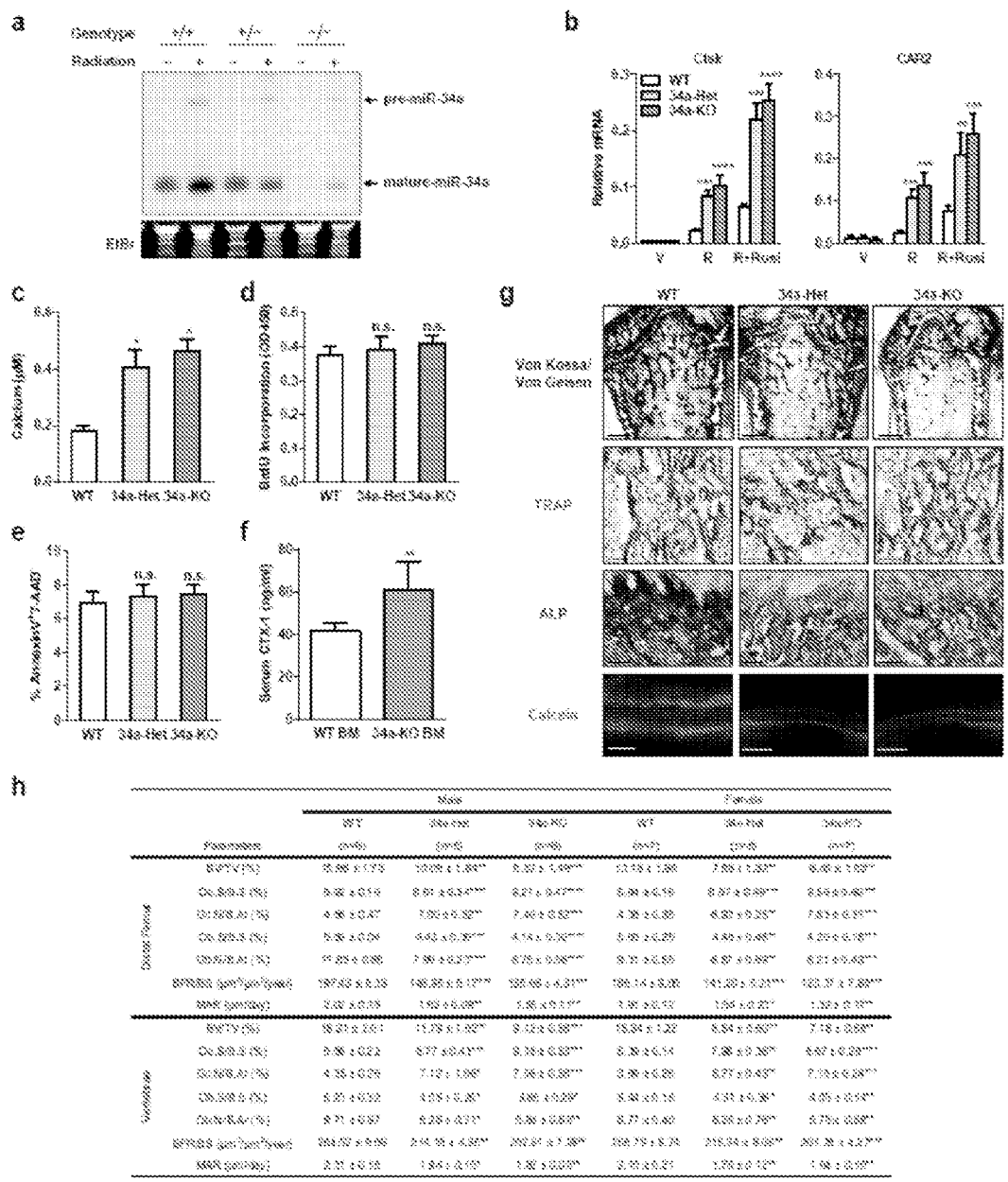
FIGs. 8A-H

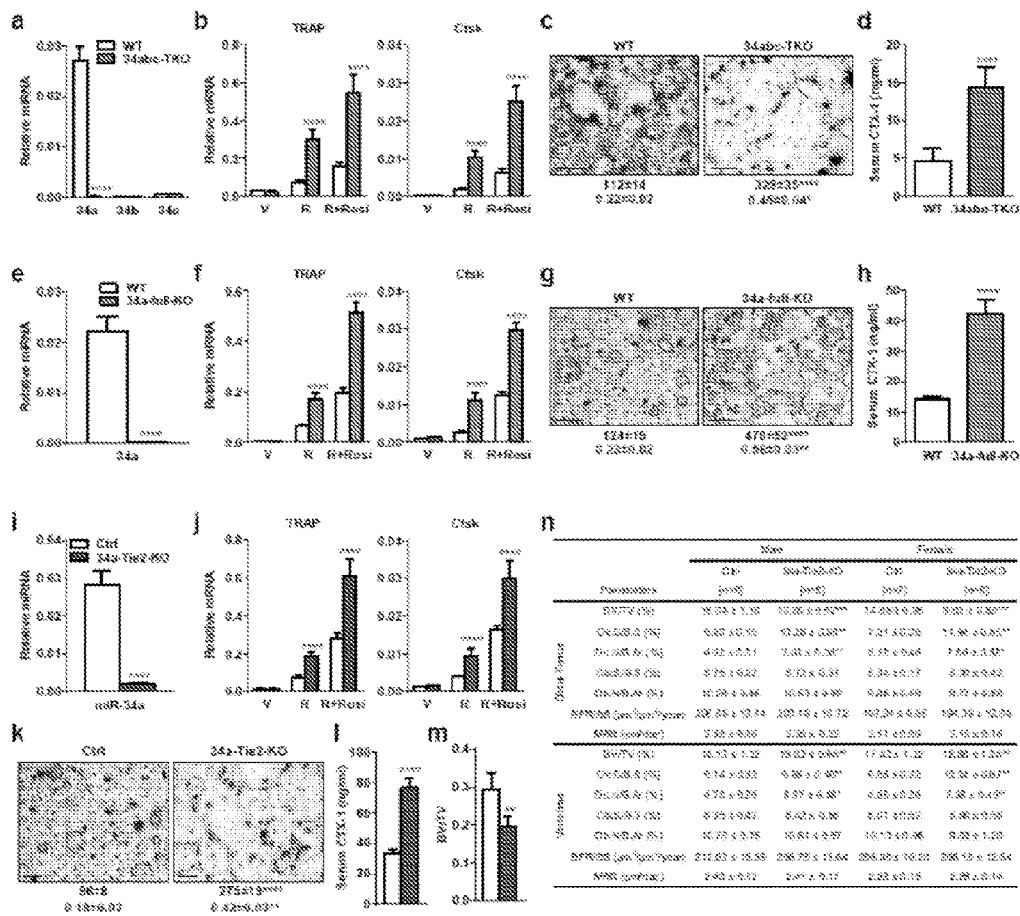
FIGs. 9A-N

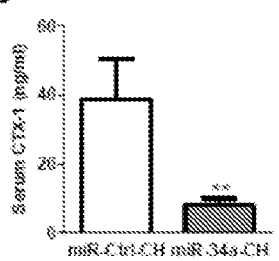
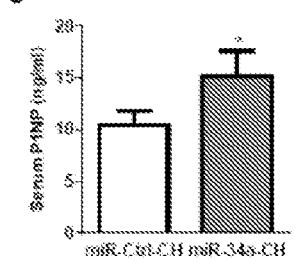
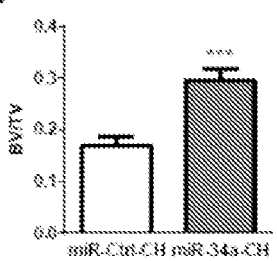
FIGs. 10A-E

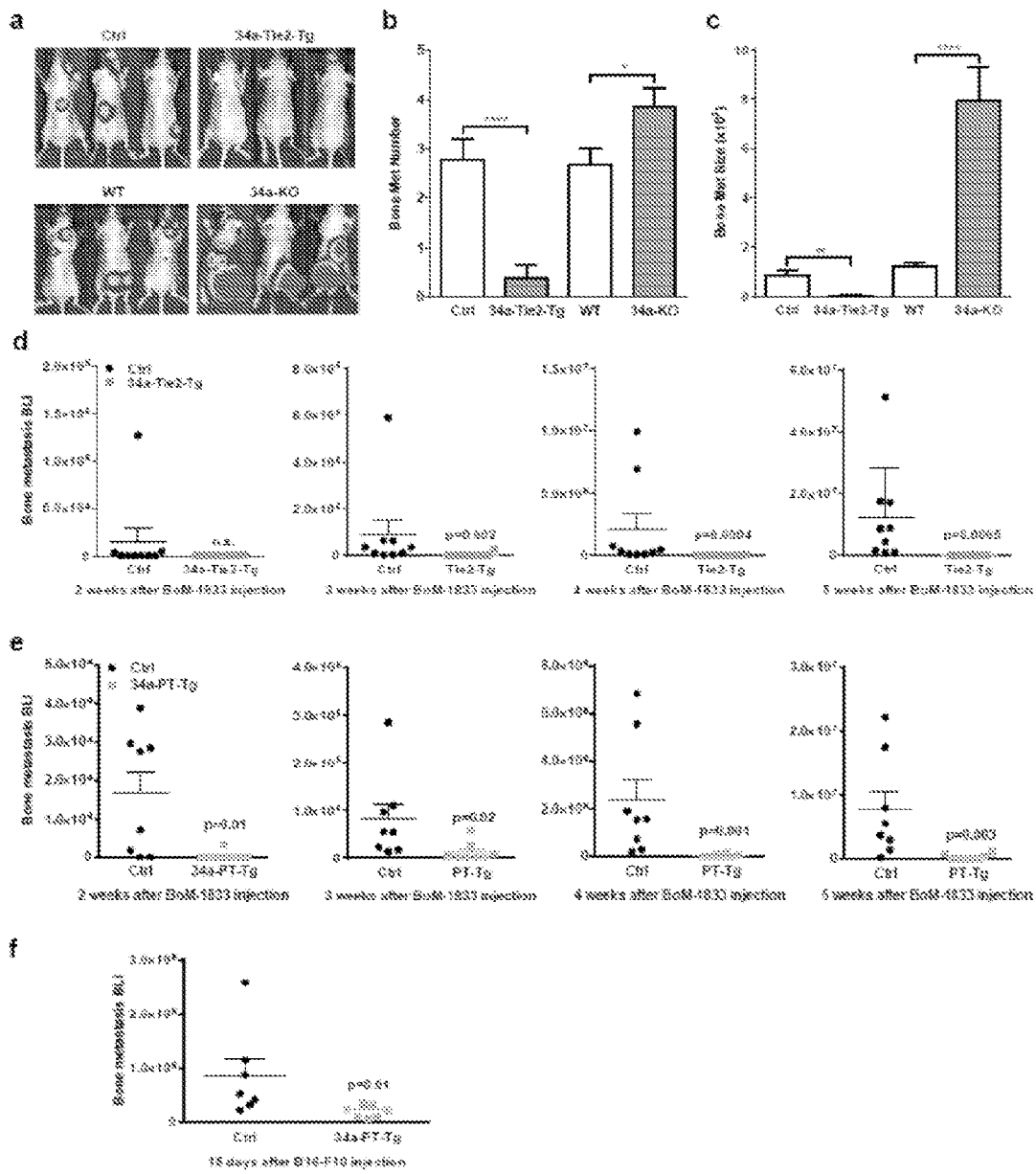
FIGs. 11A-F

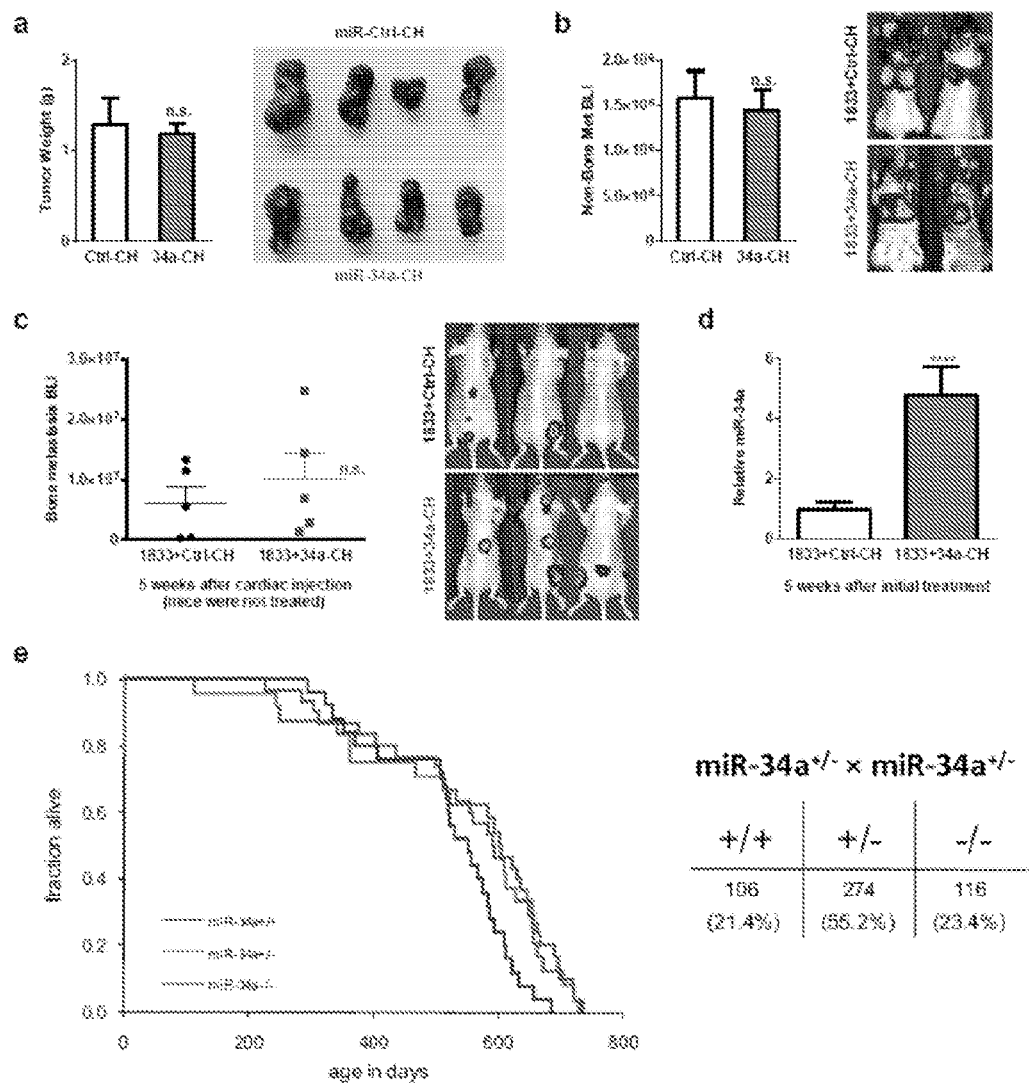
FIGs. 12A-E

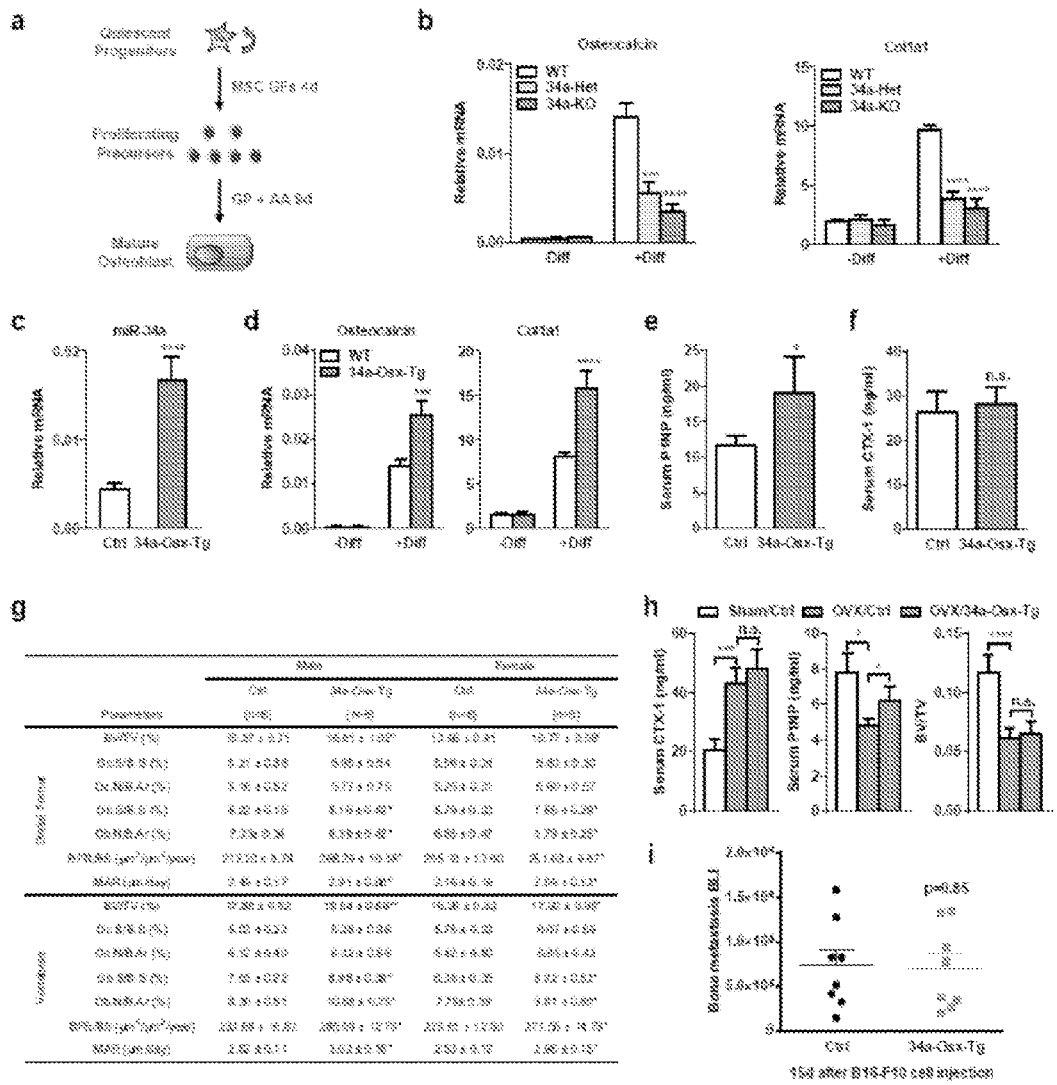
FIGs. 13A-I

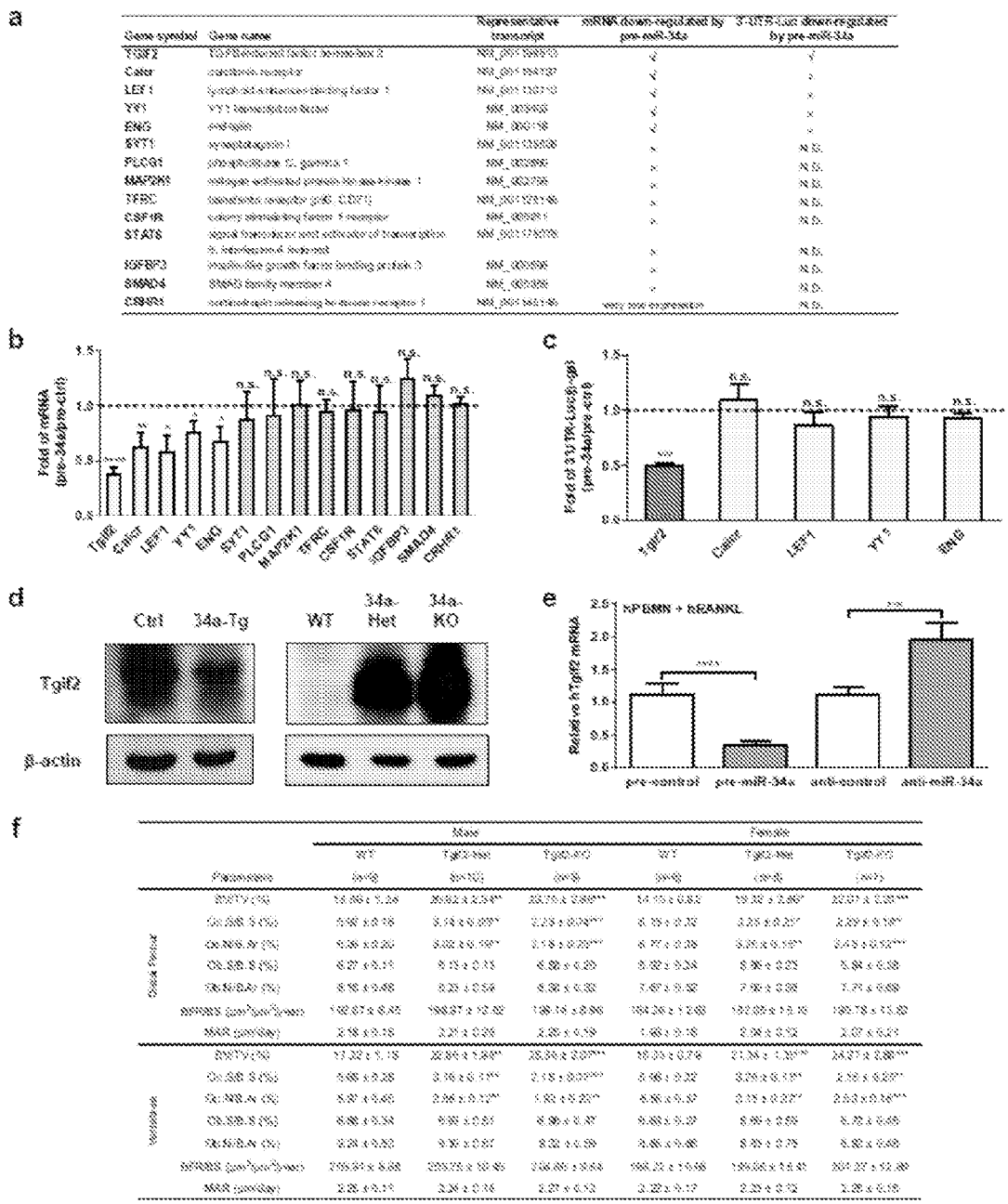
FIGs. 14A-F

MICRO-RNA REGULATION OF BONE LOSS

This application is a national phase application under 35 U.S.C. §371 of International Application No. PCT/US2014/050985, filed Aug. 14, 2014, which claims benefit of priority to U.S. Provisional Application Ser. No. 61/867,768, filed Aug. 20, 2013, the entire contents of each of which are hereby incorporated by reference.

The invention was made with government support under Grant No. R01DK089113 awarded by the National Institutes of Health. The government has certain rights in the invention.

BACKGROUND OF THE INVENTION

1. Field of the Invention

The present invention relates generally to the fields of medicine, pathology and molecular biology. More particularly, it concerns the involvement of miR function in the regulation of osteoclasts and osteoblasts. Specifically, the invention relates to the use of miR-34a for treating bone loss.

2. Description of Related Art

Osteoclast-mediated bone resorption plays an essential role in the dynamic bone remodeling in concert with osteoblast-mediated bone formation. Osteoclasts are derived from hematopoietic progenitors (Ash et al., 1980) in the monocyte/macrophage lineage (Scheven et al., 1986; Tondravi et al., 1997), and differentiate in response to the cytokine Receptor Activator of NFκB Ligand (RANKL) (Lacey et al., 1998; Yasuda et al., 1998); whereas osteoblasts are of mesenchymal lineage (Pittenger et al., 1999). Skeletal homeostasis in normal physiology is maintained by the tight coupling of bone resorption and bone formation (Edwards and Mundy, 2008). However, pathological increases in osteoclast function can cause several bone diseases such as osteoporosis (Novack and Teitelbaum, 2008). It is estimated that an osteoporotic fracture occurs every 3 seconds worldwide, many of which leads to life-threatening events especially in the elderly. With the increased prevalence and life-time risk, osteoporosis takes a huge personal and economic toll.

Excessive osteoclasts also promote bone metastasis, a frequent, debilitating and essentially incurable cancer complication that accounts for substantial morbidity and mortality in cancer patients. A bevy of tumors exhibit a strong tendency to metastasize to the bone, including breast, prostate, lung, skin, colon, stomach, bladder, uterus, rectum, thyroid and kidney cancers (Coleman, 1997). In bone metastasis, there is a vicious cycle in the osseous microenvironment, whereby bi-directional interactions between tumor cells and osteoclasts lead to both bone loss and tumor growth (Chirgwin and Guise, 2000; Ell and Kang, 2012). Osteoclast inhibitors, such as bisphosphonates and RANKL neutralizing antibody (denosumab), can interrupt this vicious cycle, thus reducing bone lesions, tumor burden, bone pain and mortality (Coleman, 2012; Mundy, 2002; Roodman, 2004). However, these drugs exhibit limitations such as moderate efficacy or high cost, as well as side effects including osteonecrosis of the jaw and renal toxicity (Brown and Coleman, 2012; Coleman, 2012; Khosla et al., 2007). Therefore, identification of novel suppressors of osteoclastogenesis will not only enhance the fundamental understanding of skeletal physiology but also facilitate the development of better therapies to prevent and treat multiple bone and cancer diseases.

MicroRNAs (miRNAs) have attracted considerable attention because of their important roles in development and physiology, as well as diseases such as cancer. They are small molecules that inhibit the stability and translation of multiple target messenger RNAs (mRNA). Recent studies have identified specific miRNAs as tumor suppressors or oncogenes for which loss- or gain-of-function contributes to malignancy (Chivukula and Mendell, 2008; Kato and Slack, 2008; Ventura and Jacks, 2009). Importantly, latest development of miRNA-based interventions such as miRNA mimetics or antagomirs in combination with novel nanoparticle, atelocollagen or lipid-mediated miRNA delivery systems has highlighted their tremendous therapeutic potential (Kasinski and Slack, 2011; Osaki et al., 2011; Pramanik et al., 2011; Takeshita et al., 2010; Trang et al., 2011). Nonetheless, how miRNAs regulate osteoclastogenesis, bone resorption and the bone metastatic niche is a provocative question that is still underexplored.

SUMMARY OF THE INVENTION

Thus, in accordance with the present invention, there is provided a method of increasing bone mass and/or volume in a subject comprising (a) identifying a patient in need of increased bone mass and/or volume; and (b) administering to said subject an agonist of miR-34a, wherein said subject does not have cancer. The agonist may be miR-34a or an expression vector that expresses miR-34a. The agonist may be formulated with a nanoparticle delivery vehicle. The agonist may be administered to said subject systemically, such as intravenously, intra-peritoneally, intramuscularly, subcutaneously or topically. The agonist may be administered to a bone target site, such as via injection at said site, or in a time-release device implanted at said site. The subject may be human or a non-human animal, such as a mouse, a rat, a rabbit, a dog, a cat, a horse, a monkey or a cow. The method may further comprise at least a second administration of said agonist, including where said subject receives three administrations per week. The subject may receive at least 12 administrations. The method may further comprise assessing bone mass following administration of said agonist, such as by bone imaging. The subject may suffer from osteoporosis, bone fracture, bone loss due to trauma, rheumatoid arthritis or Paget's Disease. The miR-34a may contain at least one non-natural base.

In another embodiment, there is provided a method of increasing bone growth in a subject comprising administering to said subject an agonist of miR-34a. The agonist may be miR-34a or an expression vector that expresses miR-34a. The agonist may be formulated with a nanoparticle delivery vehicle. The agonist may be administered to said subject systemically, such as intravenously, intra-peritoneally, intramuscularly, subcutaneously or topically. The agonist may be administered to a bone target site, such as via injection at said site, or in a time-release device implanted at said site. The subject may be human or a non-human animal, such as a mouse, a rat, a rabbit, a dog, a cat, a horse, a monkey or a cow. The miR-34a may contain at least one non-natural base. The method may further comprise at least a second administration of said agonist, including where said subject receives three administrations per week. The subject may receive at least 12 administrations. The method may further comprise assessing bone mass following administration of said agonist, such as by bone imaging.

Also provided is a method of increasing osteoblast number in a subject comprising (a) identifying a patient in need of increased osteoblast number; and (b) administering to said subject an agonist of miR-34a, wherein said subject does not have cancer.

Another embodiment involves method of decreasing osteoclast number in a subject comprising (a) identifying a patient in need of decreased osteoclast number; and (b) administering to said subject an agonist of miR-34a, wherein said subject does not have cancer.

A method of increasing bone strength in a subject comprising (a) identifying a patient in need of increased bone strength; and (b) administering to said subject an agonist of miR-34a, wherein said subject does not have cancer.

The use of the word "a" or "an" when used in conjunction with the term "comprising" in the claims and/or the specification may mean "one," but it is also consistent with the meaning of "one or more," "at least one," and "one or more than one."

It is contemplated that any embodiment discussed herein can be implemented with respect to any method or composition of the invention, and vice versa. Furthermore, compositions and kits of the invention can be used to achieve methods of the invention.

Throughout this application, the term "about" is used to indicate that a value includes the standard deviation of error for the device or method being employed to determine the value.

The use of the term "or" in the claims is used to mean "and/or" unless explicitly indicated to refer to alternatives only or the alternatives are mutually exclusive, although the disclosure supports a definition that refers to only alternatives and "and/or."

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

Other objects, features and advantages of the present invention will become apparent from the following detailed description. It should be understood, however, that the detailed description and the specific examples, while indicating specific embodiments of the invention, are given by way of illustration only, since various changes and modifications within the spirit and scope of the invention will become apparent to those skilled in the art from this detailed description.

BRIEF DESCRIPTION OF THE DRAWINGS

The invention may be better understood by reference to one or more of these drawings in combination with the detailed description of specific embodiments presented herein.

FIGS. 1A-J. miR-34a Suppresses Osteoclastogenesis Ex Vivo. (FIG. 1A) A diagram of bone marrow osteoclast differentiation assay. Rosi, rosiglitazone. (FIGS. 1B-D) TRAP expression (FIG. 1B) and mature miRNA levels (FIGS. 1C-D) (n=3). (FIGS. 1E-F) Osteoclast differentiation was decreased by pre-miR-34a (FIG. 1E) but increased by anti-miR-34a (FIG. 1F) (n=3). Left, mature miR-34a levels; Right, TRAP expression; Bottom, images of TRAP-stained cultures; mature osteoclast numbers (black) and resorptive activity (blue). Scale bar, 25 µm. R, RANKL. (FIGS. 1G-J) Human RANKL-mediated osteoclast differentiation from human peripheral blood mononuclear (hPBMN) cells (n=4). (FIG. 1G) Mature miR-34a levels. (FIG. 1H) TRAP expression. (FIG. 1I) Mature osteoclast numbers. (FIG. 1J) TRAP-staining and resorptive activity. Scale bar, 25 µm. Error bars, SD.

FIGS. 2A-M. miR-34a Inhibits Bone Resorption and Increases Bone Mass In Vivo. (FIG. 2A) A diagram of the conditional miR-34a transgene (CAG-34a). (FIG. 2B) 34a-Tie2-Tg cultures showed decreased osteoclast differentiation (n=3). Left, miR-34a levels; Middle, TRAP expression; Right, TRAP staining, osteoclast numbers (black) and resorptive activity (blue). Scale bar, 25 µm. (FIG. 2C) Serum CTX-1 (2-month-old, male, n=5). (FIGS. 2D-F) µCT of the tibiae (2-month-old, male, n=4). (FIG. 2D) Images of the trabecular bone of the tibial metaphysis (top) (scale bar, 10 µm) and the entire proximal tibia (bottom) (scale bar, 1 mm) (FIG. 2E) Trabecular bone parameters. BV/TV, bone volume/tissue volume ratio; BS/BV, bone surface/bone volume ratio; Tb.Th, trabecular thickness; Tb.Sp, trabecular separation; Conn.D., connectivity density; SMI, structure model index. (FIG. 2F) Cortical BV/TV. (FIG. 2G) A diagram of miR-34a gene-trap knockout. (FIG. 2H) 34a-KO and 34a-Het cultures showed enhanced osteoclast differentiation (n=3). (FIG. 2I) Serum CTX-1 (2-month-old, male, n=6). (FIGS. 2J-L) nCT of the tibiae (2-month-old, male, n=4). (FIG. 2J) Images. (FIG. 2K) Trabecular bone parameters. (FIG. 2L) Cortical BV/TV. (FIG. 2M) Serum P1NP (2-month-old, male, n=6). Error bars, SD.

FIGS. 3A-S. miR-34a Attenuates Osteoporosis and Cancer Bone Metastases. (FIGS. 3A-F) OVX or sham operation was performed on 10-week-old female mice. Three days post-surgery, the OVX mice were treated with miR-34a-CH (34a) or miR-Ctrl-CH (Ctrl) at 5 µg/mouse twice/week for 5 weeks (n=5). (FIG. 3A) Uterine weight. (FIG. 3B) Body weight. (FIG. 3C) Serum CTX-1. (FIG. 3D) Serum P1NP. (FIG. 3E) µCT images. (FIG. 3F) Trabecular bone parameters. (FIG. 3G) miR-34a levels in each tissue from miR-34a-CH-vs. miR-Ctrl-CH-treated mice 72 hrs after a single injection (n=3). Top, mature miR-34a levels; Bottom, fold induction. (FIGS. 3H-K) 34a-Tie2-Tg mice or controls (3-month-old, female, n=7) were subjected to OVX and analyzed 5 weeks post-surgery. (FIG. 3H) Uterine weight. (FIG. 3I) Serum CTX-1. (FIG. 3J) Serum P1NP. (FIG. 3K) BV/TV by µCT. (FIG. 3L) Xenograft of MDA231-BoM-1833 cells into 34a-Tie2-Tg (n=8) or control (n=9). (FIG. 3M) Allograft of B16-F10 cells into 34a-Tie2-Tg (n=4) or control (n=6). (FIG. 3N) MDA231-BoM-1833 cells in 34a-KO (n=6), 34a-Het (n=6) or control (n=6). (FIG. 3O) B16-F10 in 34a-KO (n=6), 34a-Het (n=4) or control (n=6). (FIGS. 3P-R) Bone metastasis of MDA231-BoM-1833 cells was attenuated by miR-34a-CH delivered 3 days post-xenograft at 10 µg/mouse twice/week for 5 weeks (n=5). (FIG. 3P) BLI signal. (FIG. 3Q) Left, BLI images; Right, bone metastases number and size. (FIG. 3R) X-ray images and histology images for TRAP and ALP (alkaline phosphatase) staining. Arrows indicate osteolytic lesions. (FIG. 3S) Bone metastasis of B16-F10 cells was attenuated by miR-34a-CH delivered at 5 µg/mouse twice/week for 4 weeks starting 1 week before cancer cell injection (n=8). (FIGS. 3L-S) Statistical analyses were performed with Mann Whitney Test and are shown as mean±SD with p value illustrated. a, c, d, f, h-k, l, n, o, p p<0.05 by ANOVA.

FIGS. 4A-S. Tgif2 is an Essential miR-34a Direct Target and a Pro-Osteoclastogenic Factor. (FIG. 4A) Tgif2 expression was inhibited by pre-miR-34a in osteoclast cultures (n=3). (FIG. 4B) Tgif2 expression in WT and 34a-PT-Tg osteoclast cultures (n=3). (FIG. 4C) Sequence alignment of the Tgif2 3'UTR. (FIG. 4D) A diagram of Tgif2 3'UTR reporters. (FIG. 4E) Luciferase readout from WT or mutant Tgif2 3'UTR reporter co-transfected in HEK293 cells with pre-miR-34a or anti-miR-34a (n=3). (FIGS. 4F-H) Comparison of Tgif2-KO, Tgif2-Het and WT control mice (1.5-month-old, male, n=7). (FIG. 4F) Serum CTX-1. (FIGS. 4G-H) μCT of tibiae. (FIG. 4G) Trabecular BV/TV. (FIG. 4H) Images of the trabecular bone of the tibial metaphysis (scale bar, 10 μm). (FIG. 4I) Decreased osteoclast differentiation in Tgif2-KO and Tgif2-Het cultures (n=3). (FIG. 4J) Tgif2-KO cultures were resistant to the anti-osteoclastogenic effects of pre-miR-34a (n=3). (FIGS. 4I-J) Top, TRAP expression; Bottom, TRAP staining, osteoclast number (black) and resorptive activity (blue). (FIGS. 4K-L) Tgif2/34a double knockout (DKO) mice were compared with WT, Tgif2-KO or 34a-KO (2-month-old, male, n=4). (FIG. 4K) Osteoclast differentiation. (FIG. 4L) Serum CTX-1. (FIG. 4M) Tgif2 mRNA in RAW264.7 cells following transfection of transcription factors (n=3). (FIG. 4N) ChIP of transcription factor binding and H3K4me3 levels at the endogenous Tgif2 promoter in RAW264.7 cells 3d after RANKL treatment (n=6); txn, transcription. (FIG. 4O) Transcription factor was co-transfected into 293 cells with its luciferase reporter, together with Tgif2 or a GFP control (n=6). (FIG. 4P) Luciferase reporter was transfected into WT, Tgif2-KO or 34a-KO osteoclast cultures (n=6). (FIGS. 4Q-R) NFATc1 mRNA (FIG. 4Q, n=3), c-Jun phosphorylation and IκBα degradation (FIG. 4R) in WT, Tgif2-KO or 34a-KO osteoclast cultures. Ratios of p-c-Jun/total-c-Jun and IκBα/β-actin are shown. (FIG. 4S) A model for how miR-34a suppresses osteoclastogenesis. Error bars, SD.

FIGS. 5A-I. Additional analyses of 34a-Tie2-Tg mice. (FIGS. 5A-C) Further characterization of the transgene expression in 34a-Tie2-Tg mice. (FIG. 5A) FACS analysis of the percentage of $GFP^+$ bone marrow osteoclast progenitors ($c-Fms^+RANK^+$) in 34a-Tie2-Tg mice and "transgene only, no cre" control (n=3). (FIG. 5B) Images showing GFP and LacZ expression in osteoclast progenitors from 34a-Tie2-Tg mice ($GFP^+LacZ^-$) and "transgene only, no cre" control mice ($GFP^-LacZ^+$). Scale bar, 100 μm. (FIG. 5C) Northern blot analysis confirmed miR-34a over-expression in the hematopoietic bone marrow cells of 34a-Tie2-Tg mice. Ct, control; Tg, 34a-Tie2-Tg; EtBr, ethidium bromide. (FIG. 5D) QPCR analysis of mRNA expression of additional osteoclast marker genes (n=3). (FIG. 5E) Osteoclast function analysis. Bone marrow osteoclast differentiation was conducted in OsteoAssay bone plates (Lonza), and osteoclast activity was quantified as calcium release using CalciFluo ELISA assay (Lonza) (n=8, mean±s.e.). (FIG. 5F) Osteoclast proliferation was not affected, quantified by BrdU incorporation (n=6). (FIG. 5G) Osteoclast apoptosis was not affected, quantified by FACS analysis of $AnnexinV^+7-AAD^-$ cells (n=6). (FIGS. 5H-I) Static and dynamic histomorphometry. (FIG. 5H) Representative images of distal femur sections (2 month old, male). Scale bars, 1 mm for Von Kossa images; 10 μm for TRAP, ALP and Calcein images. (FIG. 5I) Quantification of parameters at distal femur and vertebrae in 2-month-old male and female mice.

FIGS. 6A-D. Effects of miR-34a over-expression using additional cre driver targeting osteoclast progenitors. 34a-PT-Tg mice were generated using PPARγ-tTA-TRE-cre driver. (FIG. 6A) Bone marrow osteoclast differentiation assays. Left, mature miR-34a level (n=3); middle, TRAP mRNA expression (n=3); right, TRAP staining of differentiation cultures, quantification of mature osteoclast numbers per well in 24-well plates (black, n=3), and quantification of bone resorptive activity by calcium release from bone plate into culture medium (μM) (blue, n=6). (FIG. 6B) Serum CTX-1 bone resorption marker (2-month-old males, n=10). (FIG. 6C) μCT analysis of the trabecular bone in proximal tibiae (2-month-old males, n=4). (FIG. 6D) Histomorphometry of the distal femur and vertebrae in 2-month-old mice.

FIGS. 7A-H. Effects of miR-34a over-expression using additional osteoclastic cre drivers. (FIGS. 7A-D) 34a-Lys-Tg mice were generated using Lysozyme-cre driver. (FIGS. 7E-H) 34a-Ctsk-Tg mice were generated using Ctsk-cre driver. (FIGS. 7A and 7E) Bone marrow osteoclast differentiation assays. Left, mature miR-34a level (n=3); middle, TRAP mRNA expression (n=3); right, TRAP staining of differentiation cultures, quantification of mature osteoclast numbers per well in 24-well plates (black, n=3), and quantification of bone resorptive activity by calcium release from bone plate into culture medium (μM) (blue, n=6). (FIGS. 7B and 7F) Serum CTX-1 (2-month-old males; FIG. 7B, n=5; FIG. 7F, n=8). (FIGS. 7C and 7G) Trabecular BV/TV of proximal tibiae by μCT (2-month-old males; FIG. 7C, n=4; FIG. 7G, n=4). (FIGS. 7D and 7H) Histomorphometry of the distal femur and vertebrae in 2-month-old mice.

FIGS. 8A-H. Additional analyses of gene-trap miR-34a knockout mice. (FIG. 8A) Northern blot analysis confirmed decreased miR-34a expression in the miR-34a gene trap KO mice. Six-week-old female mice with corresponding genotypes were irradiated with a dose of 6 Gy, and 4 h later the spleen was collected for RNA extraction. Northern blotting for miR-34a was performed as described (Chang T C et al. 2008, Nature Genetics 40:43-50). (FIG. 8B) QPCR analysis of mRNA expression of additional osteoclast marker genes (n=3). (FIG. 8C) Osteoclast function analysis. Bone marrow osteoclast differentiation was conducted in OsteoAssay bone plates (Lonza), and osteoclast activity was quantified as calcium release using CalciFluo ELISA assay (Lonza) (n=8, mean±s.e.). (FIG. 8D) Osteoclast proliferation was not affected, quantified by BrdU incorporation (n=6). (FIG. 8E) Osteoclast apoptosis was not affected, quantified by FACS analysis of $AnnexinV^+7-AAD^-$ cells (n=6). (FIG. 8F) WT mice transplanted with 34a-KO bone marrow cells exhibited higher serum CTX-1 levels compared to WT mice transplanted with WT bone marrow cells (n=5 recipients per group). (FIGS. 8G-H) Static and dynamic histomorphometry. (FIG. 8G) Representative images of distal femur sections (2 month old, male). Scale bars, 1 mm for Von Kossa images; 10 μm for TRAP, ALP and Calcein images. (FIG. 8H) Quantification of parameters at distal femur and vertebrae in 2-month-old male and female mice.

FIGS. 9A-N. Effects of targeted miR-34a deletion. (FIG. 9A-D) Targeted miR-34a/b/c triple KO (34abc-TKO) mice were compared with WT control mice (5 month males, n=4). (FIGS. 9A-C) Bone marrow osteoclast differentiation assay. (FIG. 9A) Expression of miR-34a was diminished while expression of miR-34b and miR-34c remained absent/low in osteoclast precursors on d3. (FIG. 9B) Expression of osteoclast markers were increased. (FIG. 9C) Number, size and resorptive activity of mature osteoclasts were increased. (FIG. 9D) Serum CTX-1 was increased. (FIGS. 9AE-H) Targeted full miR-34a KO (34a-full-KO) mice were compared with WT control mice (2 month females, n=3). (FIGS. 9E-G) Bone marrow osteoclast differentiation assay. (FIG. 9E) Expression of miR-34a was diminished in osteoclast precursors on d3. (FIG. 9F) Expression of osteoclast markers were increased. (FIG. 9G) Number, size and resorptive activity of mature osteoclasts were increased. (FIG. 9H) Serum CTX-1 was increased. (FIGS. 9I-N) Conditional miR-34a KO mice by Tie2-cre (34a-Tie2-KO) were compared with littermate miR-34af/f control mice (2 month males, n=6). (FIGS. 9I-K) Bone marrow osteoclast differentiation assay. (FIG. 9I) miR-34a expression was reduced in osteoclast precursors on d3. (FIG. 9J) Expression of osteoclast markers were increased. (FIG. 9K) Number, size and resorptive activity of mature osteoclasts were increased. (FIG. 9L) Serum CTX-1 was increased. (FIG. 9M) Trabecular BV/TV of proximal tibiae by μCT. (FIG. 9N) Histomorphometry of the distal femur and vertebrae. For FIGS. 9C, 9G and 9K, Mature osteoclasts were identified as multinucleated (>3 nuclei) TRAP+ (purple) cells. Scale bar, 25 μm. Quantification of osteoclast number/well is shown in black. Quantification of osteoclast resorptive activity by calcium release from bone to culture medium (μM) is shown in blue.

FIGS. 10A-E. Anti-osteoporosis effects of miR-34a. (FIG. 10A) Histomorphometry of the distal femur and vertebrae in OVX mice treated with miR-34a-CH nanoparticles. OVX or sham operation was performed on 10-week-old WT female C57BL/6J mice. Three days post surgery, the OVX mice were intravenously injected with miR-34a-CH (34a) or miR-Ctrl-CH (Ctrl) at 5 μg/mouse twice a week for 5 weeks (n=5). (FIGS. 10B-D) Osteoprotective effects of miR-34a-CH in sham control mice. WT female C57B/6J mice (n=5, 10 week old) were subjected to sham operation and then treated with miR-34a-CH or miR-34a-Ctrl at 5 μg/mouse twice a week for 5 weeks. (FIG. 10B) Serum CTX-1. (FIG. 10C) Serum P1NP. (FIG. 10D) BV/TV of proximal tibiae by μCT. (FIG. 10E) Histomorphometry of the distal femur and vertebrae in WT and 34a-Tie2-Tg mice after OVX. 34a-Tie2-Tg mice or controls (3-month-old, female, n=7) were subjected to OVX or sham operation and analyzed 5 weeks post-surgery.

FIGS. 11A-F. Additional characterization of bone metastases. (FIG. 11A) Representative BLI images. (FIG. 11B) Quantification of the number of metastasis. (FIG. 11C) Quantification of the size of metastasis. For FIGS. 10A-C, n=9 for Ctrl, n=8 for 34a-Tie2-Tg, n=6 for WT and 34a-KO; results are shown as average±s.e. (FIG. 11D) Xenograft of MDA231-BoM-1833 human breast cancer cells into 34a-Tie2-Tg nude mice (n=8) or littermate control nude mice (n=9). Results from each week are shown separately to better visualize the difference. (FIG. 11E) Xenograft of MDA231-BoM-1833 human breast cancer cells into 34a-PT-Tg nude mice (n=8) or littermate control nude mice (n=8). Results from each week are shown separately to better visualize the difference. (FIG. 11F) Allograft of B16-F10 mouse melanoma cells into 34a-PT-Tg (n=7) or littermate control mice (n=7).

FIGS. 12A-E. Effects of miR-34a on cancer cells. a, Systemic miR-34a-CH delivery did not affect the growth of B16-F10 melanoma cells injected subcutaneously (n=5, male, 8 week old). Tumors were collected 18 days after cell injection, result is shown as average±s.e. b, Systemic miR-34a-CH delivery did not affect cancer metastasis to other organs such as lung (n=5, male, 8 week old). B16-F10 cells were i.v. injected retro-orbitally, BLI signals were quantified 2 weeks later and the result is shown as average±s.e. c-d, MiR-34a-CH treatment of cancer cell alone was not sufficient to inhibit bone metastasis. BoM-1833 cells were treated with miR-34a-CH or miR-Ctrl-CH in cultures for 24 hrs before cardiac injection (n=5, male, 6 week old), and the mice were not treated with nanoparticles. c, Quantification of bone metastasis BLI signal 5 weeks after injection, shown as average±s.e. d, MiR-34a over-expression in BoM-1833 cells persisted for 5 weeks in cultures. e, Loss-of-function in 34a-KO and 34a-Het mice did not result in significantly increased susceptibility of cancer and mortality. Left, Kaplan-Meier survival curve for WT (n=29), 34a-Het (n=35) and 34a-KO (n=29); p=0.223 by log-Rank (Mantel-Cox) test. Right, the 34a-KO allele was transmitted at normal Mendelian frequency.

FIGS. 13A-I. Osteoblastic miR-34a over-expression is not sufficient to inhibit osteoporosis or bone metastases. (FIG. 13A) A schematic diagram of the ex vivo bone marrow osteoblast differentiation assay. MSC GF, mesenchymal stem cell growth factors; GP, β-glycerophosphate; AA, ascorbic acid. (FIG. 13B) Osteoblast differentiation was decreased for bone marrow from 34a-KO and 34a-Het mice compared to WT controls, quantified by osteoblast marker genes osteocalcin and Col1a1 on day 13 (n=6). (FIGS. 13C-H), Characterization of osteoblastic miR-34a transgenic mice. CAG34a mice were bred with Osterix-CreER mice to generate miR34a-Osx-transgenic (34a-Osx-Tg) mice or littermate control mice that carry only CAG34a transgene; all mice (1-month-old, male) received tamoxifen injection on two consecutive days and analyzed 2 months later. (FIG. 13C) Elevated levels of mature miR-34a in 34a-Osx-Tg osteoblast differentiation cultures on day 13 (n=6). (FIG. 13D) Osteoblast differentiation was increased for bone marrow from 34a-Osx-Tg mice compared to control mice, quantified by osteoblast marker genes osteocalcin and Col1a1 on day 13 (n=6). (FIG. 13E) Serum P1NP was increased in 34a-Osx-Tg mice (n=6). (FIG. 13F) Serum CTX-1 was unaltered in 34a-Osx-Tg mice (n=6). (FIG. 13G) Histomorphometry of distal femur and vertebrae in 34a-Osx-Tg and control mice. (FIG. 13H) OVX-induced bone resorption and bone loss was unaltered in 34a-Osx-Tg mice. 34a-Osx-Tg mice or controls (3-month-old and 2 months after tamoxifen injection, female, n=5) were subjected to OVX or sham operation and analyzed 5 weeks post-surgery. (FIG. 13I) Cancer bone metastasis was unaltered in 34a-Osx-Tg mice (n=8). Statistical analyses in FIG. 13I were performed with Mann Whitney Test and are shown as mean±standard error.

FIGS. 14A-F. Additional characterization of Tgif2 as a key miR-34a direct target gene. (FIG. 14A) A list of potential miR-34a target genes in the osteoclast lineage and characterization of miR-34a regulation. N.D., not determined (FIG. 14B) Fold changes in the expression of each candidate target gene after transfection with pre-miR-34a vs. pre-miR-ctrl in WT bone marrow osteoclast differentiation culture (n=3). (FIG. 14C) Fold changes in the luciferase readout from 3'UTR reporter for each candidate target gene co-transfected in HEK293 cells with pre-miR-34a or pre-control. The results were normalized by internal control β-galactosidase (β-gal) readout (n=3). (FIG. 14D) Western blot analysis showing that Tgif2 protein expression is decreased in the bone marrow osteoclast progenitors from 34a-Tie2-Tg transgenic mice compared with control mice (left), but increased in the bone marrow osteoclast progenitors from 34a-KO and 34a-Het mice compared with WT control mice (right). (FIG. 14E) Human Tgif2 expression in hPBMN osteoclast differentiation cultures was suppressed by pre-miR-34a but enhanced by anti-miR-34a via transfection (n=4). (FIG. 14F) Histomorphometry of the distal femur and vertebrae in 1.5 month old Tgif2-KO, Tgif2-Het and WT control mice.

DETAILED DESCRIPTION OF ILLUSTRATIVE EMBODIMENTS

Over 200 million people worldwide suffer from bone disorders such as osteoporosis, bone fractures, and periodontal (gum) disease (where the teeth loose surrounding bone). Osteoporosis represents a large and rapidly growing health care problem with an unmet medical need for therapies that stimulate bone formation. Most current drugs for osteoporosis retard bone degradation but do not stimulate bone formation to replace already lost bone. Compounds that stimulate bone formation thus represent an unmet need in the area of bone disease. Osteoporosis is known to affect approximately 100 million people worldwide—35 million of whom live in the U.S., Western Europe and Japan. Moreover, over 25 million individuals suffer bone fractures yearly, 60 million have periodontal disease (in which the tooth loosens from the jaw bone), and another 18 million have other bone disorders such as bone cancer.

Most current therapies for osteoporosis patients focus on prevention of bone loss, not bone formation. This remains an important consideration as significant morbidity and mortality are associated with prolonged bed rest in the elderly that occur post-bone fracture, particularly those who have suffered hip fractures. Complications of bed rest include blood clots and pneumonia. These complications are recognized and measures are usually taken to avoid them, but these are hardly the best approach to therapy.

Yet another bone-related health issues is bone reconstruction and, specifically, the ability to reconstruct defects in bone tissue that result from traumatic injury, as a consequence of cancer or cancer surgery, as a result of a birth defect, or as a result of aging. There is a significant need for more frequent orthopedic implants, and cranial and facial bone are particular targets for this type of reconstructive need. The availability of new implant materials, e.g., titanium, has permitted the repair of relatively large defects. Titanium implants provide excellent temporary stability across bony defects. However, experience has shown that a lack of viable bone bridging the defect can result in exposure of the appliance, infection, structural instability and, ultimately, failure to repair the defect.

Autologous bone grafts are another possibility to deal with bone injury, but they have several demonstrated disadvantages in that they must be harvested from a donor site such as iliac crest or rib, they usually provide insufficient bone to completely fill the defect, and the bone that does form is sometimes prone to infection and resorption. Partially purified xenogeneic preparations are not practical for clinical use because microgram quantities are purified from kilograms of bovine bone, making large scale commercial production both costly and impractical. Allografts and demineralized bone preparations are therefore often employed. Microsurgical transfers of free bone grafts with attached soft tissue and blood vessels can close bony defects and allow an immediate source of blood supply to the graft. However, these techniques are time consuming, have been shown to produce a great deal of morbidity, and can only be used by specially trained individuals.

Another form of bone disease is that resulting from cancer. A number of cancers metastasize to bone and can result in bone weakening, and some are even associated with bone destruction and bone loss, such as breast, lung, thyroid, kidney and prostate cancer. In addition, Multiple Myeloma and its associated myeloma bone disease (MBD) is not a metastatic cancer. Rather, myeloma cells are derived from the B-cells of the immune system that normally reside in the bone marrow and are therefore intimately associated with bone. Indeed, the bone marrow microenvironment plays an important role in the growth, survival and resistance to chemotherapy of the myeloma cells, which, in turn, regulate the increased bone loss associated with this disorder. Over 90% of myeloma patients have bone involvement, versus 40-60% of cancer patients who have bone metastasis, and over 80% of these MBD patients have intractable bone pain. Additionally, approximately 30% of myeloma patients have hypercalcemia that is a result of the increased osteolytic activity associated with this disease.

Unlike the osteolysis associated with other bone tumors, the MBD lesions are unique in that they do not heal or repair, despite the patients' having many years of complete remission. Mechanistically, this seems to be related to the inhibition and/or loss of the bone-forming osteoblast during disease progression. Indeed, bone marker studies and histomorphometry indicate that both the bone-resorbing osteoclast and osteoblast activity are increased, but balanced early in the disease, whereas overt MBD shows high osteoclast activity and low osteoblast activity. Thus, MBD is a disorder in which bone formation and bone loss are uncoupled and would benefit from therapies that both stimulate bone formation and retard its loss.

To date generally applicable and successful therapies for these types of diseases do not exist. Therefore, there continues to be a need for improved methods of stimulating bone formation and increasing bone strength in vivo to treat bone disease and injury, including cancer. In this study, the inventor identifies miR-34a as a novel yet critical suppressor of bone resorption as well as an enhancer of bone formation, and demonstrates that miR-34a confers protection against osteoporosis and cancer bone metastasis. Agonists of miR-34a are proposed as therapeutic agents for bone-loss disease and disorders. This and other aspects of the disclosure are described in detail below.

I. Bone Structure and Physiology

Bone is a living, growing tissue. It is porous and mineralized, and made up of cells, vessels, organic matrix and inorganic hydroxyapatite crystals. The human skeleton is actually made up of 2 types of bones: the cortical bone and the trabecular bone. Cortical bone represents nearly 80% of the skeletal mass. Cortical bone has a slow turnover rate and a high resistance to bending and torsion. It provides strength where bending would be undesirable as in the middle of long bones. Trabecular bone only represents 20% of the skeletal mass, but 80% of the bone surface. It is less dense, more elastic and has a higher turnover rate than cortical bone.

A. Bone Forming Cells

Osteoprogenitors.

Human bone precursor cells are characterized as small-sized cells that express low amounts of bone proteins (osteocalcin, osteonectin, and alkaline phosphatase) and have a low degree of internal complexity (Long et al., 1995). When stimulated to differentiate, these preosteoblast cells become osteoblast in their appearance, size, antigenic expression, and internal structure. Although these cells are normally present at very low frequencies in bone marrow, a process for isolating these cells has been described (Long et al., 1995). U.S. Pat. No. 5,972,703 further describes methods of isolating and using bone precursor cells, and is specifically incorporated herein by reference.

A number of studies indicate that bone marrow derived cells have osteogenic potential. The majority of these investigations point to mesenchymal stem cells (MSC) as undergoing differentiation into osteoblasts when cultured in the presence of bone-active cytokines (Jaiswal et al., 2000; Phinney et al., 1999; Aubin, 1998; Zohar et al., 1997). Mesenchymal stem cells are a pluripotent population capable of generating multiple stromal cell lineages. MSC, as currently used, are a heterogeneous population of cells isolated by plastic adherence, and propagated by low-density passage. Nonetheless, a recent publication indicates the clonal nature of cell fate outcomes in MSC indicating that a single MSC cell can give rise to two or three mesenchymal lineages one of which is usually bone cells (Pittenger et al., 1999). These studies are consistent with earlier reports that demonstrated the osteogenic potential of bone marrow stromal cells, in particular the so-called CFU-f from both mice and human (Friedenstein et al., 1968; Reddi and Huggins, 1972; Friedenstein et al., 1982; Ashton et al., 1985; Bleiberg, 1985; Gronthos et al., 1994; Gronthos et al., 1999).

Single-cell isolation of human MSC generated clones that express the same surface phenotype as unfractionated MSC (Pittenger et al., 1999). Interestingly, of the 6 MSC clones evaluated, 2 retained osteogenic, chrondrogenic and adipogenic potential; others were bipotent (either osteo-plus chondrogenic potential, or osteo-adipocytic potential) or were uni-lineage (chondrocyte). This suggests that MSC themselves are heterogeneous in nature (although culture conditions also may have led to loss of lineage potential). To date, the self-renewal capacity of MSC remains in question. Nonetheless, these in vitro studies and other in vivo studies (Kadiyala et al., 1997; Petite et al., 2000; Krebsbach et al., 1999) show that MSC can commit to the bone cell lineage and develop to the state of matrix mineralization in vitro, or bone formation in vivo.

Preosteoblasts.

Preosteoblasts are intermediate between osteoprogenitor cells and osteoblasts. They show increasing expression of bone phenotypic markers such as alkaline phosphatase (Kale et al., 2000). They have a more limited proliferative capacity, but nonetheless continue to divide and produce more preosteoblasts or osteoblasts.

Osteoblasts.

An osteoblast is a mononucleate cell that is responsible for bone formation. Osteoblasts produce osteoid, which is composed mainly of Type I collagen. Osteoblasts are also responsible for mineralization of the osteoid matrix. Bone is a dynamic tissue that is constantly being reshaped by osteoblasts, which build bone, and osteoclasts, which resorb bone. Osteoblast cells tend to decrease in number and activity as individuals become elderly, thus decreasing the natural renovation of the bone tissue.

Osteoblasts arise from osteoprogenitor cells located in the periosteum and the bone marrow. Osteoprogenitors are immature progenitor cells that express the master regulatory transcription factor Cbfa1/Runx2. Osteoprogenitors are induced to differentiate under the influence of growth factors, in particular the bone morphogenetic proteins (BMPs). Aside from BMPs, other growth factors including fibroblast growth factor (FGF), platelet-derived growth factor (PDGF), transforming growth factor β (TGF-β) may promote the division of osteoprogenitors and potentially increase osteogenesis. Once osteoprogenitors start to differentiate into osteoblasts, they begin to express a range of genetic markers including Osterix, Col1, ALP, osteocalcin, osteopontin, and osteonectin. Although the term osteoblast implies an immature cell type, osteoblasts are in fact the mature bone cells entirely responsible for generating bone tissue in animals and humans.

Osteoclasts.

An osteoclast is a type of bone cell that removes bone tissue by removing its mineralized matrix. This process is known as bone resorption. Osteoclasts and osteoblasts are instrumental in controlling the amount of bone tissue: osteoblasts form bone, osteoclasts resorb bone. Osteoclasts are formed by the fusion of cells of the monocyte-macrophage cell lineage. Osteoclasts are characterized by high expression of tartrate resistant acid phosphatase (TRAP) and cathepsin K.

Osteoclast formation requires the presence of RANK ligand (receptor activator of nuclear factor κβ) and M-CSF (Macrophage colony-stimulating factor). These membrane bound proteins are produced by neighbouring stromal cells and osteoblasts; thus requiring direct contact between these cells and osteoclast precursors. M-CSF acts through its receptor on the osteoclast, c-fms (colony stimulating factor 1 receptor), a transmembrane tyrosine kinase-receptor, leading to secondary messenger activation of tyrosine kinase Src. Both of these molecules are necessary for osteoclastogenesis and are widely involved in the differentiation of monocyte/macrophage derived cells. RANKL is a member of the tumor necrosis family (TNF), and is essential in osteoclastogenesis. RANKL knockout mice exhibit a phenotype of osteopetrosis and defects of tooth eruption, along with an absence or deficiency of osteoclasts. RANKL activates NF-κβ (nuclear factor-κβ) and NFATc1 (nuclear factor of activated t cells, cytoplasmic, calcineurin-dependent 1) through RANK. NF-κβ activation is stimulated almost immediately after RANKL-RANK interaction occurs, and is not upregulated. NFATc1 stimulation, however, begins ~24-48 hours after binding occurs and its expression has been shown to be RANKL dependent. Osteoclast differentiation is inhibited by osteoprotegerin (OPG), which binds to RANKL thereby preventing interaction with RANK.

B. Bone Formation

The formation of bone during the fetal stage of development occurs by two processes: intramembranous ossification and endochondral ossification. Intramembranous ossification mainly occurs during formation of the flat bones of the skull; the bone is formed from mesenchyme tissue. The steps in intramembranous ossification are development of ossification center, calcification, formation of trabeculae and development of periosteum. Endochondral ossification, on the other hand, occurs in long bones, such as limbs; the bone is formed around a cartilage template. The steps in endochondral ossification are development of cartilage model, growth of cartilage model, development of the primary ossification center and development of the secondary ossification center.

Endochondral ossification begins with points in the cartilage called "primary ossification centers." They mostly appear during fetal development, though a few short bones begin their primary ossification after birth. They are responsible for the formation of the diaphyses of long bones, short bones and certain parts of irregular bones. Secondary ossification occurs after birth, and forms the epiphyses of long bones and the extremities of irregular and flat bones. The diaphysis and both epiphyses of a long bone are separated by a growing zone of cartilage (the epiphyseal plate). When the child reaches skeletal maturity (18 to 25 years of age), all of the cartilage is replaced by bone, fusing the diaphysis and both epiphyses together (epiphyseal closure).

Remodeling or bone turnover is the process of resorption followed by replacement of bone with little change in shape and occurs throughout a person's life. Osteoblasts and osteoclasts, coupled together via paracrine cell signalling, are referred to as bone remodeling units. The purpose of remodeling is to regulate calcium homeostasis, repair microdamaged bones (from everyday stress) but also to shape and sculpture the skeleton during growth.

The process of bone resorption by the osteoclasts releases stored calcium into the systemic circulation and is an important process in regulating calcium balance. As bone formation actively fixes circulating calcium in its mineral form, removing it from the bloodstream, resorption actively unfixes it thereby increasing circulating calcium levels. These processes occur in tandem at site-specific locations.

Repeated stress, such as weight-bearing exercise or bone healing, results in the bone thickening at the points of maximum stress (Wolff's law). It has been hypothesized that this is a result of bone's piezoelectric properties, which cause bone to generate small electrical potentials under stress.

II. miRNAs

A. Background

In 2001, several groups used a novel cloning method to isolate and identify a large group of "microRNAs" (miRNAs) from *C. elegans, Drosophila*, and humans (Lagos-Quintana et al., 2001; Lau et al., 2001; Lee and Ambros, 2001). Several hundreds of miRNAs have been identified in plants and animals—including humans—which do not appear to have endogenous siRNAs. Thus, while similar to siRNAs, miRNAs are nonetheless distinct.

miRNAs thus far observed have been approximately 21-22 nucleotides in length and they arise from longer precursors, which are transcribed from non-protein-encoding genes. See review of Carrington et al. (2003). The precursors form structures that fold back on each other in self-complementary regions; they are then processed by the nuclease Dicer in animals or DCL1 in plants. miRNA molecules interrupt translation through precise or imprecise base-pairing with their targets.

miRNAs are transcribed by RNA polymerase II and can be derived from individual miRNA genes, from introns of protein coding genes, or from poly-cistronic transcripts that often encode multiple, closely related miRNAs. Pre-miRNAs, generally several thousand bases long are processed in the nucleus by the RNase Drosha into 70- to 100-nt hairpin-shaped precursors. Following transport to the cytoplasm, the hairpin is further processed by Dicer to produce a double-stranded miRNA. The mature miRNA strand is then incorporated into the RNA-induced silencing complex (RISC), where it associates with its target mRNAs by base-pair complementarity. In the relatively rare cases in which a miRNA base pairs perfectly with an mRNA target, it promotes mRNA degradation. More commonly, miRNAs form imperfect heteroduplexes with target mRNAs, affecting either mRNA stability or inhibiting mRNA translation.

The 5' portion of a miRNA spanning bases 2-8, termed the 'seed' region, is especially important for target recognition (Krenz and Robbins, 2004; Kiriazis and Krania, 2000). The sequence of the seed, together with phylogenetic conservation of the target sequence, forms the basis for many current target prediction models. Although increasingly sophisticated computational approaches to predict miRNAs and their targets are becoming available, target prediction remains a major challenge and requires experimental validation. Ascribing the functions of miRNAs to the regulation of specific mRNA targets is further complicated by the ability of individual miRNAs to base pair with hundreds of potential high and low affinity mRNA targets and by the targeting of multiple miRNAs to individual mRNAs.

The first miRNAs were identified as regulators of developmental timing in *C. elegans*, suggesting that miRNAs, in general, might play decisive regulatory roles in transitions between different developmental states by switching off specific targets (Fatkin et al., 2000; Lowes et al., 1997). However, subsequent studies suggest that miRNAs, rather than functioning as on-off "switches," more commonly function to modulate or fine-tune cell phenotypes by repressing expression of proteins that are inappropriate for a particular cell type, or by adjusting protein dosage. miRNAs have also been proposed to provide robustness to cellular phenotypes by eliminating extreme fluctuations in gene expression.

Characterizing the functions of biomolecules like miRNAs often involves introducing the molecules into cells or removing the molecules from cells and measuring the result. If introducing a miRNA into cells results in apoptosis, then the miRNA undoubtedly participates in an apoptotic pathway. Methods for introducing and removing miRNAs from cells have been described. Two publications describe antisense molecules that can be used to inhibit the activity of specific miRNAs (Meister et al., 2004; Hutvagner et al., 2004), and others have proven their functionality in the heart, where they efficiently knocked-down miR-133 and miR-1 (Care et al. 2007; Yang et al. 2007). Another publication describes the use of plasmids that are transcribed by endogenous RNA polymerases and yield specific miRNAs when transfected into cells (Zeng et al., 2002). These two reagent sets have been used to evaluate single miRNAs.

B. miR-34a

The mir-34 microRNA precursor family are non-coding RNA molecules that, in mammals, give rise to three major mature miRNAs. The miR-34 family members were discovered computationally and later verified experimentally. The precursor miRNA stem-loop is processed in the cytoplasm of the cell, with the predominant miR-34 mature sequence excised from the 5' arm of the hairpin. The mature miR-34a is a part of the p53 tumor suppressor network of proteins; therefore, it is hypothesized that miR-34 dysregulation is involved in the development of some cancers.

In mammals, three miR-34 precursors are produced from two transcriptional units. The human miR-34a precursor is transcribed from chromosome 1. The miR-34b and miR-34c precursors are co-transcribed from a region on chromosome 11, apparently as part of a transcript known as BC021736. Expression of miR-34a in mouse is observed in all tissues examined but is highest in brain. miR-34b and -c are relatively less abundant in most tissues, but are the predominant miR-34 species in lung. The presence of miR-34 products has also been confirmed in embryonic stem cells. It has been shown that miR-34 is maternally inherited in drospophila and zebrafish, and that miR-34a targets the silent information regulator 1 (SIRT1) gene.

A quantitative proteomics-SILAC approach was used to identify miR-34a targets at genome level in HEK293T cells. p53-deficient human gastric cancer cells, restoration of functional miR-34 inhibits cell growth and induces chemosensitization and apoptosis, indicating that miR-34 may restore p53 function. Restoration of miR-34 inhibits tumorsphere formation and growth, which is reported to be correlated to the self-renewal of cancer stem cells. The mechanism of miR-34-mediated suppression of self-renewal appears to be related to the direct modulation of downstream targets Bcl-2, Notch, and HMGA2, indicating that miR-34 may be involved in gastric cancer stem cell self-renewal/differentiation decision-making. miR-34c has also been associated to bone development and bone cancer. Mir-34a is found overexpressed in the CSF and brain extracellular fluid in postmortem studies comparing patients with AD and controls.

The sequences for human (SEQ ID NO: 1) and mouse (SEQ ID NO: 2) miR-34a are shown below:

```
hsa-mir-34a MI0000268 (Human)
GGCCAGCUGUGAGUGUUUCUUUGGCAGUGUCUUAGCUGGUUGUUGUGAG

CAAUAGUAAGGAAGCAAUCAGCAAGUAUACUGCCCUAGAAGUGCUGCAC

GUUGUGGGCCC mmu-mir-34a MI0000584 (Mouse)
CCAGCUGUGAGUAAUUCUUUGGCAGUGUCUUAGCUGGUUGUUGUGAGUA

UUAGCUAAGGAAGCAAUCAGCAAGUAUACUGCCCUAGAAGUGCUGCACA

UUGU
```

C. Agonists of miR-34a

Agonists of miR-34a will generally take one of three forms. First, there is miR-34a itself. Such molecules may be delivered to target cells, for example, by injection or infusion, optionally in a delivery vehicle such as a lipid, such as a liposome or lipid emulsion. Second, one may use expression vectors that drive the expression of miR-34a. The composition and construction of various expression vectors is described elsewhere in the document. Third, one may use agents distinct from miR-34a that act up-regulate, stabilize or otherwise enhance the activity of miR-34a, including small molecules. Such molecules include "mimetics," molecules which mimic the function. Mimetics are generally defined as distinct from the structure of miR-34a but having 7 to 30 linked nucleosides, wherein the nucleobase sequence of the oligonucleotide has at least 80% seed region identity with the nucleobase sequence of miR-34.

In some embodiments, the miRNAs or mimetics comprise some or only modified nucleotides. For example, one or more nucleosides of the oligonucleotide comprise a modified sugar, such as 2'-O-methyl, 2'-O-methoxyethyl, 2'-fluoro, and a bicyclic sugar.

In certain embodiments, a 2'-modified nucleoside has a bicyclic sugar moiety. In certain such embodiments, the bicyclic sugar moiety is a D sugar in the alpha configuration. In certain such embodiments, the bicyclic sugar moiety is a D sugar in the beta configuration. In certain such embodiments, the bicyclic sugar moiety is an L sugar in the alpha configuration. In certain such embodiments, the bicyclic sugar moiety is an L sugar in the beta configuration.

In certain embodiments, the bicyclic sugar moiety comprises a bridge group between the T and the 4'-carbon atoms. In certain such embodiments, the bridge group comprises from 1 to 8 linked biradical groups. In certain embodiments, the bicyclic sugar moiety comprises from 1 to 4 linked biradical groups. In certain embodiments, the bicyclic sugar moiety comprises 2 or 3 linked biradical groups. In certain embodiments, the bicyclic sugar moiety comprises 2 linked biradical groups. In certain embodiments, a linked biradical group is selected from —O—, —S—, —N($R_1$)—, —C($R_1$)($R_2$)—, —C($R_1$)=C($R_1$)—, —C($R_1$)=N—, —C(=N$R_1$)—, —Si($R_1$)($R_2$)—, —S(=O)$_2$—, —S(=O)—, —C(=O)— and —C(=S)—; where each $R_1$ and $R_2$ is, independently, H, hydroxyl, $C_1$-$C_{12}$ alkyl, substituted $C_1$-$C_{12}$ alkyl, $C_2$-$C_{12}$ alkenyl, substituted $C_2$-$C_{12}$ alkenyl, $C_2$-$C_{12}$ alkynyl, substituted $C_2$-$C_{12}$ alkynyl, $C_5$-$C_{20}$ aryl, substituted $C_5$-$C_{20}$ aryl, a heterocycle radical, a substituted hetero-cycle radical, heteroaryl, substituted heteroaryl, $C_5$-$C_7$ alicyclic radical, substituted $C_5$-$C_7$ alicyclic radical, halogen, substituted oxy (—O—), amino, substituted amino, azido, carboxyl, substituted carboxyl, acyl, substituted acyl, CN, thiol, substituted thiol, sulfonyl (S(=O)$_2$—H), substituted sulfonyl, sulfoxyl (S(=O)—H) or substituted sulfoxyl; and each substituent group is, independently, halogen, $C_1$-$C_{12}$ alkyl, substituted $C_1$-$C_{12}$ alkyl, $C_2$-$C_{12}$ alkenyl, substituted $C_2$-$C_{12}$ alkenyl, $C_2$-$C_{12}$ alkynyl, substituted $C_2$-$C_{12}$ alkynyl, amino, substituted amino, acyl, substituted acyl, $C_1$-$C_{12}$ aminoalkyl, $C_1$-$C_{12}$ aminoalkoxy, substituted $C_1$-$C_{12}$ aminoalkyl, substituted $C_1$-$C_{12}$ aminoalkoxy or a protecting group.

In some embodiments, the bicyclic sugar moiety is bridged between the 2' and 4' carbon atoms with a biradical group selected from —O—(CH$_2$)$_p$—, —O—CH$_2$—, —O—CH$_2$CH$_2$—, —O—CH(alkyl)-, —NH—(CH$_2$)$_p$—, —N(alkyl)-(CH$_2$)$_p$—, —O—CH(alkyl)-, —(CH(alkyl))-(CH$_2$)$_p$—, —NH—O—(CH$_2$)$_p$—, —N(alkyl)-O—(CH$_2$)$_p$—, or —O—N(alkyl)-(CH$_2$)$_p$—, wherein p is 1, 2, 3, 4 or 5 and each alkyl group can be further substituted. In certain embodiments, p is 1, 2 or 3.

In certain embodiments, the oligonucleotide comprises at least one modified nucleobase, such as a 5-methylcytosine.

In certain embodiments, a 2'-modified nucleoside comprises a T-substituent group selected from halo, allyl, amino, azido, SH, CN, OCN, CF$_3$, OCF$_3$, O—, S—, or N($R_m$)-alkyl; or N($R_m$)-alkenyl; or N($R_m$)-alkynyl; O-alkylenyl-O-alkyl, alkynyl, alkaryl, aralkyl, O-alkaryl, O-aralkyl, O(CH$_2$)$_2$SCH$_3$, O—(CH$_2$)$_2$—O—N($R_m$)($R_n$) or O—CH$_2$—C(=O)—N($R_m$)($R_n$), where each $R_m$ and $R_n$ is, independently, H, an amino protecting group or substituted or unsubstituted $C_1$-$C_{10}$ alkyl. These T-substituent groups can be further substituted with one or more substituent groups independently selected from hydroxyl, amino, alkoxy, carboxy, benzyl, phenyl, nitro (NO$_2$), thiol, thioalkoxy (S-alkyl), halogen, alkyl, aryl, alkenyl and alkynyl.

In certain embodiments, a 2'-modified nucleoside comprises a 2'-substituent group selected from F, NH$_2$, N$_3$, OCF$_3$, O—CH$_3$, O(CH$_2$)$_3$NH$_2$, CH$_2$—CH=CH$_2$, O—CH$_2$—CH=CH$_2$, OCH$_2$CH$_2$OCH$_3$, O(CH$_2$)$_2$SCH$_3$, O—(CH$_2$)$_2$—O—N($R_m$)($R_n$), —O(CH$_2$)$_2$O(CH$_2$)$_2$N(CH$_3$)$_2$, and N-substituted acetamide (O—CH$_2$—C(=O)—N($R_m$)($R_n$)) where each $R_m$ and $R_n$ is, independently, H, an amino protecting group or substituted or unsubstituted $C_1$-$C_{10}$ alkyl.

In certain embodiments, a 2'-modified nucleoside comprises a 2'-substituent group selected from F, OCF$_3$, O—CH$_3$, OCH$_2$CH$_2$OCH$_3$, 2'-O(CH$_2$)$_2$SCH$_3$, O—(CH$_2$)$_2$—O—N(CH$_3$)$_2$, —O(CH$_2$)$_2$O(CH$_2$)$_2$N(CH$_3$)$_2$, and O—CH$_2$—C(=O)—N(H)CH$_3$.

In certain embodiments, a 2'-modified nucleoside comprises a 2'-substituent group selected from F, O—CH$_3$, and OCH$_2$CH$_2$OCH$_3$.

In certain embodiments, a sugar-modified nucleoside is a 4'-thio modified nucleoside. In certain embodiments, a sugar-modified nucleoside is a 4'-thio-2'-modified nucleoside. A 4'-thio modified nucleoside has a β-D-ribonucleoside where the 4'-O replaced with 4'-S. A 4'-thio-2'-modified nucleoside is a 4'-thio modified nucleoside having the 2'-OH replaced with a 2'-substituent group. Suitable 2'-substituent groups include T-OCH$_3$, 2'-O—(CH$_2$)$_2$—OCH$_3$, and 2'-F.

In certain embodiments, an oligonucleotide of the present invention comprises one or more internucleoside modifications. In certain such embodiments, each internucleoside linkage of a modified oligonucleotide is a modified internucleoside linkage. In certain embodiments, a modified internucleoside linkage comprises a phosphorus atom. In certain embodiments, an oligonucleotide of the present invention comprises at least one phosphorothioate internucleoside linkage. In certain embodiments, each internucleoside linkage of a modified oligonucleotide is a phosphorothioate internucleoside linkage.

In certain embodiments, a modified internucleoside linkage does not comprise a phosphorus atom. In certain such embodiments, an internucleoside linkage is formed by a short chain alkyl internucleoside linkage. In certain such embodiments, an internucleoside linkage is formed by a cycloalkyl internucleoside linkage. In certain such embodiments, an internucleoside linkage is formed by a mixed heteroatom and alkyl internucleoside linkage. In certain such embodiments, an internucleoside linkage is formed by a mixed heteroatom and cycloalkyl internucleoside linkages. In certain such embodiments, an internucleoside linkage is formed by one or more short chain heteroatomic internucleoside linkages. In certain such embodiments, an internucleoside linkage is formed by one or more heterocyclic internucleoside linkages. In certain such embodiments, an internucleoside linkage has an amide backbone. In certain such embodiments, an internucleoside linkage has mixed N, O, S and $CH_2$ component parts.

In certain embodiments, an oligonucleotide comprises one or more modified nucleobases. In certain embodiments, a modified oligonucleotide comprises one or more 5-methylcytosines. In certain embodiments, each cytosine of a modified oligonucleotide comprises a 5-methylcytosine.

In certain embodiments, a modified nucleobase is selected from 5-hydroxymethyl cytosine, 7-deazaguanine and 7-deazaadenine. In certain embodiments, a modified nucleobase is selected from 7-deaza-adenine, 7-deazaguanosine, 2-aminopyridine and 2-pyridone. In certain embodiments, a modified nucleobase is selected from 5-substituted pyrimidines, 6-azapyrimidines and N-2, N-6 and O-6 substituted purines, including 2 aminopropyladenine, 5-propynyluracil and 5-propynylcytosine.

In certain embodiments, a modified nucleobase comprises a polycyclic heterocycle. In certain embodiments, a modified nucleobase comprises a tricyclic heterocycle. In certain embodiments, a modified nucleobase comprises a phenoxazine derivative. In certain embodiments, the phenoxazine can be further modified to form a nucleobase known in the art as a G-clamp.

III. Methods of Treatment

A. Pharmacological Therapeutic Agents and Administration

The present invention addresses therapies, e.g., treatment of bone loss conditions. In various embodiments, the inhibitory agents of the present invention are formulated for administration in pharmacologically acceptable vehicles, such as parenteral, topical, aerosal, liposomal, nasal or ophthalmic preparations. In certain embodiments, formulations may be designed for oral or topical administration. It is further envisioned that formulations of nucleic acids encoding cytoskeletal stabilizing proteins and any other agents that might be delivered may be formulated and administered in a manner that does not require that they be in a single pharmaceutically acceptable carrier. In those situations, it would be clear to one of ordinary skill in the art the types of diluents that would be proper for the proposed use of the polypeptides and any secondary agents required.

The phrases "pharmaceutically" or "pharmacologically acceptable" refer to molecular entities and compositions that do not produce adverse, allergic, or other untoward reactions when administered to an animal or a human. As used herein, "pharmaceutically acceptable carrier" includes any and all solvents, dispersion media, coatings, antibacterial and antifungal agents, isotonic and absorption delaying agents and the like. The use of such media and agents for pharmaceutically active substances is well known in the art. Except insofar as any conventional media or agent is incompatible with the compositions, vectors or cells of the present invention, its use in therapeutic compositions is contemplated. Supplementary active ingredients also can be incorporated into the compositions.

The active compositions of the present invention may include classic pharmaceutical preparations. Administration of these compositions according to the present invention will be via any common route so long as the target tissue or surface is available via that route. This includes oral, nasal, or topical. Alternatively, administration may be by introcular, intra-hepatic, orthotopic, intradermal, subcutaneous, intramuscular, intraperitoneal or intravenous injection. Such compositions would normally be administered as pharmaceutically acceptable compositions, described supra.

The active compounds may also be administered parenterally or intraperitoneally. Solutions of the active compounds as free base or pharmacologically acceptable salts can be prepared in water suitably mixed with a surfactant, such as hydroxypropylcellulose. Dispersions can also be prepared in glycerol, liquid polyethylene glycols, and mixtures thereof and in oils. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases the form must be sterile and must be fluid to the extent that easy syringability exists. It must be stable under the conditions of manufacture and storage and must be preserved against the contaminating action of microorganisms, such as bacteria and fungi. The carrier can be a solvent or dispersion medium containing, for example, water, ethanol, polyol (for example, glycerol, propylene glycol, and liquid polyethylene glycol, and the like), suitable mixtures thereof, and vegetable oils. The proper fluidity can be maintained, for example, by the use of a coating, such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

Sterile injectable solutions are prepared by incorporating the active compounds in the required amount in the appropriate solvent with various other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof.

As used herein, "pharmaceutically acceptable carrier" includes any and all solvents, dispersion media, coatings, antibacterial and antifungal agents, isotonic and absorption delaying agents and the like. The use of such media and agents for pharmaceutical active substances is well known in the art. Except insofar as any conventional media or agent is incompatible with the active ingredient, its use in the therapeutic compositions is contemplated. Supplementary active ingredients can also be incorporated into the compositions.

The compositions of the present invention may be formulated in a neutral or salt form. Pharmaceutically-acceptable salts include the acid addition salts (formed with the free amino groups of the protein) and which are formed with inorganic acids such as, for example, hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine and the like.

For parenteral administration in an aqueous solution, for example, the solution should be suitably buffered if necessary and the liquid diluent first rendered isotonic with sufficient saline or glucose. These particular aqueous solutions are especially suitable for intravenous, intramuscular, subcutaneous and intraperitoneal administration. In this connection, sterile aqueous media which can be employed will be known to those of skill in the art in light of the present disclosure. For example, one dosage could be dissolved in 1 ml of isotonic NaCl solution and either added to 1000 ml of hypodermoclysis fluid or injected at the proposed site of infusion, (see for example, "Remington's Pharmaceutical Sciences" 15th Edition, pages 1035-1038 and 1570-1580). Some variation in dosage will necessarily occur depending on the condition of the subject being treated. The person responsible for administration will, in any event, determine the appropriate dose for the individual subject. Moreover, for human administration, preparations should meet sterility, pyrogenicity, general safety and purity standards as required by FDA Office of Biologics standards.

In a particular embodiment, the miR-34a agonists may be delivered using a "nanoparticle." Nanoparticles are generally considered to be particulate substances having a diameter of 100 nm or less. In contrast to liposomes, which are hollow, nanoparticles tend to be solid. Thus, the drug will be less entrapped and more either embedded in or coated on the nanoparticle. Nanoparticles can be made of metals including oxides, silica, polymers such as polymethyl methacrylate, and ceramics. Similarly, nanoshells are somewhat larger and encase the delivered substances with these same materials. Either nanoparticles or nanoshells permit sustained or controlled release of the peptide or mimetic, and can stabilize it to the effects of in vivo environment.

One particular type of nanoparticle delivery system is the chitosan nanoparticle. As chitin occurs naturally, chitosan is fully biodegradable and biocompatible. Not surprisingly, it has been investigated extensively as a potential drug carrier. The size and degree of deacetylation can be modified in order to obtain different properties. Chitosan nanoparticles can be used for drug delivery and biological therapy applications, and a number of groups have studied their in vivo delivery properties. The biocompatibility and non-toxicity of the material makes it attractive as a neutral agent for delivery of active agents.

The following patents and applications describe various chitosan nanoparticle delivery systems: U.S. Pat. Nos. 8,502,015, 8,449,915, 8,187,571, 8,137,697, 7,901,711, 7,901,666, 7,883,723, 7,740,883; U.S. Patent Publications 20130189367, 20130149385, 20130078210, 20120269729, 20120128781, 20120107268, 20120040004, 20120039854, 20110305765, 20110064676, 20110064665, 20110059162, 20100267139, 20100260686, 20100098768, 20100015232, 20090130186, 20080233060, 20080219938, 20080095810, 20060013885 and 20050226938, each of the foregoing documents being incorporated by reference in their entirety.

B. Devices

In addition to providing anti-TGF-β antibodies for administration by routes discussed above, such agents, alone or in combination, maybe used in the context of devices, such as implants. A variety of bone related implants are contemplated, including dental implants, joint implants such as hips, knees, and elbows, vertebral/spinal implants, and others. The anti-TGF-β antibodies may be impregnated in a surface of the implant, including in a bioactive matrix or coating. The inhibitor may be further formulated to sustained, delayed, prolonged or time release. The coating may comprise polymers, for example, such as those listed below. The following is a list of U.S. patents relating to bone implants and devices which may be utilized in accordance with this embodiment of the invention:

TABLE 1

BONE IMPLANT PATENTS

| U.S. Pat. No.* | Patent Title |
| --- | --- |
| 7,044,972 | Bone implant, in particular, an inter-vertebral implant |
| 7,022,137 | Bone hemi-lumbar interbody spinal fusion implant having an asymmetrical leading end and method of installation thereof |
| 7,001,551 | Method of forming a composite bone material implant |
| 6,994,726 | Dual function prosthetic bone implant and method for preparing the same |
| 6,989,031 | Hemi-interbody spinal implant manufactured from a major long bone ring or a bone composite |
| 6,988,015 | Bone implant |
| 6,981,975 | Method for inserting a spinal fusion implant having deployable bone engaging projections |
| 6,981,872 | Bone implant method of implanting, and kit for use in making implants, particularly useful with respect to dental implants |
| 6,929,662 | End member for a bone fusion implant |
| 6,923,830 | Spinal fusion implant having deployable bone engaging projections |
| 6,921,264 | Implant to be implanted in bone tissue or in bone tissue supplemented with bone substitute material |
| 6,918,766 | Method, arrangement and use of an implant for ensuring delivery of bioactive substance to the bone and/or tissue surrounding the implant |
| 6,913,621 | Flexible implant using partially demineralized bone |
| 6,899,734 | Modular implant for fusing adjacent bone structure |
| 6,860,884 | Implant for bone connector |
| 6,852,129 | Adjustable bone fusion implant and method |
| 6,802,845 | Implant for bone connector |
| 6,786,908 | Bone fracture support implant with non-metal spacers |
| 6,767,367 | Spinal fusion implant having deployable bone engaging projections |
| 6,761,738 | Reinforced molded implant formed of cortical bone |
| 6,755,832 | Bone plate implant |
| 6,730,129 | Implant for application in bone, method for producing such an implant, and use of such an implant |
| 6,689,167 | Method of using spinal fusion device, bone joining implant, and vertebral fusion implant |
| 6,689,136 | Implant for fixing two bone fragments to each other |
| 6,666,890 | Bone hemi-lumbar interbody spinal implant having an asymmetrical leading end and method of installation thereof |
| 6,652,592 | Segmentally demineralized bone implant |
| 6,648,917 | Adjustable bone fusion implant and method |
| 6,607,557 | Artificial bone graft implant |
| 6,599,322 | Method for producing undercut micro recesses in a surface, a surgical implant made thereby, and method for fixing an implant to bone |
| 6,562,074 | Adjustable bone fusion implant and method |
| 6,562,073 | Spinal bone implant |
| 6,540,770 | Reversible fixation device for securing an implant in bone |
| 6,537,277 | Implant for fixing a bone plate |

TABLE 1-continued

BONE IMPLANT PATENTS

| U.S. Pat. No.* | Patent Title |
|---|---|
| 6,506,051 | Bone implant with intermediate member and expanding assembly |
| 6,478,825 | Implant, method of making same and use of the implant for the treatment of bone defects |
| 6,458,136 | Orthopaedic instrument for sizing implant sites and for pressurizing bone cement and a method for using the same |
| 6,447,545 | Self-aligning bone implant |
| 6,436,146 | Implant for treating ailments of a joint or a bone |
| 6,371,986 | Spinal fusion device, bone joining implant, and vertebral fusion implant |
| 6,370,418 | Device and method for measuring the position of a bone implant |
| 6,364,880 | Spinal implant with bone screws |
| 6,350,283 | Bone hemi-lumbar interbody spinal implant having an asymmetrical leading end and method of installation thereof |
| 6,350,126 | Bone implant |
| 6,287,343 | Threaded spinal implant with bone ingrowth openings |
| 6,270,346 | Dental implant for bone regrowth |
| 6,248,109 | Implant for interconnecting two bone fragments |
| 6,217,617 | Bone implant and method of securing |
| 6,214,050 | Expandable implant for inter-bone stabilization and adapted to extrude osteogenic material, and a method of stabilizing bones while extruding osteogenic material |
| 6,213,775 | Method of fastening an implant to a bone and an implant therefor |
| 6,206,923 | Flexible implant using partially demineralized bone |
| 6,203,545 | Implant for fixing bone fragments after an osteotomy |
| 6,149,689 | Implant as bone replacement |
| 6,149,688 | Artificial bone graft implant |
| 6,149,686 | Threaded spinal implant with bone ingrowth openings |
| 6,126,662 | Bone implant |
| 6,083,264 | Implant material for replacing or augmenting living bone tissue involving thermoplastic syntactic foam |
| 6,058,590 | Apparatus and methods for embedding a biocompatible material in a polymer bone implant |
| 6,018,094 | Implant and insert assembly for bone and uses thereof |
| 5,976,147 | Modular instrumentation for bone preparation and implant trial reduction of orthopedic implants |
| 5,906,488 | Releasable holding device preventing undesirable rotation during tightening of a screw connection in a bone anchored implant |
| 5,899,939 | Bone-derived implant for load-supporting applications |
| 5,895,425 | Bone implant |
| 5,890,902 | Implant bone locking mechanism and artificial periodontal ligament system |
| 5,885,287 | Self-tapping interbody bone implant |
| 5,819,748 | Implant for use in bone surgery |
| 5,810,589 | Dental implant abutment combination that reduces crestal bone stress |
| 5,759,035 | Bone fusion dental implant with hybrid anchor |
| 5,720,750 | Device for the preparation of a tubular bone for the insertion of an implant shaft |
| 5,709,683 | Interbody bone implant having conjoining stabilization features for bony fusion |
| 5,709,547 | Dental implant for anchorage in cortical bone |
| 5,674,725 | Implant materials having a phosphatase and an organophosphorus compound for in vivo mineralization of bone |
| 5,658,338 | Prosthetic modular bone fixation mantle and implant system |
| D381,080 | Combined metallic skull base surgical implant and bone flap fixation plate |
| 5,639,402 | Method for fabricating artificial bone implant green parts |
| 5,624,462 | Bone implant and method of securing |
| D378,314 | Bone spinal implant |
| 5,607,430 | Bone stabilization implant having a bone plate portion with integral cable clamping means |
| 5,571,185 | Process for the production of a bone implant and a bone implant produced thereby |
| 5,456,723 | Metallic implant anchorable to bone tissue for replacing a broken or diseased bone |
| 5,441,538 | Bone implant and method of securing |
| 5,405,388 | Bone biopsy implant |
| 5,397,358 | Bone implant |
| 5,383,935 | Prosthetic implant with self-generated current for early fixation in skeletal bone |
| 5,364,268 | Method for installing a dental implant fixture in cortical bone |
| 5,312,256 | Dental implant for vertical penetration, adapted to different degrees of hardness of the bone |

*The preceding patents are all hereby incorporated by reference in their entirety.

C. Combined Therapy

In another embodiment, it is envisioned to use the agonists of the present invention in combination with other therapeutic modalities. Thus, in addition to the therapies described above, one may also provide to the patient more "standard" pharmaceutical therapies. Combinations may be achieved by contacting cells, tissues or subjects with a single composition or pharmacological formulation that includes both agents, or by contacting the cell with two distinct compositions or formulations, at the same time, wherein one composition includes the agonist and the other includes the other agent. Alternatively, the therapy using an agonist may precede or follow administration of the other agent(s) by intervals ranging from minutes to weeks. In embodiments where the other agent and agonist are applied separately to the cell, one would generally ensure that a significant period of time did not expire between the time of each delivery, such that the agent and the agonist would still be able to exert an advantageously combined effect on the cell, tissue or subject. In such instances, it is contemplated that one would typically contact the cell with both modalities within about 12-24 hours of each other and, more preferably, within about 6-12 hours of each other, with a delay time of only about 12 hours being most preferred. In some situations, it may be desirable to extend the time period for treatment significantly, however, where several days (2, 3, 4, 5, 6 or 7) to several weeks (1, 2, 3, 4, 5, 6, 7 or 8) lapse between the respective administrations.

It also is conceivable that more than one administration of either a modulator of miR, or the other agent will be desired. In this regard, various combinations may be employed. By way of illustration, where the miR-34a agonist(s) is "A" and the other agent is "B," the following permutations based on 3 and 4 total administrations are exemplary:

| A/B/A | B/A/B | B/B/A | A/A/B | B/A/A | A/B/B |
| B/B/B/A | B/B/A/B | A/A/B/B | A/B/A/B | A/B/B/A | B/B/A/A |
| B/A/B/A | B/A/A/B | B/B/B/A | A/A/A/B | B/A/A/A | A/B/A/A |
| A/A/B/A | A/B/B/B | B/A/B/B | B/B/A/B | | |

Other combinations are likewise contemplated. Administration protocols and formulation of such agents will generally follow those of standard pharmaceutical drugs, as discussed further below. Combination agents include bisphosphonates (Didronel™, Fosamax™ and Actonel™), SERMs (Evista) or other hormone derivatives, and Parathyroid Hormone (PTH) analogs.

D. Disease States

A plethora of conditions are characterized by the need to enhance bone formation or to inhibit bone resorption and thus would benefit from the use of miR-34a as described above or cells treated therewith in promoting bone formation and/or bone repair. Perhaps the most obvious is the case of bone fractures, where it would be desirable to stimulate bone growth and to hasten and complete bone repair. Agents that enhance bone formation would also be useful in facial reconstruction procedures. Other bone deficit conditions include bone segmental defects, periodontal disease, metastatic bone disease, osteolytic bone disease and conditions where connective tissue repair would be beneficial, such as healing or regeneration of cartilage defects or injury. Also of great significance is the chronic condition of osteoporosis, including age-related osteoporosis and osteoporosis associated with post-menopausal hormone status. Other conditions characterized by the need for bone growth include primary and secondary hyperparathyroidism, disuse osteoporosis, diabetes-related osteoporosis, and glucocorticoid-related osteoporosis. Several other conditions, such as, for example, vitamin D deficiency, exists. Finally, bone attacking cancers are another significant application of this technology.

Fracture.

The first example is the otherwise healthy individual who suffers a fracture. Often, clinical bone fracture is treated by casting to alleviate pain and allow natural repair mechanisms to repair the wound. There has been progress in the treatment of fracture in recent times, however, even without considering the various complications that may arise in treating fractured bones, any new procedures to increase bone healing in normal circumstances would represent a great advance.

Periodontal Disease.

Progressive periodontal disease leads to tooth loss through destruction of the tooth's attachment to the surrounding bone. Approximately 5-20% of the U.S. population (15-60 million individuals) suffers from severe generalized periodontal disease, and there are 2 million related surgical procedures. Moreover, if the disease is defined as the identification of at least one site of clinical attachment loss, then approximately 80% of all adults are affected, and 90% of those aged 55 to 64 years. If untreated, approximately 88% of affected individuals show moderate to rapid progression of the disease' which shows a strong correlation with age. The major current treatment for periodontal disease is regenerative therapy consisting of replacement of lost periodontal tissues. The lost bone is usually treated with an individual's own bone and bone marrow, due to their high osteogenic potential. Bone allografts (between individuals) can also be performed using stored human bone. Although current periodontal cost analyses are hard to obtain, the size of the affected population and the current use of bone grafts as a first-order therapy strongly suggest that this area represents an attractive target for bone-building therapies.

Osteopenia/Osteoporosis.

The terms osteopenia and osteoporosis refers to a heterogeneous group of disorders characterized by decreased bone mass and fractures. Osteopenia is a bone mass that is one or more standard deviations below the mean bone mass for a population; osteoporosis is defined as 2.5 SD or lower. An estimated 20-25 million people are at increased risk for fracture because of site-specific bone loss. Risk factors for osteoporosis include increasing age, gender (more females), low bone mass, early menopause, race (Caucasians in general; asian and hispanic females), low calcium intake, reduced physical activity, genetic factors, environmental factors (including cigarette smoking and abuse of alcohol or caffeine), and deficiencies in neuromuscular control that create a propensity to fall. More than a million fractures in the U.S. each year can be attributed to osteoporosis. In economic terms, the costs (exclusive of lost wages) for osteoporosis therapies are $35 billion worldwide. Demographic trends (i.e., the gradually increasing age of the U.S. population) suggest that these costs may increase to $62 billion by the year 2020. Clearly, osteoporosis is a significant health care problem.

Osteoporosis, once thought to be a natural part of aging among women, is no longer considered age or gender-dependent. Osteoporosis is defined as a skeletal disorder characterized by compromised bone strength predisposing to an increased risk of fracture. Bone strength reflects the integration of two main features: bone density and bone quality. Bone density is expressed as grams of mineral per area or volume and in any given individual is determined by peak bone mass and amount of bone loss. Bone quality refers to architecture, turnover, damage accumulation (e.g., microfractures) and mineralization. A fracture occurs when a failure-inducing force (e.g., trauma) is applied to osteoporotic bone.

Current therapies for osteoporosis patients focus on fracture prevention, not for promoting bone formation or fracture repair. This remains an important consideration because of the literature, which clearly states that significant morbidity and mortality are associated with prolonged bed rest in the elderly, particularly those who have suffered hip fractures. Complications of bed rest include blood clots and pneumonia. These complications are recognized and measures are usually taken to avoid them, but these is hardly the best approach to therapy. Thus, the osteoporotic patient population would benefit from new therapies designed to strengthen bone and speed up the fracture repair process, thus getting these people on their feet before the complications arise.

Bone Reconstruction/Grafting.

A fourth example is related to bone reconstruction and, specifically, the ability to reconstruct defects in bone tissue that result from traumatic injury; as a consequence of cancer or cancer surgery; as a result of a birth defect; or as a result of aging. There is a significant need for more frequent orthopedic implants, and cranial and facial bone are particular targets for this type of reconstructive need. The availability of new implant materials, e.g., titanium, has permitted the repair of relatively large defects. Titanium implants provide excellent temporary stability across bony defects and are an excellent material for bone implants or artificial joints such as hip, knee and joint replacements. However, experience has shown that a lack of viable bone binding to implants the defect can result in exposure of the appliance to infection, structural instability and, ultimately, failure to repair the defect. Thus, a therapeutic agent that stimulates bone formation on or around the implant will facilitate more rapid recovery.

Autologous bone grafts are another possibility, but they have several demonstrated disadvantages in that they must be harvested from a donor site such as iliac crest or rib, they usually provide insufficient bone to completely fill the defect, and the bone that does form is sometimes prone to infection and resorption. Partially purified xenogeneic preparations are not practical for clinical use because microgram quantities are purified from kilograms of bovine bone, making large scale commercial production both costly and impractical. Allografts and demineralized bone preparations are therefore often employed, but suffer from their devitalized nature in that they only function as scaffolds for endogenous bone cell growth.

Microsurgical transfers of free bone grafts with attached soft tissue and blood vessels can close bony defects with an immediate source of blood supply to the graft. However, these techniques are time consuming, have been shown to produce a great deal of morbidity, and can only be used by specially trained individuals. Furthermore, the bone implant is often limited in quantity and is not readily contoured. In the mandible, for example, the majority of patients cannot wear dental appliances using presently accepted techniques (even after continuity is established), and thus gain little improvement in the ability to masticate.

In connection with bone reconstruction, specific problem areas for improvement are those concerned with treating large defects, such as created by trauma, birth defects, or particularly, following tumor resection; and also the area of artificial joints. The success of orthopaedic implants, interfaces and artificial joints could conceivably be improved if the surface of the implant, or a functional part of an implant, were to be coated with a bone stimulatory agent. The surface of implants could be coated with one or more appropriate materials in order to promote a more effective interaction with the biological site surrounding the implant and, ideally, to promote tissue repair.

Primary Bone Cancer and Metastatic Bone Disease.

Bone cancer occurs infrequently while bone metastases are present in a wide range of cancers, including thyroid, kidney, and lung. Metastatic bone cancer is a chronic condition; survival from the time of diagnosis is variable depending on tumor type. In prostate and breast cancer and in multiple myeloma, survival time is measurable in years. For advanced lung cancer, it is measured in months. Cancer symptoms include pain, hypercalcemia, pathologic fracture, and spinal cord or nerve compression. Prognosis of metastatic bone cancer is influenced by primary tumor site, presence of extra-osseous disease, and the extent and tempo of the bone disease. Bone cancer/metastasis progression is determined by imaging tests and measurement of bone specific markers. Recent investigations show a strong correlation between the rate of bone resorption and clinical outcome, both in terms of disease progression or death.

Multiple Myeloma.

Multiple myeloma (MM) is a B-lymphocyte malignancy characterized by the accumulation of malignant clonal plasma cells in the bone marrow. The clinical manifestations of the disease are due to the replacement of normal bone marrow components by abnormal plasma cells, with subsequent overproduction of a monoclonal immunoglobulin (M protein or M component), bone destruction, bone pain, anemia, hypercalcemia and renal dysfunction.

As distinct from other cancers that spread to the bone (e.g., breast, lung, thyroid, kidney, prostate), myeloma bone disease (MBD) is not a metastatic disease. Rather, myeloma cells are derived from the B-cells of the immune system that normally reside in the bone marrow and are therefore intimately associated with bone. Indeed, the bone marrow microenvironment plays an important role in the growth, survival and resistance to chemotherapy of the myeloma cells, which, in turn, regulate the increased bone loss associated with this disorder. Over 90% of myeloma patients have bone involvement, versus 40-60% of cancer patients who have bone metastasis, and over 80% have intractable bone pain. Additionally, approximately 30% of myeloma patients have hypercalcemia that is a result of the increased osteolytic activity associated with this disease.

Common problems in myeloma are weakness, confusion and fatigue due to hypercalcemia. Headache, visual changes and retinopathy may be the result of hyperviscosity of the blood depending on the properties of the paraprotein. Finally, there may be radicular pain, loss of bowel or bladder control (due to involvement of spinal cord leading to cord compression) or carpal tunnel syndrome and other neuropathies (due to infiltration of peripheral nerves by amyloid). It may give rise to paraplegia in late presenting cases.

Myeloma Bone Disease.

As discussed above, unlike the osteolysis associated with other bone tumors, the MBD lesions are unique in that they do not heal or repair, despite the patients' having many years of complete remission. Mechanistically, this seems to be related to the inhibition and/or loss of the bone-forming osteoblast during disease progression. Indeed, bone marker studies and histomorphometry indicate that both the bone-resorbing osteoclast and osteoblast activity are increased, but balanced early in the disease, whereas overt MBD shows high osteoclast activity and low osteoblast activity. Thus, MBD is a disorder in which bone formation and bone loss are uncoupled and would benefit from therapies that both stimulate bone formation and retard its loss.

A number of therapeutic approaches have been used in MBD, with the endpoints of treating pain, hypercalcemia, or the reduction of skeletal related events (SRE). Many of these may present serious complications. Surgery, such as vertebroplasty or kyphoplasty, that is performed for stability and pain relief has the attendant surgical risks (e.g., infection) made worse by a compromised immune system and does not reverse existing skeletal defects. Radiation therapy and radioisotope therapy are both used to prevent/control disease progression and have the typical risks of irradiation therapies. More recently, drugs such as the bisphosphonates that inhibit osteoclast activity have become a standard of therapy for MBD, despite the fact that they work poorly in this disorder. In 9 major double-blind, placebo-controlled trials on bisphosphonates, only 66% of patients showed an effective reduction in pain; 56% showed a reduction in SRE and only 1 of the 9 demonstrated a survival benefit.

Rheumatoid Arthritis.

Rheumatoid arthritis (RA) is an autoimmune disease that results in a chronic, systemic inflammatory disorder that may affect many tissues and organs, but principally attacks flexible (synovial) joints. It can be a disabling and painful condition, which can lead to substantial loss of functioning and mobility if not adequately treated. The process involves an inflammatory response of the capsule around the joints (synovium) secondary to swelling (turgescence) of synovial cells, excess synovial fluid, and the development of fibrous tissue (pannus) in the synovium. The pathology of the disease process often leads to the destruction of articular cartilage and ankylosis (fusion) of the joints. RA can also produce diffuse inflammation in the lungs, the membrane around the heart (pericardium), the membranes of the lung (pleura), and white of the eye (sclera), and also nodular lesions, most common in subcutaneous tissue. Although the cause of RA is unknown, autoimmunity plays a big part, and RA is a systemic autoimmune disease. It is a clinical diagnosis made on the basis of symptoms, physical exam, radiographs (X-rays) and labs.

Treatments are pharmacological and non-pharmacological. Non-pharmacological treatment includes physical therapy, orthoses, occupational therapy and nutritional therapy but these don't stop the progression of joint destruction. Analgesia (painkillers) and anti-inflammatory drugs, including steroids, suppress symptoms, but don't stop the progression of joint destruction either. Disease-modifying antirheumatic drugs (DMARDs) slow or halt the progress of the disease. The newer biologics are DMARDs. The evidence for complementary and alternative medicine (CAM) treatments for RA related pain is weak, with the lack of high quality evidence leading to the conclusions that their use is currently not supported by the evidence nor proved to be of benefit.

About 0.6% of the United States adult population has RA, women two to three times as often as men. Onset is most frequent during middle age, but people of any age can be affected. RA primarily affects joints; however it also affects other organs in 15-25% of individuals. It can be difficult to determine whether disease manifestations are directly caused by the rheumatoid process itself, or from side effects of the medications used to treat it—for example, lung fibrosis from methotrexate or osteoporosis from corticosteroids.

Arthritis of joints involves inflammation of the synovial membrane. Joints become swollen, tender and warm, and stiffness limits their movement. With time multiple joints are affected (it is a polyarthritis). Most commonly involved are the small joints of the hands, feet and cervical spine, but larger joints like the shoulder and knee can also be involved. Synovitis can lead to tethering of tissue with loss of movement and erosion of the joint surface causing deformity and loss of function.

RA typically manifests with signs of inflammation, with the affected joints being swollen, warm, painful and stiff, particularly early in the morning on waking or following prolonged inactivity. Increased stiffness early in the morning is often a prominent feature of the disease and typically lasts for more than an hour. Gentle movements may relieve symptoms in early stages of the disease. These signs help distinguish rheumatoid from non-inflammatory problems of the joints, often referred to as osteoarthritis or "wear-and-tear" arthritis. In arthritis of non-inflammatory causes, signs of inflammation and early morning stiffness are less prominent with stiffness typically less than 1 hour, and movements induce pain caused by mechanical arthritis. In RA, the joints are often affected in a fairly symmetrical fashion, although this is not specific, and the initial presentation may be asymmetrical.

Local osteoporosis occurs in RA around inflamed joints. It is postulated to be partially caused by inflammatory cytokines. More general osteoporosis is probably contributed to by immobility, systemic cytokine effects, local cytokine release in bone marrow and corticosteroid therapy.

Paget's Disease.

Paget's disease of bone is a chronic disorder that can result in enlarged and misshapen bones. The excessive breakdown and formation of bone tissue causes affected bone to weaken, resulting in pain, misshapen bones, fractures, and arthritis in the joints near the affected bones. Paget's disease typically is localized, affecting just one or a few bones, as opposed to osteoporosis, for example, which usually affects all the bones in the body. Decisions about treating Paget's disease can be complicated because no two people are affected in exactly the same way by the disease, and because it is sometimes difficult to predict whether a person with Paget's disease who shows no signs of the disorder will develop symptoms or complications (such as a bone fracture) at a later date. Although there is no cure for Paget's disease, medications can help control the disorder and lessen pain and other symptoms. Paget's disease experts recommend that these medications be taken by people with Paget's disease who have bone pain, headache, back pain, or a nerve-related symptom (such as "shooting" pains in the leg) that is directly associated with the disease; have elevated levels of serum alkaline phosphatase (ALP) in their blood; display evidence that a bone fracture will occur; require pretreatment therapy for affected bones that require surgery; have active symptoms in the skull, long bones, or vertebrae (spine); have the disease in bones located next to major joints, placing them at risk of developing osteoarthritis; develop hypercalcemia that occurs when a person with several bones affected by Paget's disease and a high serum alkaline phosphatase level is immobilized.

Today's medications, especially when started before complications begin, are often successful in controlling the disorder. Paget's disease is rarely diagnosed in people less than 40 years of age. Men are more commonly affected than women (3:2). Prevalence of Paget's disease ranges from 1.5 to 8.0 percent, depending on age and country of residence. Prevalence of familial Paget's disease (where more than one family member has the disease) ranges from 10 to 40 percent in different parts of the world. Because early diagnosis and treatment is important, after age 40, siblings and children of someone with Paget's disease may wish to have an alkaline phosphatase blood test every two or three years. If the alkaline phosphatase level is above normal, other tests such as a bone-specific alkaline phosphatase test, bone scan, or X-ray can be performed.

The pathogenesis of Paget's disease is described in 4 stages: osteoclastic activity; mixed osteoclastic-osteoblastic activity; osteoblastic activity; and malignant degeneration. Initially, there is a marked increase in the rate of bone resorption at localized areas caused by large and numerous osteoclasts. These localized areas of osteolysis are seen radiologically as an advancing lytic wedge in long bones or osteoporosis circumscripta in the skull. The osteolysis is followed by a compensatory increase in bone formation induced by osteoblasts recruited to the area. This is associated with accelerated deposition of lamellar bone in a disorganized fashion. This intense cellular activity produces a chaotic picture of trabecular bone ("mosaic" pattern), rather than the normal linear lamellar pattern. The resorbed bone is replaced and the marrow spaces are filled by an excess of fibrous connective tissue with a marked increase in blood vessels, causing the bone to become hypervascular. The bone hypercellularity may then diminish, leaving a dense "pagetic bone," also known as burned-out Paget's disease.

The goal of treatment is to relieve bone pain and prevent the progression of the disease. Five bisphosphonates are currently available. In general, the most commonly prescribed are risedronic acid (Actonel), alendronic acid (Fosamax), and pamidronic acid (Aredia). Etidronic acid (Didronel) and other bisphosphonates may be appropriate therapies for selected patients but are less commonly used. As a rule, bisphosphonate tablets should be taken with 200-250 mL (6-8& oz) of tap water (not from a source with high mineral content) on an empty stomach. None of these drugs should be used by people with severe kidney disease.

Etidronate disodium (Didronel) in tablet form is available in 200-400 mg doses. The approved regimen is once daily for six months; the higher dose (400 mg) is more commonly used. No food, beverage, or medications should be consumed for two hours before and after taking. The course should not exceed six months, but repeat courses can be given after rest periods, preferably of three to six months duration.

Pamidronate disodium (Aredia) in intravenous form: the approved regimen uses a 30 mg infusion over four hours on each of three consecutive days, but a more commonly used regimen is 60 mg over two to four hours for two or more consecutive or nonconsecutive days.

Alendronate sodium (Fosamax) is given as tablets of 40 mg once daily for six months; patients should wait at least 30 minutes after taking before eating any food, drinking anything other than tap water, taking any medication, or lying down (patient may sit).

Tiludronate disodium (Skelid) in two tablets of 200 mg are taken once daily for three months; they may be taken any time of day, as long as there is a period of two hours before and after resuming food, beverages, and medications.

Risedronate sodium (Actonel) as a 30 mg tablet taken once daily for 2 months is the prescribed regimen; patients should wait at least 30 minutes after taking before eating any food, drinking anything other than tap water, taking any medication, or lying down (patient may sit).

Zoledronic acid (Reclast, Aclasta) is given as an intravenous infusion; a single dose (5 mg over 15 minutes) is effective for two years.

Miacalcin is administered by injection; 50 to 100 units daily or three times per week for 6-18 months. Repeat courses can be given after brief rest periods. Miacalcin may be appropriate for certain patients, but is seldom used. However, it is to be remembered that calcitonin is also linked to increased chance of cancer. The European equivalent of the US Food and Drug Administration (FDA) recommended withdrawing calcitonin nasal spray because of an increased risk for cancer.

Risk.

The present invention also contemplates treating individuals at risk for any of the aforementioned disease states. These individuals would include those persons suffering from conditions discussed above.

IV. Kits

Any of the compositions described herein may be comprised in a kit. In a non-limiting example, an individual miRNA agonist (e.g., expression construct, mimetic) is included in a kit. The kit may also include one or more transfection reagent(s) to facilitate delivery of the agonist to cells.

The components of the kits may be packaged either in aqueous media or in lyophilized form. The container means of the kits will generally include at least one vial, test tube, flask, bottle, syringe or other container means, into which a component may be placed, and preferably, suitably aliquoted. Where there is more than one component in the kit (labeling reagent and label may be packaged together), the kit also will generally contain a second, third or other additional container into which the additional components may be separately placed. However, various combinations of components may be comprised in a vial. The kits of the present invention also will typically include a means for containing the nucleic acids, and any other reagent containers in close confinement for commercial sale. Such containers may include injection or blow-molded plastic containers into which the desired vials are retained.

When the components of the kit are provided in one and/or more liquid solutions, the liquid solution is an aqueous solution, with a sterile aqueous solution being particularly preferred. However, the components of the kit may be provided as dried powder(s). When reagents and/or components are provided as a dry powder, the powder can be reconstituted by the addition of a suitable solvent. It is envisioned that the solvent may also be provided in another container means.

The container means will generally include at least one vial, test tube, flask, bottle, syringe and/or other container means, into which the nucleic acid formulations are placed, preferably, suitably allocated. The kits may also comprise a second container means for containing a sterile, pharmaceutically acceptable buffer and/or other diluent.

The kits of the present invention will also typically include a means for containing the vials in close confinement for commercial sale, such as, e.g., injection and/or blow-molded plastic containers into which the desired vials are retained.

Such kits may also include components that preserve or maintain the miRNA or that protect against its degradation. Such components may be RNAse-free or protect against RNAses. Such kits generally will comprise, in suitable means, distinct containers for each individual reagent or solution. A kit will also include instructions for employing the kit components as well the use of any other reagent not included in the kit. Instructions may include variations that can be implemented.

It is contemplated that such reagents are embodiments of kits of the invention. Such kits, however, are not limited to the particular items identified above and may include any reagent used for the manipulation or characterization of miRNA.

V. Vectors for Cloning, Gene Transfer and Expression

Within certain embodiments expression vectors are employed to express nucleic acid agonist, such as miRs, antisense molecules. Expression requires that appropriate signals be provided in the vectors, and which include various regulatory elements, such as enhancers/promoters from both viral and mammalian sources that drive expression of the genes of interest in host cells. Elements designed to optimize messenger RNA stability and translatability in host cells also are defined. The conditions for the use of a number of dominant drug selection markers for establishing permanent, stable cell clones expressing the products are also provided, as is an element that links expression of the drug selection markers to expression of the polypeptide.

A. Regulatory Elements

Throughout this application, the term "expression construct" is meant to include any type of genetic construct containing a nucleic acid coding for a gene product in which part or all of the nucleic acid encoding sequence is capable of being transcribed. Generally, the nucleic acid encoding a gene product is under transcriptional control of a promoter. A "promoter" refers to a DNA sequence recognized by the synthetic machinery of the cell, or introduced synthetic machinery, required to initiate the specific transcription of a gene. The phrase "under transcriptional control" means that the promoter is in the correct location and orientation in relation to the nucleic acid to control RNA polymerase initiation and expression of the gene.

The term promoter will be used here to refer to a group of transcriptional control modules that are clustered around the initiation site for RNA polymerase II. Much of the thinking about how promoters are organized derives from analyses of several viral promoters, including those for the HSV thymidine kinase (tk) and SV40 early transcription units. These studies, augmented by more recent work, have shown that promoters are composed of discrete functional modules, each consisting of approximately 7-20 by of DNA, and containing one or more recognition sites for transcriptional activator or repressor proteins.

At least one module in each promoter functions to position the start site for RNA synthesis. The best known example of this is the TATA box, but in some promoters lacking a TATA box, such as the promoter for the mammalian terminal deoxynucleotidyl transferase gene and the promoter for the SV40 late genes, a discrete element overlying the start site itself helps to fix the place of initiation.

Additional promoter elements regulate the frequency of transcriptional initiation. Typically, these are located in the region 30-110 by upstream of the start site, although a number of promoters have recently been shown to contain functional elements downstream of the start site as well. The spacing between promoter elements frequently is flexible, so that promoter function is preserved when elements are inverted or moved relative to one another. In the tk promoter, the spacing between promoter elements can be increased to 50 bp apart before activity begins to decline. Depending on the promoter, it appears that individual elements can function either co-operatively or independently to activate transcription.

In other embodiments, the human cytomegalovirus (CMV) immediate early gene promoter, the SV40 early promoter, the Rous sarcoma virus long terminal repeat, rat insulin promoter and glyceraldehyde-3-phosphate dehydrogenase can be used to obtain high-level expression of the coding sequence of interest. The use of other viral or mammalian cellular or bacterial phage promoters which are well-known in the art to achieve expression of a coding sequence of interest is contemplated as well, provided that the levels of expression are sufficient for a given purpose.

By employing a promoter with well-known properties, the level and pattern of expression of the protein of interest following transfection or transformation can be optimized. Further, selection of a promoter that is regulated in response to specific physiologic signals can permit inducible expression of the gene product. Tables 2 and 3 list several regulatory elements that may be employed, in the context of the present disclosure, to provide expression for the miRNA. This list is not intended to be exhaustive of all the possible elements involved in the promotion of gene expression but, merely, to be exemplary thereof.

Enhancers are genetic elements that increase transcription from a promoter located at a distant position on the same molecule of DNA. Enhancers are organized much like promoters. That is, they are composed of many individual elements, each of which binds to one or more transcriptional proteins.

The basic distinction between enhancers and promoters is operational. An enhancer region as a whole must be able to stimulate transcription at a distance; this need not be true of a promoter region or its component elements. On the other hand, a promoter must have one or more elements that direct initiation of RNA synthesis at a particular site and in a particular orientation, whereas enhancers lack these specificities. Promoters and enhancers are often overlapping and contiguous, often seeming to have a very similar modular organization.

Below is a list of viral promoters, cellular promoters/enhancers and inducible promoters/enhancers that could be used in combination with the nucleic acid encoding a gene of interest in an expression construct (Table 2 and Table 3). Additionally, any promoter/enhancer combination (as per the Eukaryotic Promoter Data Base EPDB) could also be used to drive expression of the gene. Eukaryotic cells can support cytoplasmic transcription from certain bacterial promoters if the appropriate bacterial polymerase is provided, either as part of the delivery complex or as an additional genetic expression construct.

TABLE 2

Promoter and/or Enhancer

| Promoter/Enhancer | References |
|---|---|
| Immunoglobulin Heavy Chain | Banerji et al., 1983; Gilles et al., 1983; Grosschedl et al., 1985; Atchinson et al., 1986, 1987; Imler et al., 1987; Weinberger et al., 1984; Kiledjian et al., 1988; Porton et al.; 1990 |
| Immunoglobulin Light Chain | Queen et al., 1983; Picard and Shaffner, 1984 |
| T-Cell Receptor | Luria et al., 1987; Winoto et al., 1989; Redondo et al.; 1990 |
| HLA DQ a and/or DQ β | Sullivan et al., 1987 |
| β-Interferon | Goodbourn et al., 1986; Fujita et al., 1987; Goodbourn et al., 1988 |
| Interleukin-2 | Greene et al., 1989 |
| Interleukin-2 Receptor | Greene et al., 1989; Lin et al., 1990 |
| MHC Class II 5 | Koch et al., 1989 |
| MHC Class II HLA-DRa | Sherman et al., 1989 |
| β-Actin | Kawamoto et al., 1988; Ng et al.; 1989 |
| Muscle Creatine Kinase (MCK) | Jaynes et al., 1988; Horlick and Benfield, 1989; Johnson et al., 1989 |
| Prealbumin (Transthyretin) | Costa et al., 1988 |
| Elastase I | Omitz et al., 1987 |
| Metallothionein (MTII) | Karin et al., 1987; Culotta et al., 1989 |
| Collagenase | Pinkert et al., 1987; Angel et al., 1987a |
| Albumin | Pinkert et al., 1987; Tronche et al., 1989, 1990 |
| α-Fetoprotein | Godbout et al., 1988; Campere et al., 1989 |
| t-Globin | Bodine et al., 1987; Perez-Stable et al., 1990 |
| β-Globin | Trudel et al., 1987 |
| c-fos | Cohen et al., 1987 |
| c-HA-ras | Triesman, 1986; Deschamps et al., 1985 |
| Insulin | Edlund et al., 1985 |
| Neural Cell Adhesion Molecule (NCAM) | Hirsh et al., 1990 |
| α$_1$-Antitrypain | Latimer et al., 1990 |
| H2B (TH2B) Histone | Hwang et al., 1990 |
| Mouse and/or Type I Collagen | Ripe et al., 1989 |
| Glucose-Regulated Proteins (GRP94 and GRP78) | Chang et al., 1989 |
| Rat Growth Hormone | Larsen et al., 1986 |
| Human Serum Amyloid A (SAA) | Edbrooke et al., 1989 |
| Troponin I (TN I) | Yutzey et al., 1989 |
| Platelet-Derived Growth Factor (PDGF) | Pech et al., 1989 |
| Duchenne Muscular Dystrophy | Klamut et al., 1990 |
| SV40 | Banerji et al., 1981; Moreau et al., 1981; Sleigh et al., 1985; Firak and Subramanian, 1986; Herr et al., 1986; Imbra et al., 1986; Kadesch et al., 1986; Wang et al., 1986; Ondek et al., 1987; Kuhl et al., 1987; Schaffner et al., 1988 |
| Polyoma | Swartzendruber et al., 1975; Vasseur et al., 1980; Katinka et al., 1980, 1981; Tyndell et al., 1981; Dandolo et al., 1983; de Villiers et al., 1984; Hen et al., 1986; Satake et al., 1988; Campbell and/or Villarreal, 1988 |

TABLE 2-continued

Promoter and/or Enhancer

| Promoter/Enhancer | References |
|---|---|
| Retroviruses | Kriegler et al., 1982, 1983; Levinson et al., 1982; Kriegler et al., 1983, 1984a, b, 1988; Bosze et al., 1986; Miksicek et al., 1986; Celander and Haselton, 1987; Thiesen et al., 1988; Celander et al., 1988; Choi et al., 1988; Reisman et al., 1989 |
| Papilloma Virus | Campo et al., 1983; Lusky et al., 1983; Spandidos and/or Wilkie, 1983; Spalholz et al., 1985; Lusky et al., 1986; Cripe et al., 1987; Gloss et al., 1987; Hirochika et al., 1987; Stephens et al., 1987 |
| Hepatitis B Virus | Bulla et al., 1986; Jameel et al., 1986; Shaul et al., 1987; Spandau et al., 1988; Vannice et al., 1988 |
| Human Immunodeficiency Virus | Muesing et al., 1987; Hauber et al., 1988; Jakobovits et al., 1988; Feng and Holland, et al., 1988; Takebe et al., 1988; Rosen et al., 1988; Berkhout et al., 1989; Laspia et al., 1989; Sharp et al., 1989; Braddock et aL, 1989 |
| Cytomegalovirus (CMV) | Weber et al., 1984; Boshart et al., 1985; Foecking and Hofstetter, 1986 |
| Gibbon Ape Leukemia Virus | Holbrook et al., 1987; Quinn et al., 1989 |

TABLE 3

Inducible Elements

| Element | Inducer | References |
|---|---|---|
| MT II | Phorbol Ester (TFA) Heavy metals | Palmiter et al., 1982; Haslinger et al., 1985; Searle et al., 1985; Stuart et al., 1985; Imagawa et al., 1987, Karin et al., 1987; Angel et al., 1987b; McNeall et al., 1989 |
| MMTV (mouse mammary tumor virus) | Glucocorticoids | Huang et al., 1981; Lee et al., 1981; Majors et al., 1983; Chandler et al., 1983; Ponta et al., 1985; Sakai et al., 1988 |
| β-Interferon | poly(rI)x poly(rc) | Tavernier et al., 1983 |
| Adenovirus 5 E2 | E1A | Imperiale et al., 1984 |
| Collagenase | Phorbol Ester (TPA) | Angel et al., 1987a |
| Stromelysin | Phorbol Ester (TPA) | Angel et al., 1987b |
| SV40 | Phorbol Ester (TPA) | Angel et al., 1987b |
| Murine MX Gene | Interferon, Newcastle Disease Virus | Hug et al., 1988 |
| GRP78 Gene | A23187 | Resendez et al., 1988 |
| α-2-Macroglobulin | IL-6 | Kunz et al., 1989 |
| Vimentin | Serum | Rittling et al., 1989 |
| MHC Class I Gene H-2κb | Interferon | Blanar et al., 1989 |
| HSP70 | E1A, SV40 Large T Antigen | Taylor et al., 1989, 1990a, 1990b |

TABLE 3-continued

Inducible Elements

| Element | Inducer | References |
|---|---|---|
| Proliferin | Phorbol Ester-TPA | Mordacq et al., 1989 |
| Tumor Necrosis Factor | PMA | Hensel et al., 1989 |
| Thyroid Stimulating Hormone α Gene | Thyroid Hormone | Chatterjee et al., 1989 |

Where a cDNA insert is employed, one will typically desire to include a polyadenylation signal to effect proper polyadenylation of the gene transcript. The nature of the polyadenylation signal is not believed to be crucial to the successful practice of the invention, and any such sequence may be employed such as human growth hormone and SV40 polyadenylation signals. Also contemplated as an element of the expression cassette is a terminator. These elements can serve to enhance message levels and to minimize read through from the cassette into other sequences.

B. Selectable Markers

In certain embodiments of the invention, the cells contain nucleic acid constructs of the present invention, a cell may be identified in vitro or in vivo by including a marker in the expression construct. Such markers would confer an identifiable change to the cell permitting easy identification of cells containing the expression construct. Usually the inclusion of a drug selection marker aids in cloning and in the selection of transformants, for example, genes that confer resistance to neomycin, puromycin, hygromycin, DHFR, GPT, zeocin and histidinol are useful selectable markers. Alternatively, enzymes such as herpes simplex virus thymidine kinase (tk) or chloramphenicol acetyltransferase (CAT) may be employed. Immunologic markers also can be employed. The selectable marker employed is not believed to be important, so long as it is capable of being expressed simultaneously with the nucleic acid encoding a gene product. Further examples of selectable markers are well known to one of skill in the art.

C. Delivery of Expression Vectors

There are a number of ways in which expression vectors may be introduced into cells. In certain embodiments of the invention, the expression construct comprises a virus or engineered construct derived from a viral genome. The ability of certain viruses to enter cells via receptor-mediated endocytosis, to integrate into host cell genome and express viral genes stably and efficiently have made them attractive candidates for the transfer of foreign genes into mammalian cells (Ridgeway, 1988; Nicolas and Rubenstein, 1988; Baichwal and Sugden, 1986; Temin, 1986). The first viruses used as gene vectors were DNA viruses including the papovaviruses (simian virus 40, bovine papilloma virus, and polyoma) (Ridgeway, 1988; Baichwal and Sugden, 1986) and adenoviruses (Ridgeway, 1988; Baichwal and Sugden, 1986). Vectors derived from viruses such as vaccinia virus (Ridgeway, 1988; Baichwal and Sugden, 1986; Coupar et al., 1988) adeno-associated virus (AAV) (Ridgeway, 1988; Baichwal and Sugden, 1986; Hermonat and Muzycska, 1984) and herpesviruses may be employed. They offer several attractive features for various mammalian cells (Friedmann, 1989; Ridgeway, 1988; Baichwal and Sugden, 1986; Coupar et al., 1988; Horwich et al., 1990). Defective hepatitis B viruses also are useful as expression vectors (Horwich et al., 1990).

Several non-viral methods for the transfer of expression constructs into cultured mammalian cells also are contemplated by the present invention. These include calcium phosphate precipitation (Graham and Van Der Eb, 1973;

Chen and Okayama, 1987; Rippe et al., 1990) DEAE-dextran (Gopal, 1985), electroporation (Tur-Kaspa et al., 1986; Potter et al., 1984), direct microinjection (Harland and Weintraub, 1985), DNA-loaded liposomes (Nicolau and Sene, 1982; Fraley et al., 1979) and lipofectamine-DNA complexes, cell sonication (Fechheimer et al., 1987), gene bombardment using high velocity microprojectiles (Yang et al., 1990), and receptor-mediated transfection (Wu and Wu, 1987; Wu and Wu, 1988). Some of these techniques may be successfully adapted for in vivo or ex vivo use.

Once the expression construct has been delivered into the cell the nucleic acid encoding the gene of interest may be positioned and expressed at different sites. In certain embodiments, the nucleic acid encoding the gene may be stably integrated into the genome of the cell. This integration may be in the cognate location and orientation via homologous recombination (gene replacement) or it may be integrated in a random, non-specific location (gene augmentation). In yet further embodiments, the nucleic acid may be stably maintained in the cell as a separate, episomal segment of DNA. Such nucleic acid segments or "episomes" encode sequences sufficient to permit maintenance and replication independent of or in synchronization with the host cell cycle. How the expression construct is delivered to a cell and where in the cell the nucleic acid remains is dependent on the type of expression construct employed.

In yet another embodiment of the invention, the expression construct may simply consist of naked recombinant DNA or plasmids. Transfer of the construct may be performed by any of the methods mentioned above which physically or chemically permeabilize the cell membrane. This is particularly applicable for transfer in vitro but it may be applied to in vivo use as well. Dubensky et al. (1984) successfully injected polyomavirus DNA in the form of calcium phosphate precipitates into liver and spleen of adult and newborn mice demonstrating active viral replication and acute infection. Benvenisty and Neshif (1986) also demonstrated that direct intraperitoneal injection of calcium phosphate-precipitated plasmids results in expression of the transfected genes. It is envisioned that DNA encoding a gene of interest may also be transferred in a similar manner in vivo and express the gene product.

In still another embodiment of the invention for transferring a naked DNA expression construct into cells may involve particle bombardment. This method depends on the ability to accelerate DNA-coated microprojectiles to a high velocity allowing them to pierce cell membranes and enter cells without killing them (Klein et al., 1987). Several devices for accelerating small particles have been developed. One such device relies on a high voltage discharge to generate an electrical current, which in turn provides the motive force (Yang et al., 1990). The microprojectiles used have consisted of biologically inert substances such as tungsten or gold beads.

Selected organs including the eye, liver, skin, and muscle tissue of rats and mice have been bombarded in vivo (Yang et al., 1990; Zelenin et al., 1991). This may require surgical exposure of the tissue or cells, to eliminate any intervening tissue between the gun and the target organ, i.e., ex vivo treatment. Again, DNA encoding a particular gene may be delivered via this method and still be incorporated by the present invention.

In a further embodiment of the invention, the expression construct may be entrapped in a liposome. Liposomes are vesicular structures characterized by a phospholipid bilayer membrane and an inner aqueous medium. Multilamellar liposomes have multiple lipid layers separated by aqueous medium. They form spontaneously when phospholipids are suspended in an excess of aqueous solution. The lipid components undergo self-rearrangement before the formation of closed structures and entrap water and dissolved solutes between the lipid bilayers (Ghosh and Bachhawat, 1991). Also contemplated are lipofectamine-DNA complexes.

Liposome-mediated nucleic acid delivery and expression of foreign DNA in vitro has been very successful. Wong et al. (1980) demonstrated the feasibility of liposome-mediated delivery and expression of foreign DNA in cultured chick embryo, HeLa and hepatoma cells. Nicolau et al., (1987) accomplished successful liposome-mediated gene transfer in rats after intravenous injection.

In certain embodiments of the invention, the liposome may be complexed with a hemagglutinating virus (HVJ). This has been shown to facilitate fusion with the cell membrane and promote cell entry of liposome-encapsulated DNA (Kaneda et al., 1989). In other embodiments, the liposome may be complexed or employed in conjunction with nuclear non-histone chromosomal proteins (HMG-1) (Kato et al., 1991). In yet further embodiments, the liposome may be complexed or employed in conjunction with both HVJ and HMG-1. In that such expression constructs have been successfully employed in transfer and expression of nucleic acid in vitro and in vivo, then they are applicable for the present invention. Where a bacterial promoter is employed in the DNA construct, it also will be desirable to include within the liposome an appropriate bacterial polymerase.

Other expression constructs which can be employed to deliver a nucleic acid encoding a particular gene into cells are receptor-mediated delivery vehicles. These take advantage of the selective uptake of macromolecules by receptor-mediated endocytosis in almost all eukaryotic cells. Because of the cell type-specific distribution of various receptors, the delivery can be highly specific (Wu and Wu, 1993).

Receptor-mediated gene targeting vehicles generally consist of two components: a cell receptor-specific ligand and a DNA-binding agent. Several ligands have been used for receptor-mediated gene transfer. The most extensively characterized ligands are asialoorosomucoid (ASOR) (Wu and Wu, 1987) and transferrin (Wagner et al., 1990). Recently, a synthetic neoglycoprotein, which recognizes the same receptor as ASOR, has been used as a gene delivery vehicle (Ferkol et al., 1993; Perales et al., 1994) and epidermal growth factor (EGF) has also been used to deliver genes to squamous carcinoma cells (Myers, EPO 0273085).

In other embodiments, the delivery vehicle may comprise a ligand and a liposome. For example, Nicolau et al. (1987) employed lactosyl-ceramide, a galactose-terminal asialganglioside, incorporated into liposomes and observed an increase in the uptake of the insulin gene by hepatocytes. Thus, it is feasible that a nucleic acid encoding a particular gene also may be specifically delivered into a cell type by any number of receptor-ligand systems with or without liposomes. For example, epidermal growth factor (EGF) may be used as the receptor for mediated delivery of a nucleic acid into cells that exhibit upregulation of EGF receptor. Mannose can be used to target the mannose receptor on liver cells. Also, antibodies to CD5 (CLL), CD22 (lymphoma), CD25 (T-cell leukemia) and MAA (melanoma) can similarly be used as targeting moieties.

In a particular example, the oligonucleotide may be administered in combination with a cationic lipid. Examples of cationic lipids include, but are not limited to, lipofectin, DOTMA, DOPE, and DOTAP. The publication of WO/0071096, which is specifically incorporated by reference, describes different formulations, such as a DOTAP: cholesterol or cholesterol derivative formulation that can effectively be used for gene therapy. Other disclosures also discuss different lipid or liposomal formulations including nanoparticles and methods of administration; these include, but are not limited to, U.S. Patent Publication 20030203865, 20020150626, 20030032615, and 20040048787, which are specifically incorporated by reference to the extent they disclose formulations and other related aspects of administration and delivery of nucleic acids. Methods used for forming particles are also disclosed in U.S. Pat. Nos. 5,844,107, 5,877,302, 6,008,336, 6,077,835, 5,972,901, 6,200,801, and 5,972,900, which are incorporated by reference for those aspects.

In certain embodiments, gene transfer may more easily be performed under ex vivo conditions. Ex vivo gene therapy refers to the isolation of cells from an animal, the delivery of a nucleic acid into the cells in vitro, and then the return of the modified cells back into an animal. This may involve the surgical removal of tissue/organs from an animal or the primary culture of cells and tissues.

VI. Definitions

The term "treatment" or grammatical equivalents encompasses the improvement and/or reversal of the symptoms of disease. "Improvement in the physiologic function" of the eye may be assessed using any of the measurements described herein.

The term "compound" refers to any chemical entity, pharmaceutical, drug, and the like that can be used to treat or prevent a disease, illness, sickness, or disorder of bodily function. Compounds comprise both known and potential therapeutic compounds. A compound can be determined to be therapeutic by screening using the screening methods of the present invention. A "known therapeutic compound" refers to a therapeutic compound that has been shown (e.g., through animal trials or prior experience with administration to humans) to be effective in such treatment. In other words, a known therapeutic compound is not limited to a compound efficacious in the treatment of heart failure.

As used herein, the term "agonist" refers to molecules or compounds that mimic or promote the action of a "native" or "natural" compound. Agonists may be homologous to these natural compounds in respect to conformation, charge or other characteristics. Agonists may include proteins, nucleic acids, carbohydrates, small molecule pharmaceuticals or any other molecules that interact with a molecule, receptor, and/or pathway of interest.

VII. EXAMPLES

The following examples are included to further illustrate various aspects of the invention. It should be appreciated by those of skill in the art that the techniques disclosed in the examples which follow represent techniques and/or compositions discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1—Materials & Methods

Mice.

To generate cre-flox controlled conditional miR-34a transgenic mice (CAG34a), a 600 base-pair genomic sequence containing 200 base pairs 5' and 298 base pairs 3' of the pre-miR-34a sequence was inserted into the CAG-Z-EGFP vector (Fukuda et al., 2005; Fukuda et al., 2006; Hatley et al., 2010). Transgenic founders were established by pronuclear injection at the UT Southwestern transgenic core laboratory. To establish osteoclastic miR-34a transgenic mice, CAG34a mice were bred with the previously described Tie2cre transgenic mice (Constien et al., 2001; Kisanuki et al., 2001; Wan et al., 2007a; Wan et al., 2007b; Wei et al., 2010), PPARγ-tTA; TRE-cre (PT-cre) mice (Jin et al., 2012; Wei et al., 2011a; Wei et al., 2011b) or lysozyme-cre (Lys-cre) mice (Clausen et al., 1999). MiR-34a knockout and heterozygous mice were generated using a mouse embryonic stem cell line (International Gene Trap Consortium clone YHA350) harboring a gene-trap integration in the miR-34a transcription unit. Tgif2-KO mice were provided by Dr. David Wotton (University Of Virginia) (Powers et al., 2010). Bone marrow transplantation was performed as previously described (Wan et al., 2007a). Briefly, bone marrow cells from 2-month-old male donor (WT or 34a-KO) were intravenously transplanted into five 2-month-old male C57B6/J recipients that were irradiated at lethal dose (1000 roentgen); bone and serum were analyzed 3 month post transplantation. Ovariectomy or sham operation was performed on 10-20 week old female mice as previously described (Wei et al., 2011b). miRNA-carrying chitosan nanoparticles were delivered by intravenous injections at 5 μg/mouse or 10 μg/mouse twice per week for 4-5 weeks. All experiments were conducted using littermates. All protocols for mouse experiments were approved by the Institutional Animal Care and Use Committee of University of Texas Southwestern Medical Center.

Reagents.

Mouse Tgif2 siRNA or control siRNA were from Santa Cruz Biotechnology. MiR-34a precursor (pre-miR-34a) and negative control (pre-control), miR-34a inhibitor (anti-miR-34a) and negative control (anti-control) were from Life Technologies. All miRNA and siRNA were transfected with Lipofectamine™ RNAiMAX (Life Technologies) into bone marrow osteoclast progenitors. For in vivo miRNA delivery, HPLC-purified mirVana™ miR-34a mimic or negative control (Life Technologies) was packaged into chitosan nanoparticles as described (Lu et al., 2010).

Bone Analyses.

Micro-Computed Tomography (μCT) was performed to evaluate bone volume and architecture using a Scanco μCT-35 instrument (SCANCO Medical) as described (Wei et al., 2010). Mouse tibiae were fixed in 70% ethanol and scanned at several resolutions for both overall tibial assessment (14 micron resolution) and the structural analysis of trabecular and cortical bone (7 micron resolution). Trabecular bone parameters were calculated using the Scanco software to analyze the bone scans from the trabecular region directly distal to the proximal tibial growth plate. As a bone resorption marker, serum CTX-1 was measured with the RatLaps™ EIA kit (Immunodiagnostic Systems) (Wei et al., 2012b). As a bone formation marker, serum amino-terminal propeptide of type I collagen (P1NP) was measured with the Rat/Mouse P1NP enzyme immunoassay kit (Immunodiagnostic Systems) (Wei et al., 2012b).

Ex Vivo Osteoclast Differentiation.

Osteoclasts were differentiated from mouse bone marrow cells as described (Wan et al., 2007a; Wei et al., 2010). Briefly, hematopoietic bone marrow cells were purified with 40 µm cell strainer, and differentiated with 40 ng/ml of mouse M-CSF (R&D Systems) in α-MEM containing 10% FBS for 3 days, then with 40 ng/ml of mouse MCSF and 100 ng/ml of mouse RANKL (R&D Systems) for 3-9 days, in the presence or absence of rosiglitazone (1 µM). Mature osteoclasts were identified as multinucleated (>3 nuclei) TRAP+ cells. Osteoclast differentiation was quantified by the RNA expression of osteoclast marker genes using RT-QPCR analysis. THP-1 human monocytic cell line was differentiated into osteoclasts in RPMI1640 medium containing 10% FBS, 10 nM Vitamin D, 1 µM dexamethasone and 1 µM rosiglitazone for 14 days, human RANKL was added on day 7, pre-miR and anti-miR were transfected on day 0 and day 6.

Gene Expression Analyses.

For mRNA expression, RNA was reverse transcribed into cDNA using an ABI High Capacity cDNA RT Kit (Life Technologies) and then analyzed using real-time quantitative PCR (SYBR Green) in triplicate. All mRNA expression was normalized by L19. For mature miRNA expression, RNA was reverse transcribed into cDNA using NCode VILO miRNA cDNA Synthesis Kit (Life Technologies) and then analyzed in triplicate using real-time quantitative PCR (SYBR Green) and a primer specific for the mature miRNA. All miRNA expression was normalized by sno251.

Identification of miR-34a Targets in the Osteoclast Lineage.

To elucidate the molecular mechanisms for miR-34a inhibition of osteoclastogenessi and bone resorption, the inventor identified key direct miR-34a target genes that are pro-osteoclastogenic. First, she used the TargetScan bioinformatic tool to predict all the miR-34a targets by searching for conserved 8mer or 7mer sites that match the miR-34a seed region. Second, she searched databases such as BioGPS to select secondary targets that are expressed in the macrophage-osteoclast lineage. Third, she performed RT-QPCR to select tertiary targets that can be inhibited by miR-34a during osteoclast differentiation. Fourth, she performed luciferase reporter assay to test if the 3'UTR of each tertiary target could directly suppress gene expression in response to miR-34a. To generate a CMV-Luc-3'UTR reporter, a ~300 bp Tgif2 3'UTR region centering the miR-34a target sequence was cloned into the pMIR-REPORT™ vector (Life Technologies) downstream of the luciferase open reading frame. To generate a mutant reporter with miss-matched miR-34a binding site, the miR-34a target sequence was altered using QuikChange II XL site-directed mutagenesis kit (Stratagene). The reporters were co-transfected with CMV-β-gal (as an internal transfection control), together with pre-miR-34a or pre-miR-control, anti-miR-34a or anti-miR-control using FuGENE HD reagent (Roche). The transfection assay was conducted in human embryonic kidney 293 cells and CV-1 monkey kidney cells to assess the intrinsic properties of the 3'UTR in different cellular context, and representative results for 293 cells are shown. Luciferase activity was normalized by β-gal activity.

Bone Metastasis Analyses.

Using a VisualSonics Vevo770 small animal ultrasound device, luciferase-labeled cancer cells were injected into the left cardiac ventricle so that they can bypass the lung and efficiently migrate to the bone. Bone metastases were detected and quantified weekly post injection by bioluminescence imaging (BLI) using a Caliper Xenogen Spectrum instrument at UTSW small animal imaging core facility. The osteolytic metastatic lesions were imaged by radiography using Faxitron Cabinet X-ray System with the X-ray tube voltage fixed at 26 kVp and the exposure time at 15 s. The luciferase-labeled bone-metastasis-prone MDA-MB-231 human breast cancer cell sub-line (MDA231-BoM-1833) was generously provided by Joan Massagué (Memorial Sloan-Kettering Cancer Center) (Kang et al., 2003; Lu et al., 2009) and injected into 6-week-old female nude mice (NCI) at $1 \times 10^5$ cells/mouse in 100 µl PBS. The luciferase-labeled B16-F10 mouse melanoma cell line was generously provided by Katherine Weilbaecher (Washington University) (Uluckan et al., 2008) and injected into 8-week-old male C57B6/J mice at $5 \times 10^4$/mouse in 100 µl PBS.

Statistical Analyses.

All statistical analyses were performed with Student's t-Test and represented as mean±standard deviation (s.d.) unless noted otherwise. The p values were designated as: *, $p<0.05$; , $p<0.01$; *, $p<0.005$; ****, $p<0.001$; n.s. non-significant ($p>0.05$).

Example 2—Results

The inventor examined the levels of several cancer-related miRNAs during a time course of bone marrow osteoclastogenesis assay (FIG. 1A). While the expression of an osteoclast marker tartrate-resistant acid phosphatase (TRAP) was rapidly increased by RANKL and further elevated by rosiglitazone (Wan et al., 2007; Wei et al., 2010) (FIG. 1B), miR-34a was rapidly down-regulated by RANKL and further diminished by rosiglitazone (FIG. 1C). The levels of miR-34b/c, two other members in the miR-34 family, were unaffected and expressed at much lower levels than miR-34a (FIG. 1D).

The sequence of miR-34a is evolutionally conserved and identical in mice and humans. Osteoclast differentiation from both mouse bone marrow precursors (FIGS. 1E-F) and human peripheral blood mononuclear cells (hPBMN) (FIG. 1G-J) was inhibited by a miR-34a precursor (pre-miR-34a) but enhanced by an antisense miR-34a inhibitor (anti-miR-34a), indicating that miR-34a regulation of bone resorption in mice will likely translate to human pathophysiology.

The inventor generated osteoclastic miR-34a transgenic mice using CAG34a mice (FIG. 2A) and Tie2-cre mice (Wan et al., 2007; Wei et al., 2010). FACS and imaging showed that osteoclast progenitors from the 34a-Tie2-Tg (CAG34a$^+$Cre$^+$) mice were converted to GFP$^+$LacZ$^-$ whereas the controls (CAG34a$^+$Cre$^-$) remained GFP$^-$LacZ$^+$ (FIGS. 5A-B). Northern blot confirmed the over-expression of mature-miR-34a in the bone marrow of 34a-Tie2-Tg mice (FIG. 5C).

Osteoclast differentiation assay reveal that the higher levels of mature miR-34a in the 34a-Tie2-Tg cultures resulted in a lower induction of osteoclast markers, diminished number/size of mature osteoclasts, and reduced resorptive activity, whereas precursor proliferation or survival was unaltered (FIG. 2B, FIGS. 5D-G). Consequently, serum bone resorption marker CTX-1 (C-terminal telopeptides of Type I collagen) and osteoclast number were decreased, whereas osteoblast number, bone formation rate (BFR) and mineral apposition rate (MAR) were unaltered (FIG. 2C, FIGS. 1H-I).

µCT analysis of the proximal tibiae showed that 34a-Tie2-Tg mice had increased bone mass and decreased structure model index (SMI), which quantifies the relative amount of plates (SMI=0, strong) and rods (SMI=3, fragile) (FIGS. 2D-E). Cortical BV/TV was also higher (FIG. 2F). Moreover, miR-34a transgenic mice generated by three other osteoclast-targeting cre drivers also exhibited a similar phenotype (FIGS. 6A-D and 7A-H). Thus, miR-34a in the osteoclast lineage augment bone mass by suppressing osteoclastogenesis and bone resorption.

To determine whether miR-34a is a physiologically relevant regulator of bone resorption, the inventor next examined miR-34a knockout (34a-KO) and heterozygous (34a-Het) mice (FIG. 2G). Northern blot confirmed the diminished levels of miR-34a in 34a-KO (FIG. 8A). Consistent with prior reports (Choi et al., 2011; Concepcion et al., 2012), miR-34a deletion had no overt effect on mouse development. Osteoclast differentiation was augmented in 34a-Het and 34a-KO cultures, while precursor proliferation or survival was unaffected (FIG. 2H, FIGS. 8B-E). As a result, serum CTX-1 and osteoclast number were elevated (FIG. 2I, FIGS. 8G-H). μCT revealed that 34a-KO and 34a-Het mice exhibited a low-bone-mass with decreased connectivity density (Conn.D) and increased SMI (FIGS. 2J-L). Global miR-34a deletion also decreased bone formation as the serum marker P1NP (N-terminal propeptide of type I procollagen), osteoblast number, BFR and MAR were reduced (FIG. 2M, FIGS. 8G-H). The increased resorption in 34a-Het indicates that miR-34a function is haploinsufficient and sensitive to dosage reduction. The recently published miR-34abc triple KO (34abc-TKO)[10] and full miR-34a KO[9] also showed a similar phenotype (FIGS. 9A-H), which validate the miR-34a gene trap mice and strengthen the finding that miR-34a loss-of-function elevates bone resorption.

Bone marrow transplantation showed that WT mice receiving 34a-KO marrow also exhibited higher CTX-1 (FIG. 8F) compared to WT mice receiving WT marrow. Furthermore, osteoclastic miR-34a conditional KO mice (34a-Tie2-KO) also exhibited elevated osteoclast differentiation and bone resorption, but unaltered bone formation, leading to a decreased bone mass (FIGS. 9I-N). Thus, miR-34a deletion in the osteoclast lineage elevates bone resorption.

These genetic findings prompt us to investigate whether pharmacological administration of a miR-34a mimic can attenuate postmenopausal osteoporosis using an ovariectomy (OVX) mouse model and a chitosan (CH) nanoparticle vehicle. Reduction of uterine weight in all ovariectomized mice indicated effective estrogen depletion (FIG. 3A). Unaltered body weight indicates the absence of obvious toxicity from CH nanoparticles (FIG. 3B). Compared to sham controls, OVX mice treated with miR-Ctrl-CH showed increased CTX-1 and decreased P1NP, whereas both effects were largely prevented in OVX mice treated with miR-34a-CH (FIGS. 3C-D). Consequently, OVX-induced bone loss was attenuated by miR-34a-CH (FIGS. 4E-F; FIG. 10A). miR-34a-CH also decreased bone resorption and increased bone formation in sham controls, leading to a higher bone mass (FIGS. 10B-D). Biodistribution analysis showed that miR-34a level in the bone marrow was the highest, and further increased by 5-fold by miR-34a-CH, indicating an efficient miR-34a delivery (FIG. 3G).

In addition to acute systemic miR-34a treatment, the inventor also examined the effects of chronic osteoclastic miR-34a over-expression. OVX-induced bone resorption and bone loss were also attenuated in 34a-Tie2-Tg mice without altering OVX effects on bone formation (FIGS. 3H-K, FIG. 10E). These results indicate that osteoclastic miR-34a over-expression is sufficient to impede osteoporosis, and osteoclast is a key site for miR-34a therapeutic benefit.

To determine if osteoclastic miR-34a confers protection from bone metastases, the inventor employed two cancer-cell-cardiac-injection models. First, a human breast cancer cell line (MDA231-BoM-1833) was xenografted into female nude mice. This model allows us to assess cancer cells from human. Second, a mouse melanoma cell line (B16-F10) was allografted into immunocompetent male mice. This model took consideration of adaptive immunity. In both models, bone metastases were attenuated in 34a-Tie2-Tg and 34a-PT-Tg mice but exacerbated in 34a-KO and 34a-Het mice (FIGS. 3L-O, FIGS. 11A-F). Since miR-34a remained intact in the exogenous cancer cells, the altered bone metastases resulted from the altered miR-34a in the bone microenvironment of the host.

Pharmacologically, the inventor tested both a treatment protocol using the human breast cancer model and a prevention protocol using the mouse melanoma model. In both cases, bone metastases were diminished by miR-34a-CH (FIGS. 3P-S). Systemic miR-34a-CH delivery affected neither tumor growth nor metastasis to other organs such as lung (FIGS. 12A-B). Moreover, treating only the cancer cells with miR-34a-CH before injection had no effect (FIGS. 12C-D). Consistent with the published finding that miR-34abc deletion does not increase tumorigenesis (Concepcion et al., 2012), 34a-KO mice also showed unaltered cancer susceptibility (FIG. 12E).

Since systemic miR-34a-CH treatment not only decreases bone resorption but also increases bone formation, the inventor examined the effects of miR-34a over-expression in osteoblasts. She bred the CAG34a mice with Osterix-CreER mice to generate 34a-Osx-Tg mice. Osteoblast differentiation was reduced for 34a-KO and 34a-Het mice, but increased for 34a-Osx-Tg mice (FIGS. 13A-D). Consequently, 34a-Osx-Tg mice exhibited a higher bone formation but unaltered bone resorption, leading to an increased bone mass (FIGS. 13E-G). Importantly however, the elevated bone formation alone in the 34a-Osx-Tg mice was insufficient to attenuate either OVX-induced bone loss or cancer bone metastases (FIGS. 13H-I). Together, conditional miR-34a transgenic mouse models pinpointed the mechanisms underlying the therapeutic benefits of miR-34a by revealing that osteoclast, rather than cancer cell or osteoblast, is the critical and essential player.

To elucidate the mechanisms, the inventor identified Tgif2 as a novel direct miR-34a target in the osteoclast lineage (FIGS. 10A-C). Tgif2 expression was suppressed by miR-34a gain-of-function, but increased by miR-34a loss-of-function, in both mouse and human osteoclast cultures (FIGS. 4A-B, FIGS. 14D-E). The miR-34a seed region in Tgif2 3'UTR is evolutionarily conserved in mammals (FIG. 4C). Luciferase reporter assay showed that Tgif2 3'UTR is sufficient to confer miR-34a regulation (FIGS. 4D-E). Importantly, when the miR-34a seed region in the Tgif2 3'UTR was mutated, miR-34a regulation was abolished (FIGS. 4D-E).

Tgif2 expression was increased during WT osteoclast differentiation (FIG. 4B). Tgif2-KO and Tgif2-Het mice had lower bone resorption and higher bone mass (FIGS. 4F-H, FIG. 14F). Tgif2 deletion reduced osteoclast differentiation, and abolished the anti-osteoclastogenic effects of miR-34a (FIGS. 4I-J). Moreover, Tgif2/miR-34a double knockout mice (DKO) could no longer increase osteoclast differentiation or bone resorption (FIGS. 4L-L) compared to Tgif2-KO mice. These results indicate that Tgif2 is pro-osteoclastogenic and essential for miR-34a regulation.

The inventor next investigated how Tgif2 potentiates RANKL signaling. Transfection assays revealed that NFATc1, c-fos and c-jun, also to a lesser extent NFκB (p65), could induce Tgif2 expression (FIG. 4M). Response elements for NFATc1 and AP-1, but not NFκB, were identified in the Tgif2 promoter region (−5 Kb to +5 Kb). ChIP analysis in osteoclast cultures showed that NFATc1, c-jun and c-fos bound to these sites upon RANKL stimulation, leading to activated Tgif2 transcription shown by the elevated H3K4me3 level at the transcription start site (FIG. 4N). This indicates that NFATc1 and AP-1 induce Tgif2 expression during osteoclastogenesis.

Luciferase reporter assay showed that Tgif2 augmented the activity of NFATc1, NFκB and c-Jun, but not c-fos (FIG. 4O). Consistently, the activity of endogenous NFATc1, NFκB and c-Jun, but not c-fos, was reduced in Tgif2-KO cultures and enhanced in 34a-KO cultures (FIG. 4P). Furthermore, NFATc1 mRNA, c-Jun phosphorylation and IκBα degradation were decreased in Tgif2-KO cultures and increased in 34a-KO cultures (FIGS. 4Q-R). Therefore, Tgif2 potentiates osteoclastogenesis via a positive feedback loop in which RANKL-induced transcription factors activate Tgif2 expression, and Tgif2 in turn promotes their activity. Collectively, these findings reveal Tgif2 as a novel yet critical regulator of osteoclastogenesis and bone resorption, as well as a key miR-34a direct target that is essential for miR-34a regulation (FIG. 4S).

Example 3—Discussion

This study has identified miR-34a as a novel yet critical suppressor of osteoclastogenesis. Genetically, osteoclastic miR-34a over-expression decreases bone resorption leading to high bone mass, whereas miR-34a deletion increases bone resorption leading to low bone mass. Mechanistically, miR-34a inhibits osteoclastogenesis by downregulating the expression of Tgif2, a new pro-osteoclastogenic transcription factor. Pharmacologically, systemic miR-34a delivery via a chitosan nanoparticle vehicle attenuates ovariectomy-induced bone loss and bone metastases of breast cancer and melanoma. These findings not only reveal miR-34a as a key regulator of skeletal physiology but also highlight miR-34a as a promising new therapeutic for osteoporosis and cancer bone metastasis (FIG. 7).

A wealth of mouse genetic models have contributed to the elucidation of the transcription factors and signaling pathways that regulate osteoclastogenesis and osteoblastogenesis, two essential processes in skeletal homeostasis and bone regeneration. However, the roles of miRNAs in bone physiology have just begun to emerge. Recent studies show that osteoblast-specific gain-of-function of miR-34b/c, the other two members of the miR-34 family, decreases bone mass by suppressing osteoblastogenesis and bone formation (Bae et al., 2012; Wei et al., 2012a). Here, the inventor shows that osteoclast-specific miR-34a gain-of-function protects bone by suppressing osteoclastogenesis and bone resorption. These findings uncover an interesting functional divergence among the miR-34 family members: miR-34a acts in the hematopoietic lineage to inhibit osteoclastogenesis, whereas miR-34b/c acts in the mesenchymal lineage to inhibit osteoblastogenesis; thus achieving a physiological balance between bone resorption and bone formation via the differential regulation of miR-34a vs. miR-34b/c.

Importantly, these in vivo genetic and pharmacological studies identify miR-34a as not only a physiologically relevant modulator of skeletal turnover but also a functionally effective anti-osteoporosis and anti-cancer strategy. In light of the remarkable potential of miRNAs as therapeutics, the inventor's findings have opened an exciting avenue for the development of a whole new generation of RNA-based osteo-protective medicine and skeletal disease treatments. More fundamentally, a provocative question in the future is how this miRNA network intertwines and communicates with the transcriptional and signaling network to orchestrate osteoclast differentiation and bone remodeling in response to a variety of developmental and metabolic cues under physiological and pathological conditions.

The miR-34 family of miRNAs (miR-34a/b/c) is commonly deleted in human cancers (Chang et al., 2007; Lodygin et al., 2008; Welch et al., 2007). Several reports have discovered miR-34s as transcriptional targets of p53 that contribute in vitro to p53-induction of apoptosis, cell cycle arrest, and senescence (Bommer et al., 2007; Chang et al., 2007; Corney et al., 2007; He et al., 2007; Hermeking, 2007; Raver-Shapira et al., 2007; Tarasov et al., 2007; Tazawa et al., 2007). Thus, miR-34s have been proposed as critical mediators of p53 function and potential tumor suppressors. Surprisingly, recent studies report that complete loss-of-function in miR-34a/b/c triple KO mice exhibit intact p53 function without any increased susceptibility to tumorigenesis (Concepcion et al., 2012) (inventor's unpublished observations). Nonetheless, pharmacological studies indicate that systemic miR-34a administration in mice can indeed attenuate cancer progression and lung metastasis (Liu et al., 2011; Pramanik et al., 2011; Trang et al., 2011; Wiggins et al., 2010), although the effects of miR-34a on bone metastasis have never been investigated until the current study. This raises the intriguing possibility that the tumor-suppressive and metastasis-blocking effects of miR-34a may reside in other tissues and cell types that constitute the tumor microenvironment such as the osteoclasts in the bone metastatic niche. Indeed, these findings illustrate that bone metastases of cancers are effectively impaired by miR-34a over-expression in the osteoclast lineage but exacerbated by loss of miR-34a therein, thus providing the first in vivo genetic evidence that miR-34a opposes malignant progression of tumor cells by disarming the cancer metastatic niche.

All of the compositions and methods disclosed and claimed herein can be made and executed without undue experimentation in light of the present disclosure. While the compositions and methods of this invention have been described in terms of preferred embodiments, it will be apparent to those of skill in the art that variations may be applied to the compositions and methods, and in the steps or in the sequence of steps of the methods described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

VIII. REFERENCES

The following references, to the extent that they provide exemplary procedural or other details supplementary to those set forth herein, are specifically incorporated herein by reference.

Angel et al., *Cell*, 49:729, 1987b.
Angel et al., *Mol. Cell. Biol.*, 7:2256, 1987a.
Ash et al., *Nature* 283:669-670, 1980.
Ashton et al., *Bone*, 6:313-319, 1985.
Aubin, *Biochem. Cell Biology*, 76:899-910, 1998.

Bae et al., *Hum Mol Genet* 21:2991-3000, 2012.
Baichwal and Sugden, In: *Gene Transfer*, Kucherlapati (Ed.), Plenum Press, NY, 117-48, 1986.
Banerji et al., *Cell*, 27(2 Pt 1):299-308, 1981.
Banerji et al., *Cell*, 33(3):729-740, 1983.
Benvenisty and Neshif, *Proc. Natl. Acad. Sci. USA*, 83(24):9551-9555, 1986.
Berkhout et al., *Cell*, 59:273-282, 1989.
Blanar et al., *EMBO J.*, 8:1139, 1989.
Bleiberg, *Connect Tissue Res.*, 14:121-127, 1985.
Bodine et al., *EMBO J.*, 6:2997, 1987.
Bommer et al., *Current Biology: CB* 17, 1298-1307, 2007.
Boshart et al., *Cell*, 41:521, 1985.
Bosze et al., *EMBO J.*, 5(7):1615-1623, 1986.
Braddock et al., *Cell*, 58:269, 1989.
Brown and Coleman, *Nat Rev Clin Oncol* 9, 110-118, 2012.
Bulla et al., *J. Virol.*, 62:1437, 1986.
Campbell et al., *Am. Rev. Respir. Dis.*, 130(3):417-423, 1984.
Campo et al., *Nature*, 303:77, 1983.
Care et aL, *Nat. Med.* 13:613-618, 2007.
Carrington et al. *Science*, 301(5631):336-338, 2003.
Celander and Haseltine, *J. Virology*, 61:269, 1987.
Celander et al., *J. Virology*, 62:1314, 1988.
Chandler et al., *Cell*, 33:489, 1983.
Chang et al., *Mol. Cell. Biol.*, 9:2153, 1989.
Chang et al., *Molecular Cell* 26, 745-752, 2007.
Chatterjee et al., *Proc. Natl. Acad. Sci. USA*, 86:9114, 1989.
Chen and Okayama, *Mol. Cell Biol.*, 7(8):2745-2752, 1987.
Chirgwin and Guise, *Crit Rev Eukaryot Gene Expr* 10, 159-178, 2000.
Chivukula and Mendell, *Trends Biochem Sci* 33, 474-481, 2008.
Choi et al., *Cell*, 53:519, 1988.
Choi et al., *Nature Cell Bology* 13, 1353-1360, 2011.
Clausen et al., *Transgenic Res* 8, 265-277, 1999.
Cohen et al., *J. Cell. Physiol.*, 5:75, 1987.
Coleman, *Cancer* 80, 1588-1594, 1997.
Coleman, *Clinical Oncology* 9, 76-78, 2012.
Concepcion et al., *PLoS Genet* 8, e1002797, 2012.
Constien et al., *Genesis* 30, 36-44, 2001.
Corney et al., *Cancer Research* 67, 8433-8438, 2007.
Costa et al., *Mol. Cell. Biol.*, 8:81, 1988.
Coupar et al., *Gene*, 68:1-10, 1988.
Cripe et al., *EMBO J.*, 6:3745, 1987.
Dandolo et al., *J. Virology*, 47:55-64, 1983.
De Villiers et al., *Nature*, 312(5991):242-246, 1984.
Deschamps et al., *Science*, 230:1174-1177, 1985.
Dubensky et al., *Proc. Natl. Acad. Sci. USA*, 81:7529-7533, 1984.
Edbrooke et al., *Mol. Cell. Biol.*, 9:1908, 1989.
Edlund et al., *Science*, 230:912-916, 1985.
Edwards and Mundy, *Int J Med Sci* 5, 263-272, 2008.
Ell and Kang, *Cell* 151, 690-690 e691, 2012.
EPO 0273085
Fatkin et al., *J. Clin. Invest.*, 106(11):1351-1359, 2000.
Fechheimer, et al., *Proc Natl. Acad. Sci. USA*, 84:8463-8467, 1987.
Feng and Holland, *Nature*, 334:6178, 1988.
Ferkol et al., *FASEB J.*, 7:1081-1091, 1993.
Firak and Subramanian, *Mol. Cell. Biol.*, 6:3667, 1986.
Foecking and Hofstetter, *Gene*, 45(1):101-105, 1986.
Fraley et al., *Proc. Natl. Acad. Sci. USA*, 76:3348-3352, 1979.
Friedenstein et al., *Exp. Hematol.*, 10:217-227, 1982.
Friedenstein et al., *Transplantation*, 6:230-247, 1968.
Friedman et al., *Genes Devel.*, 3:1314, 1989.
Fujita et al., *Cell*, 49:357, 1987.
Fukuda et al., *Genesis* 44, 159-167, 2006.
Fukuda et al., *Mol Cell Biol* 25, 5270-5281, 2005.
Garcia et al., *Nat Struct Mol Biol* 18, 1139-1146, 2011.
Ghosh and Bachhawat, In: *Liver Diseases, Targeted Diagnosis and Therapy Using Specific Receptors and Ligands*, Wu et al. (Eds.), Marcel Dekker, NY, 87-104, 1991.
Gilles et al., *Cell*, 33:717, 1983.
Gloss et al., *EMBO J.*, 6:3735, 1987.
Godbout et al., *Mol. Cell. Biol.*, 8:1169, 1988.
Goodbourn and Maniatis, *Proc. Natl. Acad. Sci. USA*, 85:1447, 1988.
Goodbourn et al., *Cell*, 45:601, 1986.
Gopal, *Mol. Cell Biol.*, 5:1188-1190, 1985.
Graham and Van Der Eb, *Virology*, 52:456-467, 1973.
Greene et al., *Immunology Today*, 10:272, 1989
Grimson et al., *Mol Cell* 27, 91-105, 2007.
Gronthos et al., *Blood*, 84:4164-4173, 1994.
Gronthos et al., *J. Bone Min. Res.*, 14:47-56, 1999.
Grosschedl and Baltimore, *Cell*, 41:885, 1985.
Harland and Weintraub, *J. Cell Biol.*, 101(3):1094-1099, 1985.
Haslinger et al., *Proc. Natl. Acad. Sci. USA*, 82:8572, 1985.
Hatley et al., *Cancer Cell* 18, 282-293, 2010.
Hauber et al., *J. Virology*, 62:673, 1988.
Hen et al., *Nature*, 321:249, 1986.
Hensel et al., *Lymphokine Res.*, 8:347, 1989.
Hermeking, *Cancer Cell* 12, 414-418, 2007.
Hermonat and Muzycska, *Proc. Natl. Acad. Sci. USA*, 81:6466-6470, 1984.
Hildebrand and Ruegsegger, *Comput Methods Biomech Biomed Engin* 1, 15-23, 1997.
Hirochika et al., *J. Virol.*, 61:2599, 1987.
Holbrook et al., *Virology*, 157:211, 1987.
Horlick and Benfield, *Mol. Cell. Biol.*, 9:2396, 1989.
Horwich et al. *J. Virol.*, 64:642-650, 1990.
Huang et al., *Cell*, 27:245, 1981.
Hug et al., *Mol. Cell. Biol.*, 8:3065, 1988.
Hutvagner et al., *PLoS Biol.*, 2(4):E98, 2004.
Hwang et al., *Mol. Cell. Biol.*, 10:585, 1990.
Imagawa et al., *Cell*, 51:251, 1987.
Imbra et al., *Nature*, 323:555, 1986.
Imler et al., *Mol. Cell. Biol.*, 7:2558, 1987.
Imperiale et al., *Mol. Cell. Biol.*, 4:875, 1984.
Jaiswal et al., *J. Biol. Chem.*, 275:9645-9652, 2000.
Jakobovits et al., *Mol. Cell. Biol.*, 8:2555, 1988.
Jameel and Siddiqui, *Mol. Cell. Biol.*, 6:710, 1986.
Jaynes et al., *Mol. Cell. Biol.*, 8:62, 1988.
Jin et al., *Molecular Endocrinology*, 2012.
Johnson et al., *Mol. Cell. Biol.*, 9:3393, 1989.
Kadesch and Berg, *Mol. Cell. Biol.*, 6:2593, 1986.
Kadiyala et al., *Cell Transplantation*, 6:125-134, 1997.
Kale et al., *Nat. Biotech.*, 18:954-958, 2000.
Kaneda et al., *Science*, 243:375-378, 1989.
Kang et al., *Cancer Cell* 3, 537-549, 2003.
Karin et al., *Mol. Cell. Biol.*, 7:606, 1987.
Kasinski and Slack, *Nat Rev Cancer* 11, 849-864, 2011.
Katinka et al., *Cell*, 20:393, 1980.
Katinka et al., *Nature*, 290:720, 1981.
Kato and Slack, *Biol Cell*, 100:71-81, 2008.
Kato et al, *J. Biol. Chem.*, 266:3361-3364, 1991.
Kawamoto et al., *Mol. Cell. Biol.*, 8:267, 1988.
Khosla et al., *J Bone Miner Res* 22, 1479-1491, 2007.
Kiledjian et al., *Mol. Cell. Biol.*, 8:145, 1988.
Kiriazis and Kranias, *Annu. Rev. Physiol.*, 62:321-351, 2000.
Kisanuki et al., *Dev Biol* 230, 230-242, 2001.

Klamut et al., *Mol. Cell. Biol.*, 10:193, 1990.
Klein et al., *Nature*, 327:70-73, 1987.
Koch et al., *Mol. Cell. Biol.*, 9:303, 1989.
Krenz and Robbins, *J. Am. Coll. Cardiol.*, 44:2390-2397, 2004.
Kriegler and Botchan, In: *Eukaryotic Viral Vectors*, Gluzman (Ed.), Cold Spring Harbor: Cold Spring Harbor Laboratory, NY, 1982.
Kriegler and Botchan, *Mol. Cell. Biol.*, 3:325, 1983a.
Kriegler et al., *Cell*, 38:483, 1984.
Kriegler et al., *Cell*, 53:45, 1988.
Kriegler et al., In: *Gene Expression*, Alan Liss (Ed.), Hamer and Rosenberg, New York, 1983b.
Kuhl et al., *Cell*, 50:1057, 1987.
Kunz et al., *Nucl. Acids Res.*, 17:1121, 1989.
Lacey et al., *Cell* 93, 165-176, 1998.
Lagos-Quintana et al., *Science*, 294(5543):853-858, 2001.
Larsen et al., *Proc Natl. Acad. Sci. USA.*, 83:8283, 1986.
Laspia et al., *Cell*, 59:283, 1989.
Latimer et al., *Mol. Cell. Biol.*, 10:760, 1990.
Lau et al., *Science*, 294(5543):858-862, 2001.
Lee and Ambros, *Science*, 294(5543):862-864, 2001.
Lee et al., *Nature*, 294:228, 1981.
Levinson et al., *Nature*, 295:79, 1982.
Lewis et al., *Cell* 120, 15-20, 2005.
Liu et al., *Nature Medicine* 17, 211-215, 2011.
Lodygin et al., *Cell Cycle* 7, 2591-2600, 2008.
Lowes et al., *J. Clin. Invest.*, 100(9):2315-2324, 1997.
Luria et al., *EMBO J.*, 6:3307, 1987.
Lusky and Botchan, *Proc. Natl. Acad. Sci. USA*, 83:3609, 1986.
Lusky et al., *Mol. Cell. Biol.*, 3:1108, 1983.
Majors et al., *Proc. Natl. Acad. Sci. USA*, 80:5866, 1983.
McNeall et al., *Gene*, 76:81, 1989.
Meister et al., *Nature*, 431:343-9, 2004.
Miksicek et al., *Cell*, 46:203, 1986.
Moreau et al., *Nucl. Acids Res.*, 9:6047, 1981.
Muesing et al., *Cell*, 48:691, 1987.
Mundy, *Nat Rev Cancer* 2, 584-593, 2002.
Nicolas and Rubinstein, In: Vectors: *A survey of molecular cloning vectors and their uses*, Rodriguez and Denhardt (Eds), Stoneham: Butterworth, 494-513, 1988.
Nicolau and Sene, *Biochim. Biophys. Acta*, 721:185-190, 1982.
Nicolau et al., *Methods Enzymol.*, 149:157-176, 1987.
Novack and Teitelbaum, *Annu Rev Pathol* 3, 457-484, 2008.
Omitz et al., *Mol. Cell. Biol.*, 7:3466, 1987.
Ondek et al., *EMBO J.*, 6:1017, 1987.
Osaki et al., *Mol Ther* 19, 1123-1130, 2011.
Palmiter et al., *Nature*, 300:611, 1982.
Pech et al., *Mol. Cell. Biol.*, 9:396, 1989.
Perales et al., *Proc. Natl. Acad. Sci. USA*, 91:4086-4090, 1994.
Perez-Stable and Constantini, *Mol. Cell. Biol.*, 10:1116, 1990.
Petite et al., *Nat. Biotech.*, 18:959-963, 2000.
Phinney et al., *J. Cellular Biochem.*, 75:424-436, 1999.
Picard and Schaffner, *Nature*, 307:83, 1984.
Pinkert et al., *Genes and Dev.*, 1:268, 1987.
Pittenger et al., *Science* 284, 143-147, 1999.
Pittenger et al., *Science*, 284:143-147, 1999.
Ponta et al., *Proc. Natl. Acad. Sci. USA*, 82:1020, 1985.
Porton et al., *Mol. Cell. Biol.*, 10:1076, 1990.
Potter et al., *Proc. Natl. Acad. Sci. USA*, 81:7161-7165, 1984.
Powers et al., *Development* 137, 249-259, 2010.
Pramanik et al., *Molecular Cancer Therapeutics* 10, 1470-1480, 2011.
Queen et al., *Cell*, 35:741, 1983.
Quinn et al., *Mol. Cell. Biol.*, 9:4713, 1989.
Raver-Shapira et al., *Molecular cell* 26, 731-743, 2007.
Reddi and Huggins, *Proc. Natl. Acad. Sci. USA*, 69:1601-1605, 1972.
Redondo et al., *Science*, 247:1225, 1990.
Reisman and Rotter, *Mol. Cell. Biol.*, 9:3571, 1989.
Remington's Pharmaceutical Sciences, 15$^{th}$ ed., pages 1035-1038 and 1570-1580, Mack Publishing Company, Easton, Pa., 1980.
Resendez et al., *Mol. Cell. Biol.*, 8:4579, 1988.
Ridgeway, In: *Vectors: A Survey of Molecular Cloning Vectors and Their Uses*, Rodriguez et al. (Eds.), Stoneham: Butterworth, 467-492, 1988.
Ripe et al., *Mol. Cell. Biol.*, 9:2224, 1989.
Rippe, et al., *Mol. Cell Biol.*, 10:689-695, 1990.
Rittling et al., *Nuc. Acids Res.*, 17:1619, 1989.
Roodman, *N Engl J Med* 350, 1655-1664, 2004.
Rosen et al., *Cell*, 41:813, 1988.
Sakai et al., *Genes and Dev.*, 2:1144, 1988.
Satake et al., *J. Virology*, 62:970, 1988.
Schaffner et al., *J. Mol. Biol.*, 201:81, 1988.
Scheven et al., *Nature* 321, 79-81, 1986.
Searle et al., *Mol. Cell. Biol.*, 5:1480, 1985.
Sharp et al., *Cell*, 59:229, 1989.
Shaul et al., *EMBO J.*, 6:1913, 1987.
Sherman et al., *Mol. Cell. Biol.*, 9:50, 1989.
Sleigh et al., *J. EMBO*, 4:3831, 1985.
Spalholz et al., *Cell*, 42:183, 1985.
Spandau et al., *J. Virology*, 62:427, 1988.
Spandidos & Wilkie, *EMBO J.*, 2:1193, 1983.
Stephens et al., *Biochem. J.*, 248:1, 1987.
Stuart et al., *Nature*, 317:828, 1985.
Sullivan et al., *Mol. Cell. Biol.*, 7:3315, 1987.
Swartzendruber et al., *J. Cell. Physiology*, 85:179, 1975.
Takebe et al., *Mol. Cell. Biol.*, 8:466, 1988.
Takeshita et al, *Mol Ther* 18, 181-187, 2010.
Tarasov et al., *Cell Cycle* 6, 1586-1593, 2007.
Tavernier et al., *Nature*, 301:634, 1983.
Taylor et al., *J. Biol. Chem.*, 264:15160, 1989.
Taylor et al., *Mol. Cell. Biol.*, 10:165, 1990a.
Taylor et al., *Mol. Cell. Biol.*, 10:176, 1990b.
Tazawa et al., *Proceedings of the National Academy of Sciences of the United States of America* 104, 15472-15477, 2007.
Temin, In: *Gene Transfer*, Kucherlapati (Ed.), NY, Plenum Press, 149-188, 1986.
Thiesen et al., *J. Virology*, 62:614, 1988.
Tondravi et al., *Nature* 386, 81-84, 1997.
Trang et al., *Molecular therapy: the journal of the American Society of Gene Therapy* 19, 1116-1122, 2011.
Tronche et al., *Mol. Biol. Med.*, 7:173, 1990.
Tronche et al., *Mol. Cell Biol.*, 9(11):4759-4766, 1989.
Trudel et al., *Genes and Dev.*, 6:954, 1987.
Tur-Kaspa et al., *Mol. Cell Biol.*, 6:716-718, 1986.
Tyndell et al., *Nuc. Acids. Res.*, 9:6231, 1981.
U.S. Pat. No. 5,844,107
U.S. Pat. No. 5,877,302
U.S. Pat. No. 5,972,703
U.S. Pat. No. 5,972,900
U.S. Pat. No. 5,972,901
U.S. Pat. No. 6,008,336
U.S. Pat. No. 6,077,835
U.S. Pat. No. 6,200,801
U.S. Pat. No. 7,740,883

U.S. Pat. No. 7,883,723
U.S. Pat. No. 7,901,666
U.S. Pat. No. 7,901,711
U.S. Pat. No. 8,137,697
U.S. Pat. No. 8,187,571
U.S. Pat. No. 8,449,915
U.S. Pat. No. 8,502,015
U.S. Publn. 20020150626
U.S. Publn. 20030032615
U.S. Publn. 20030203865
U.S. Publn. 20040048787
U.S. Publn. 20130189367
U.S. Publn. 20130149385
U.S. Publn. 20130078210
U.S. Publn. 20120269729
U.S. Publn. 20120128781
U.S. Publn. 20120107268
U.S. Publn. 20120040004
U.S. Publn. 20120039854
U.S. Publn. 20110305765
U.S. Publn. 20110064676
U.S. Publn. 20110064665
U.S. Publn. 20110059162
U.S. Publn. 20100267139
U.S. Publn. 20100260686

Wagner et al., *Proc. Natl. Acad. Sci. USA* 87(9):3410-3414, 1990.
Wan et al., *Genes Dev* 21, 1895-1908, 2007b.
Wan et al., *Nat Med* 13, 1496-1503, 2007a.
Wang et al., *Cell,* 47:241, 1986.
Weber et al., *Cell,* 36:983, 1984.
Wei et al., *Cell Metab* 11, 503-516, 2010.
Wei et al., *Mol Cell Biol* 31, 4692-4705, 2011b.
Wei et al., *Mol Cell Biol* 31, 4706-4719, 2011a.
Wei et al., *Proc Natl Acad Sci USA* 109, 3143-3148, 2012b.
Wei et al., *Journal of Cell Biology* 197, 509-521, 2012a.
Weinberger et al. *Mol. Cell. BioL,* 8:988, 1984.
Welch et al., *Oncogene* 26, 5017-5022, 2007.
Wiggins et al., *Cancer Research* 70, 5923-5930, 2010.
Winoto et al., *Cell,* 59:649, 1989.
Wong et al., *Gene,* 10:87-94, 1980.
Wu and Wu, *Biochemistry,* 27: 887-892, 1988.
Wu and Wu, *J. Biol. Chem.,* 262:4429-4432, 1987.
Yang et al., *Nat. Med.* 13:486-491, 2007.
Yang et al., *Proc. Natl. Acad. Sci. USA,* 87:4144-4148, 1990.
Yasuda et cd., *Proc Natl Acad Sci USA* 95, 3597-3602, 1998.
Yutzey et al. *Mol. Cell. Biol.,* 9:1397, 1989.
Zelenin et al., *FEBS Lett.,* 287(1-2):118-120, 1991.
Zeng et al., *Cancer Res.,* 62(13):3630-3635, 2002.

SEQUENCE LISTING

```
<160> NUMBER OF SEQ ID NOS: 2

<210> SEQ ID NO 1
<211> LENGTH: 110
<212> TYPE: RNA
<213> ORGANISM: Artificial
<220> FEATURE:
<223> OTHER INFORMATION: Synthetic primer

<400> SEQUENCE: 1
ggccagcugu gaguguuucu uuggcagugu cuuagcuggu uguugugagc aauaguaagg      60
aagcaaucag caaguauacu gcccuagaag ugcugcacgu ugugggccc                 110

<210> SEQ ID NO 2
<211> LENGTH: 102
<212> TYPE: RNA
<213> ORGANISM: Artificial
<220> FEATURE:
<223> OTHER INFORMATION: Synthetic primer

<400> SEQUENCE: 2
ccagcuguga guaauucuuu ggcagugucu uagcugguug uugugaguau uagcuaagga      60
agcaaucagc aaguauacug cccuagaagu gcugcacauu gu                        102
```

U.S. Publn. 20100098768
U.S. Publn. 20100015232
U.S. Publn. 20090130186
U.S. Publn. 20080233060
U.S. Publn. 20080219938
U.S. Publn. 20080095810
U.S. Publn. 20060013885
U.S. Publn. 20050226938
Uluckan et al., *Journal Cellular Biochemistry* 104, 1311-1323, 2008.
Vannice et al., *J. Virology,* 62:1305, 1988.
Vasseur et al., *Proc Natl. Acad. Sci. USA,* 77:1068, 1980.
Ventura et al., *Cell* 136, 586-591, 2009.

The invention claimed is:

1. A method of increasing bone mass and/or volume in a subject comprising:
   (a) identifying a patient in need of increased bone mass and/or volume; and
   (b) administering to a bone target site in said subject miR-34a or an expression vector that expresses miR-34a,
   wherein said subject does not have cancer.

2. The method of claim 1, wherein said agonist is formulated with a nanoparticle delivery vehicle.

3. The method of claim 1, wherein said agonist is injected at said site.

4. The method of claim 1, wherein said agonist is comprised in a time-release device implanted at said site.

5. The method of claim 1, wherein said subject is a human.

6. The method of claim 1, wherein said subject is a non-human animal.

7. The method of claim 1, further comprising at least a second administration of said agonist.

8. The method of claim 1, wherein said subject suffers from osteoporosis, bone fracture, bone loss due to trauma, rheumatoid arthritis or Paget's Disease.

9. The method of claim 1, wherein said miR-34 contains at least one non-natural base.

10. A method of increasing bone growth in a subject comprising:
   (a) administering miR-34a or an expression vector that expresses miR-34a, to a bone target site in said subject,
   (b) assessing bone mass in said subject after step (a).

11. The method of claim 10, wherein said agonist is miR-34a or an expression vector that expresses miR-34a.

12. The method of claim 11, wherein said miR-34a is formulated with a nanoparticle delivery vehicle.

13. The method of claim 10, wherein said subject is a human.

14. The method of claim 10, wherein said subject is a non-human animal.

15. The method of claim 10, wherein said miR-34a contains at least one non-natural base.

16. The method of claim 10, further comprising at least a second administration of said agonist.

17. A method of increasing osteoblast number, decreasing osteoclast number, and/or increasing bone strength in a subject comprising:
   (a) identifying a patient in need of increased osteoblast number, decreased osteoclast number, and/or increased bone strength; and
   (b) administering to a bone target site in said subject miR-34a or an expression vector that expresses miR-34a,
wherein said subject does not have cancer.

* * * * *